(12) United States Patent
Sheppard et al.

(10) Patent No.: US 6,573,363 B1
(45) Date of Patent: Jun. 3, 2003

(54) CYSTINE KNOT PROTEIN AND MATERIALS AND METHODS FOR MAKING IT

(75) Inventors: Paul O. Sheppard, Redmond, WA (US); Si Lok, Seattle, WA (US)

(73) Assignee: ZymoGenetics, Inc., Seattle, WA (US)

( * ) Notice: Subject to any disclaimer, the term of this patent is extended or adjusted under 35 U.S.C. 154(b) by 0 days.

(21) Appl. No.: 09/250,124

(22) Filed: Feb. 12, 1999

Related U.S. Application Data

(60) Provisional application No. 60/074,682, filed on Feb. 13, 1998, and provisional application No. 60/102,709, filed on Oct. 1, 1998.

(51) Int. Cl.[7] .......................... C07K 1/00; C07K 14/00
(52) U.S. Cl. .................. 530/350; 424/9.322; 514/2; 930/10
(58) Field of Search .................. 530/350; 424/9.322; 514/2; 930/10

(56) References Cited

U.S. PATENT DOCUMENTS 5,508,261 A    4/1996    Moyle et al. ................. 514/8

OTHER PUBLICATIONS

Smith et al. The challenges of genome sequence annotation or "The devil is in the details". Nature Biotechnology, Nov. 1997, vol. 15, pp. 1222–1223.*

Perez–Vilar et al. Norrie Disease Protein (Norrin) Forms Disulfide–linked Oligomers Associated with the Extracellular Matrix. J. Biol. Chem. Dec. 1997, vol. 272, No. 52, pp. 33410–33415.*

Charlton et al. Protein Metabolism in Insulin–Dependent Diabetes Mellitus. J. Nutr. 1998, vol. 128, pp. 323S–327S.*

Marra, Genbank Accession No. AA709641, 1996.

Wang et al., Genbank Accession No. AC000159, 1997.

Konno, Genbank Accession No. C89076, 1998.

Sasaki et al., *Genomics 49*: 167–179, 1998.

Tuan et al., *Connective Tissue Research 34*: 1–9, 1996.

Fiddes et al., *Journal of Molecular and Applied Genetics 1*:3–18, 1981.

Fiddes et al., *Nature 281*: 351–356, 1979.

* cited by examiner

*Primary Examiner*—Christopher S. F. Low
*Assistant Examiner*—Holly Schnizer
(74) *Attorney, Agent, or Firm*—Paul G. Lunn; Gary E. Parker

(57) ABSTRACT

The present invention relates to polynucleotide and polypeptide molecules for zsig51, a novel member of the cystine knot family of polypeptides. The polypeptides comprise a sequence of amino acid residues that is at least 80% identical in amino acid sequence to residues 1 through 106 of SEQ ID NO:2. The invention further provides therapeutic and diagnostic methods utilizing the polynucleotides, polypeptides, and antagonists of the polypeptides.

1 Claim, 3 Drawing Sheets

CYSTINE KNOT PROTEIN AND MATERIALS AND METHODS FOR MAKING IT

CROSS-REFERENCE TO RELATED APPLICATIONS

This application claims the benefit under 35 U.S.C. §119 (e) of provisional application No. 60/074,682, filed Feb. 13, 1998, and provisional application No. 60/102,709, filed Oct. 1, 1998.

BACKGROUND OF THE INVENTION

In multicellular animals, cell growth, differentiation, and migration are controlled by polypeptide growth factors and hormones. These growth factors play a role in both normal development and pathogenesis, including the development of solid tumors.

Polypeptide growth factors and hormones influence cellular events by binding to cell-surface receptors. Binding initiates a chain of signalling events within the cell, which ultimately results in phenotypic changes such as cell division and production of additional hormones.

One family of hormones is the glycoprotein hormone family, which includes luteinizing hormone, follicle-stimulating hormone, thyroid-stimulating hormone, and chorionic gonadotropin. The first three are synthesized in the anterior pituitary, while chorionic gonadotropin is synthesized in the placenta, reaching a maximum at 10–12 weeks after conception and declining thereafter to the end of pregnancy.

The four glycoprotein hormones are structurally and functionally related. All four are glycosylated and consist of two non-covalently associated subunits, term $\alpha$ and $\beta$ subunits. A single $\alpha$ subunit is common to all four hormones, while the $\beta$ subunits are unique and confer biological specificity. The different $\beta$ subunits are of similar size and have a significant degree of pairwise homology; the $\beta$ subunits of human chorionic gonadotropin (HCG) and human luteinizing hormone are 82% identical, and the other pairs of $\beta$ subunits are about 30–40% identical. Twelve cysteine residues are conserved among the four $\beta$ subunits. The common $\alpha$ subunit exhibits detectable homology to the $\beta$ subunits and includes six of the twelve conserved cysteine residues. See, Fiddes and Goodman, Nature 281:351–356, 1979; Fiddes and Goodman, Nature 286:684–687, 1980; Talmadge et al., Nature 307:37–40, 1984; and Pierce and Parsons, Ann. Rev. Biochem. 50:465–495, 1981. The polypeptides form characteristic higher-order structures having a bow tie-like configuration about a cystine knot, formed by disulfide bonding between three pairs of cysteine residues. Dimerization occurs through hydrophobic interactions between loops of the two monomers. See, Daopin et al., Science 257:369, 1992; Lapthorn et al., Nature 369:455, 1994.

The cystine knot motif and bow tie-like fold are also characteristic of the growth factors transforming growth factor-beta (TGF-$\beta$), nerve growth factor (NGF), and platelet derived growth factor (PDGF). These proteins are all dimers in their active forms, the monomer subunits of which contain from 100 to 130 amino acid residues. Although their amino acid sequences are quite divergent, these proteins, as well as the glycoprotein hormones, all contain the six conserved cysteine residues of the cystine knot.

The glycoprotein hormones act in a stage- and tissue-specific manner. LH, FSH, and TSH are produced in the pituitary. Luteinizing hormone stimulates steroid production in the testes and ovaries, which in turn stimulates spermatogenesis and ovulation. FSH is also a regulator of gametogenesis and steroid hormone synthesis in the gonads. TSH regulates a variety of processes in the thyroid, thereby controlling synthesis and secretion of thyroid hormones. HCG, produced in placenta, stimulates the ovaries to produce steroids that are necessary for the maintenance of pregnancy. For review see Pierce and Parsons, Ann. Rev. Biochem. 50:465–495, 1981.

A more recently discovered member of this family, designated Norrie disease protein (NDP), is believed to be a regulator of neural cell differentiation and proliferation (Berger et al., Nature Genetics 1:199–203, 1992). NDP is expressed in retina, choroid, and fetal and adult brain. A lack of functional NDP is associated with Norrie disease, an X-linked disorder characterized by blindness, deafness, and mental disturbances. A number of variant forms of the protein, including deletions and point mutations, have been identified in Norrie disease patients. See, for example, Berger et al., ibid.; Fuchs et al., Hum. Mol. Genet. 3:655–656, 1994; and Meindl et al., Nature Genetics 2:139–143, 1992.

Another group of related proteins is the growth and differentiation factors (GDFs). One member of this group, known as GDF-8 or myostatin, appears to act as a negative regulator of muscle mass (McPherron and Lee, Nature 387:83–90, 1997; McPherron and Lee, Proc. Natl. Acad. Sci. USA 94:12457–12461, 1997; and Grobet et al., Nat. Genet. 17:17–71, 1997). Many GDFs share 20–40% sequence homology with each other and with TGF-$\beta$ 1, 2, and 3. The discovery of the GDFs supports the postulated existence of "chalones", soluble factors hypothesized to control organ size and regeneration (Bullough, Cancer Res. 25:1683–1727, 1965; Bullough, Biol. Res. 37:307–342, 1992).

The role of hormones in controlling cellular processes makes them likely candidates and targets for therapeutic intervention. Examples of such proteins that are used therapeutically include insulin for the treatment of diabetes and erythropoietin for the treatment of anemia. Gonadotropin has been used to induce ovulation (e.g., Fleming, Am. J. Obstet. Gynecol. 159:376–381, 1988), to induce scrotal descent of cryptorchid testes (Lala et al., J. Urol. 157:1898–1901, 1997), and to stimulate intratesticular testosterone production in men who have undergone varicocelectomy (Yamamoto et al., Arch. Androl. 35:49–55, 1995). Clinical studies have shown that hCG can have antitumor activity against Kaposi's sarcoma (Gill et al., J. Natl. Cancer Inst. 89:1797–1802, 1997). Assays for the presence of chorionic gonadotropin are used to detect pregnancy. Vaccines against hCG have shown promising results in early tests for preventing pregnancy and inhibiting the growth of hormone-dependent cancers (Talwar, Immunol. Cell Biol. 75:184–189, 1997).

In view of the proven clinical utility of hormones, there is a need in the art for additional such molecules for use as therapeutic agents, diagnostic agents, and research tools and reagents.

The present invention provides such polypeptides for these and other uses that should be apparent to those skilled in the art from the teachings herein.

SUMMARY OF THE INVENTION

Within one aspect of the invention there is provided an isolated polypeptide that is at least 80% identical in amino acid sequence to residues 1 through 106 of SEQ ID NO:2. The polypeptide comprises cysteine residues at positions corresponding to residues 8, 34, 38, 66, 96, and 98 of SEQ ID NO:2, a glycine residue at a position corresponding to residue 36 of SEQ ID NO:2, and beta strands corresponding to residues 9–17, 29–34, 38–43, 59–64, 67–71, and 90–95 of SEQ ID NO:2. Within one embodiment of the invention the isolated polypeptide further comprises cysteine residues at positions corresponding to residues 25, 65, 80, and 101 of SEQ ID NO:2. Within a further embodiment, amino acid residues within the polypeptide at positions corresponding to residues 8, 11, 12, 14, 29, 30, 32, 34, 43, 44, 60, 63, 64, 65, 71, 74, 80, 90, 91, 93, and 94 of SEQ ID NO:2 are Cys, His, Pro, Asn, His, Val, Gln, Cys, Phe, Pro, Thr, Ser, Gln, Cys, Leu, Val, Cys, Ile, Phe, Ala, and Arg, respectively, and an amino acid corresponding to residue 75 of SEQ ID NO:2 is Lys or Arg. Within other embodiments the isolated polypeptide comprises residue 1 through residue 106 of SEQ ID NO:2 or residue 1 through residue 106 of SEQ ID NO:29. Within further embodiments, the isolated polypeptide is covalently linked to an affinity tag or to an immunoglobulin constant region.

Within a second aspect of the invention there is provided an isolated protein comprising a first polypeptide complexed to a second polypeptide wherein said protein modulates cell proliferation, differentiation, or metabolism. The first polypeptide is at least 80% identical in amino acid sequence to residues 1 through 106 of SEQ ID NO:2 and comprises cysteine residues at positions corresponding to residues 8, 34, 38, 66, 96, and 98 of SEQ ID NO:2, a glycine residue at a position corresponding to residue 36 of SEQ ID NO:2, and beta strands corresponding to residues 9–17, 29–34, 38–43, 59–64, 67–71, and 90–95 of SEQ ID NO:2. Within one embodiment the first polypeptide further comprises cysteine residues at positions corresponding to residues 25, 65, 80, and 101 of SEQ ID NO:2. Within a further embodiment, amino acid residues of the first polypeptide corresponding to residues 8, 11, 12, 14, 29, 30, 32, 34, 43, 44, 60, 63, 64, 65, 71, 74, 80, 90, 91, 93, and 94 of SEQ ID NO:2 are Cys, His, Pro, Asn, His, Val, Gln, Cys, Phe, Pro, Thr, Ser, Gln, Cys, Leu, Val, Cys, Ile, Phe, Ala, and Arg, respectively; and an amino acid residue corresponding to residue 75 of SEQ ID NO:2 is Lys or Arg. Within another embodiment the protein is a heterodimer. Within a related embodiment the second polypeptide is a glycoprotein hormone common alpha subunit. Within other embodiments the first polypeptide comprises residue 1 through residue 106 of SEQ ID NO:2 or residue 1 through residue 106 of SEQ ID NO:29. Within further embodiments, the protein is a homodimer, such as a homodimer of polypeptides comprising residue 1 through residue 106 of SEQ ID NO:2, or a homodimer of polypeptides comprising residue 1 through residue 106 of SEQ ID NO:29.

Within a third aspect of the invention there is provided an isolated polynucleotide encoding a polypeptide that is at least 90% identical in amino acid sequence to residues 1 through 106 of SEQ ID NO:2, wherein the polypeptide comprises cysteine residues at positions corresponding to residues 8, 34, 38, 66, 96, and 98 of SEQ ID NO:2, a glycine residue at a position corresponding to residue 36 of SEQ ID NO:2, and beta strands corresponding to residues 9–17, 29–34, 38–43, 59–64, 67–71, and 90–95 of SEQ ID NO:2. Within one embodiment the polypeptide further comprises cysteine residues at positions corresponding to residues 25, 65, 80, and 101 of SEQ ID NO:2. Within another embodiment, amino acid residues of the polypeptide corresponding to residues 8, 11, 12, 14, 29, 30, 32, 34, 43, 44, 60, 63, 64, 65, 71, 74, 80, 90, 91, 93, and 94 of SEQ ID NO:2 are Cys, His, Pro, Asn, His, Val, Gln, Cys, Phe, Pro, Thr, Ser, Gln, Cys, Leu, Val, Cys, Ile, Phe, Ala, and Arg, respectively, and an amino acid residue corresponding to residue 75 of SEQ ID NO:2 is Lys or Arg. Within certain additional embodiments of the invention, the polypeptide comprises residue 1 through residue 106 of SEQ ID NO:2 or residue 1 through residue 106 of SEQ ID NO:29. Within another embodiment the polynucleotide further encodes a secretory peptide operably linked to the polypeptide. Within additional embodiments the polynucleotide encodes residue −23 through residue 106 of SEQ ID NO:2 or residue −23 through residue 106 of SEQ ID NO:29. Within further embodiments the polynucleotide comprises a sequence of nucleotides as shown in SEQ ID NO:4 or SEQ ID NO:30 from nucleotide 70 through nucleotide 387. Within other embodiments, the polynucleotide comprises a sequence of nucleotides as shown in SEQ ID NO:1 from nucleotide 125 through nucleotide 442. Within an additional embodiment the polynucleotide is from 318 to 1000 nucleotides in length. The polynucleotide can be DNA or RNA.

Within a fourth aspect of the invention there is provided an expression vector comprising the following operably linked elements: (a) a transcription promoter; (b) a DNA segment encoding a polypeptide as disclosed above; and (c) a transcription terminator. Within one embodiment the DNA segment further encodes a secretory peptide operably linked to the polypeptide. Within further embodiments the DNA segment encodes residue −23 through residue 106 of SEQ ID NO:2 or residue −23 through residue 106 of SEQ ID NO:29.

Within a fifth aspect of the invention there is provided a cultured cell into which has been introduced an expression vector as disclosed above, wherein the cell expresses the polypeptide encoded by the DNA segment. The cell can be used within a method of producing a polypeptide, wherein the method comprises culturing the cell, whereby the cell expresses the polypeptide encoded by the DNA segment, and recovering the expressed polypeptide.

Within a further aspect of the invention there is provided an antibody that specifically binds to an epitope of a polypeptide as disclosed above.

The invention also provides a method for detecting a genetic abnormality in a patient, comprising the steps of (a) obtaining a genetic sample from a patient; (b) incubating the genetic sample with a polynucleotide comprising at least 14 contiguous nucleotides of SEQ ID NO:1 or the complement of SEQ ID NO:1, under conditions wherein the polynucleotide will hybridize to complementary polynucleotide sequence, to produce a first reaction product; (c) comparing the first reaction product to a control reaction product, wherein a difference between the first reaction product and the control reaction product is indicative of a genetic abnormality in the patient.

The invention also provides an oligonucleotide probe or primer comprising 14 contiguous nucleotides of a polynucleotide of SEQ ID NO:4 or a sequence complementary to SEQ ID NO:4. Within one embodiment the probe or primer comprises 14 contiguous nucleotides of a polynucleotide of SEQ ID NO:1 or a sequence complementary to SEQ ID NO:1.

The invention also provides a pharmaceutical composition comprising a polypeptide as disclosed above in combination with a pharmaceutically acceptable vehicle.

These and other aspects of the invention will become evident upon reference to the following detailed description of the invention and the attached drawing.

BRIEF DESCRIPTION OF THE DRAWING

Figure 1B:
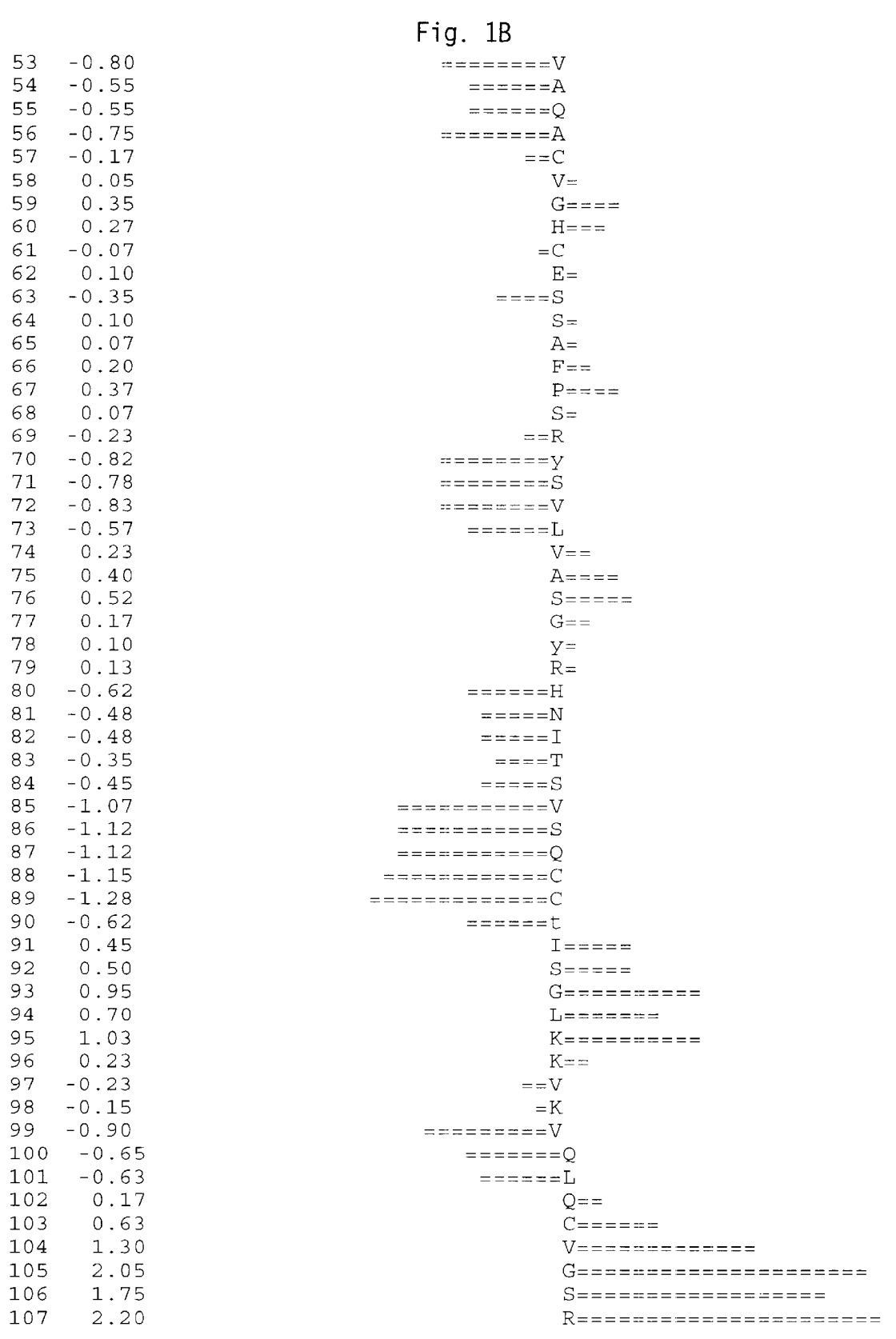

FIGS. 1A, 1B and 1C show a Hopp/Woods hydrophilicity profile of the amino acid sequence shown in SEQ ID NO: 2. The profile is based on a sliding six-residue window. Buried G, S, and T residues and exposed H, Y, and W residues were ignored. These residues are indicated in the figures by lower case letters.

DETAILED DESCRIPTION OF THE INVENTION

Figure 1A:
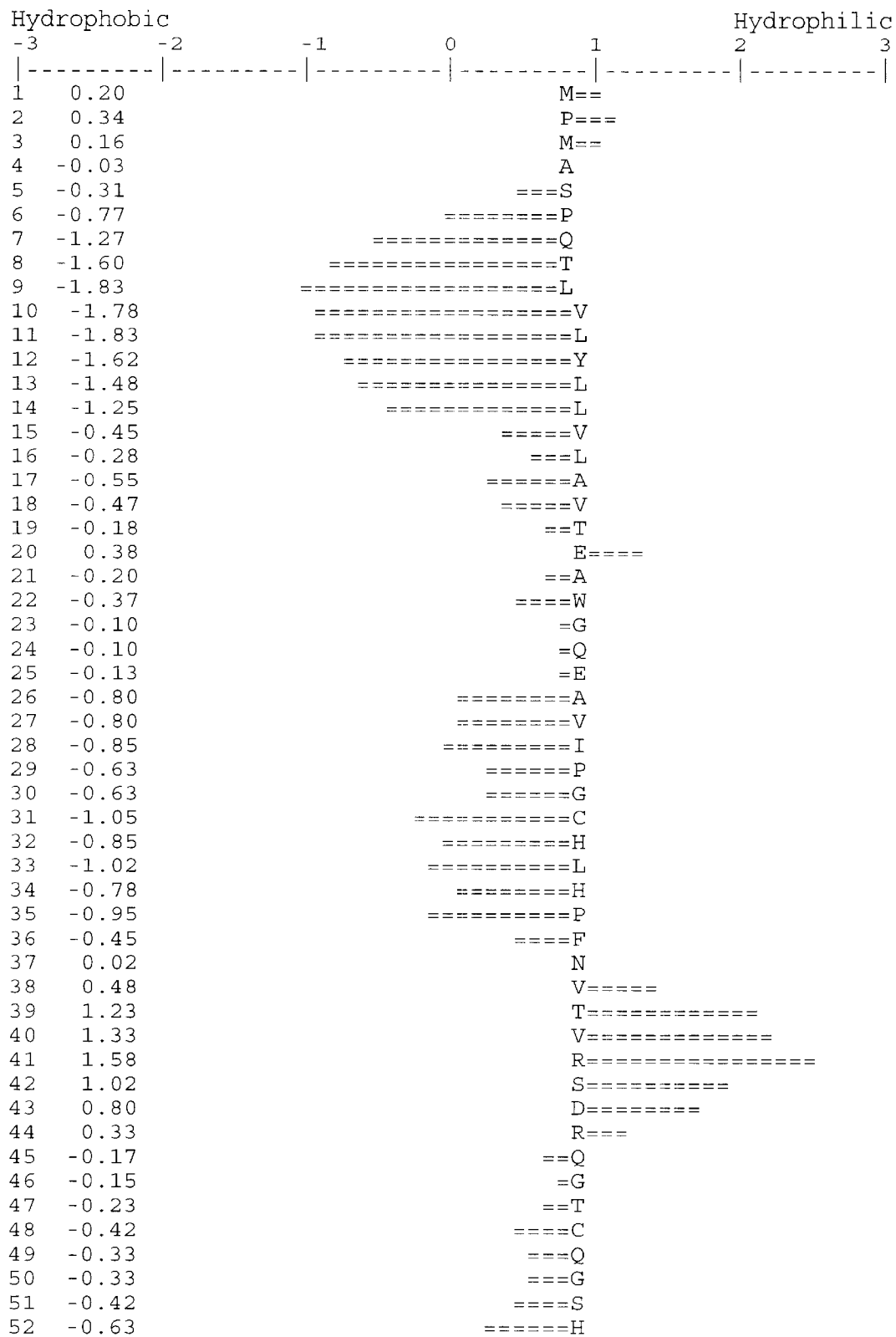
Figure 1C:
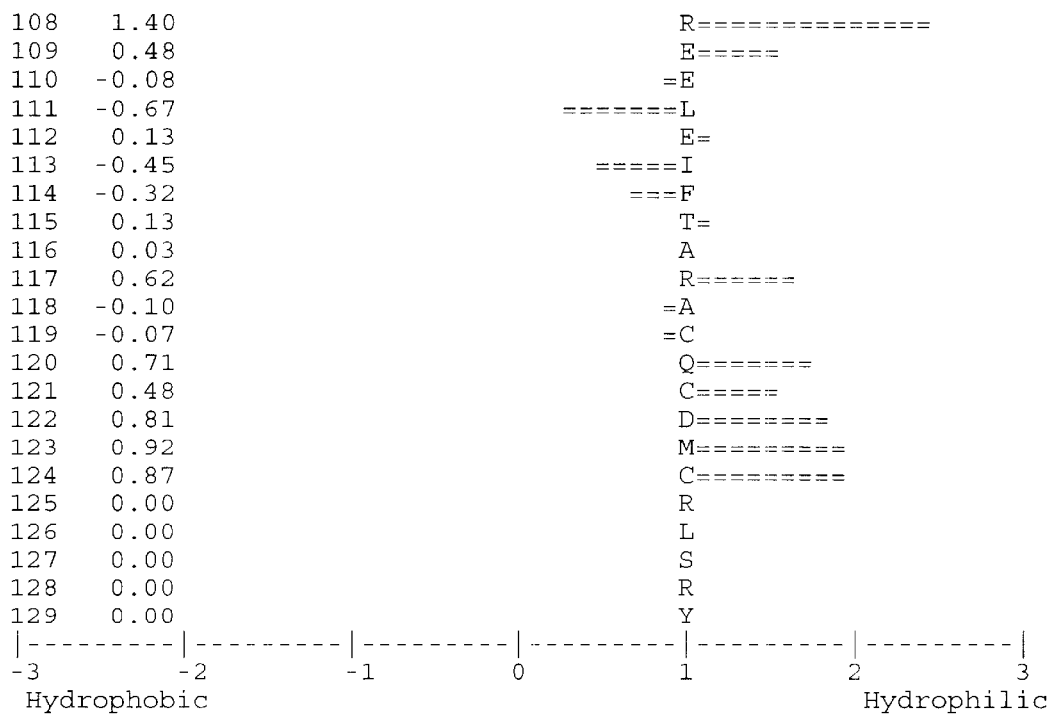

Prior to setting forth the invention in detail, it may be helpful to the understanding thereof to define the following terms:

The term "affinity tag" is used herein to denote a polypeptide segment that can be attached to a second polypeptide to provide for purification of the second polypeptide or provide sites for attachment of the second polypeptide to a substrate. In principal, any peptide or protein for which an antibody or other specific binding agent is available can be used as an affinity tag. Affinity tags include a poly-histidine tract, protein A (Nilsson et al., *EMBO J.* 4:1075, 1985; Nilsson et al., *Methods Enzymol.* 198:3, 1991), glutathione S transferase (Smith and Johnson, *Gene* 67:31, 1988), Glu—Glu affinity tag (Grussenmeyer et al., *Proc. Natl. Acad. Sci. USA* 82:7952–7954, 1985), substance P, Flag™ peptide (Hopp et al., *Biotechnology* 6:1204–1210, 1988), maltose binding protein (Kellerman and Ferenci, *Methods Enzymol.* 90:459–463, 1982; Guan et al., *Gene* 67:21–30, 1987), streptavidin binding peptide, thioredoxin, ubiquitin, cellulose binding protein, T7 polymerase, immunoglobulin constant domain, or other antigenic epitope or binding domain. See, in general, Ford et al., *Protein Expression and Purification* 2: 95–107, 1991. DNAs encoding affinity tags and otehr reagents are available from commercial suppliers (e.g., Pharmacia Biotech, Piscataway, N.J.; Eastman Kodak, New Haven, Conn.; New England Biolabs, Beverly, Mass.).

The term "allelic variant" is used herein to denote any of two or more alternative forms of a gene occupying the same chromosomal locus. Allelic variation arises naturally through mutation, and may result in phenotypic polymorphism within populations. Gene mutations can be silent (no change in the encoded polypeptide) or may encode polypeptides having altered amino acid sequence. The term allelic variant is also used herein to denote a protein encoded by an allelic variant of a gene.

The terms "amino-terminal" and "carboxyl-terminal" are used herein to denote positions within polypeptides. Where the context allows, these terms are used with reference to a particular sequence or portion of a polypeptide to denote proximity or relative position. For example, a certain sequence positioned carboxyl-terminal to a reference sequence within a polypeptide is located proximal to the carboxyl terminus of the reference sequence, but is not necessarily at the carboxyl terminus of the complete polypeptide.

A "beta-strand-like region" is a region of a protein characterized by certain combinations of the polypeptide backbone dihedral angles phi ($\phi$) and psi ($\psi$). Regions wherein $\phi$ is less than $-60°$ and $\psi$ is greater than $90°$ are beta-strand-like. Those skilled in the art will recognize that the limits of a $\beta$-strand are somewhat imprecise and may vary with the criteria used to define them. See, for example, Richardson and Richardson in Fasman, ed., Prediction of Protein Structure and the Principles of Protein Conformation, Plenum Press, New York, 1989; and Lesk, *Protein Architecture: A Practical Approach,* Oxford University Press, New York, 1991.

A "complement" of a polynucleotide molecule is a polynucleotide molecule having a complementary base sequence and reverse orientation as compared to a reference sequence. For example, the sequence 5' ATGCACGGG 3' is complementary to 5° CCCGTGCAT 3'.

A plurality of polypeptide chains are "complexed with" each other when they are associated, covalently (e.g., by disulfide bonding) or non-covalently (e.g., by hydrogen bonding, hydrophobic interactions, or salt-bridge interactions), to form a protein having a characteristic biological activity.

"Corresponding to", when used in reference to a nucleotide or amino acid sequence, indicates the position in a second sequence that aligns with the reference position when two sequences are optimally aligned.

The term "degenerate nucleotide sequence" denotes a sequence of nucleotides that includes one or more degenerate codons (as compared to a reference polynucleotide molecule that encodes a polypeptide). Degenerate codons contain different triplets of nucleotides, but encode the same amino acid residue (i.e., GAU and GAC triplets each encode Asp).

The term "expression vector" is used to denote a DNA molecule, linear or circular, that comprises a segment encoding a polypeptide of interest operably linked to additional segments that provide for its transcription. Such additional segments include promoter and terminator sequences, and may also include one or more origins of replication, one or more selectable markers, an enhancer, a polyadenylation signal, etc. Expression vectors are generally derived from plasmid or viral DNA, or may contain elements of both.

The term "isolated", when applied to a polynucleotide, denotes that the polynucleotide has been removed from its natural genetic milieu and is thus free of other extraneous or unwanted coding sequences, and is in a form suitable for use within genetically engineered protein production systems. Such isolated molecules are those that are separated from their natural environment and include cDNA and genomic clones. Isolated DNA molecules of the present invention are free of other genes with which they are ordinarily associated, but may include naturally occurring 5' and 3' untranslated regions such as promoters and terminators. The identification of associated regions will be evident to one of ordinary skill in the art (see for example, Dynan and Tijan, *Nature* 316:774–78, 1985).

An "isolated" polypeptide or protein is a polypeptide or protein that is found in a condition other than its native environment, such as apart from blood and animal tissue. In a preferred form, the isolated polypeptide or protein is substantially free of other polypeptides or proteins, particularly other polypeptides or proteins of animal origin. It is preferred to provide the polypeptides or proteins in a highly purified form, i.e. greater than 95% pure, more preferably greater than 99% pure. When used in this context, the term "isolated" does not exclude the presence of the same polypeptide or protein in alternative physical forms, such as dimers or alternatively glycosylated or derivatized forms.

"Operably linked", when referring to DNA segments, indicates that the segments are arranged so that they function in concert for their intended purposes, e.g., transcription initiates in the promoter and proceeds through the coding segment to the terminator.

The term "ortholog" denotes a polypeptide or protein obtained from one species that is the functional counterpart of a polypeptide or protein from a different species. Sequence differences among orthologs are the result of speciation.

A "polynucleotide" is a single- or double-stranded polymer of deoxyribonucleotide or ribonucleotide bases read from the 5' to the 3' end. Polynucleotides include RNA and DNA, and may be isolated from natural sources, synthesized in vitro, or prepared from a combination of natural and synthetic molecules. Sizes of polynucleotides are expressed as base pairs (abbreviated "bp"), nucleotides ("nt"), or kilobases ("kb"). Where the context allows, the latter two terms may describe polynucleotides that are single-stranded or double-stranded. When the term is applied to double-stranded molecules it is used to denote overall length and will be understood to be equivalent to the term "base pairs". It will be recognized by those skilled in the art that the two strands of a double-stranded polynucleotide may differ slightly in length and that the ends thereof may be staggered as a result of enzymatic cleavage; thus all nucleotides within a double-stranded polynucleotide molecule may not be paired. Such unpaired ends will in general not exceed 20 nt in length.

A "polypeptide" is a polymer of amino acid residues joined by peptide bonds, whether produced naturally or synthetically. Polypeptides of less than about 10 amino acid residues are commonly referred to as "peptides".

The term "promoter" is used herein for its art-recognized meaning to denote a portion of a gene containing DNA sequences that provide for the binding of RNA polymerase and initiation of transcription. Promoter sequences are commonly, but not always, found in the 5' non-coding regions of genes.

A "protein" is a macromolecule comprising one or more polypeptide chains. A protein may also comprise non-peptidic components, such as carbohydrate groups. Carbohydrates and other non-peptidic substituents may be added to a protein by the cell in which the protein is produced, and will vary with the type of cell. Proteins are defined herein in terms of their amino acid backbone structures; substituents such as carbohydrate groups are generally not specified, but may be present nonetheless.

A "secretory signal sequence" is a DNA sequence that encodes a polypeptide (a "secretory peptide") that, as a component of a larger polypeptide, directs the larger polypeptide through a secretory pathway of a cell in which it is synthesized. The larger polypeptide is commonly cleaved to remove the secretory peptide during transit through the secretory pathway.

Molecular weights and lengths of polymers determined by imprecise analytical methods (e.g., gel electrophoresis) will be understood to be approximate values. When such a value is expressed as "about" X or "approximately" X, the stated value of X will be understood to be accurate to ±10%.

All references cited herein are incorporated by reference in their entirety.

The present invention is based in part upon the discovery of a novel DNA molecule that encodes a polypeptide having a secretory peptide and an arrangement of cysteine residues and beta strand-like regions that is characteristic of the gonadotropin family of glycoprotein hormones. The DNA molecule was originally identified in a library of cDNAs derived from pancreatic islet cells. Northern blot analysis of the tissue distribution of the mRNA corresponding to this novel DNA showed that expression was highest in pancreas, with lower expression levels in pituitary, testis, and eye. The polypeptide has been designated "zsig51".

Analysis of the zsig51 sequence indicates that the polypeptide can form homomultimers or heteromultimers that could modulate cell proliferation, differentiation, or metabolism. Members of this family of proteins regulate organ development and regeneration, post-developmental organ growth, and organ maintenance.

SEQ ID NO:2 is the sequence of a representative polypeptide of the present invention. Analysis of the amino acid sequence indicates that residues −23 through −1 form a secretory peptide, with the mature polypeptide beginning at residue 1 (Gln) and continuing through residue 106 (Tyr). SEQ ID NO:2 shows significant homology to the gonadotropin and Norrie disease subfamilies of C-terminal cystine knot proteins. Sequence alignment shows conservation of Cys residues at positions 8, 25, 34, 38, 65, 66, 80, 96, 98, and 101, with those at positions 8, 34, 38, 66, 96, and 98 being most highly conserved within the family. Further analysis suggests pairing (disulfide bond formation) of Cys residues 8 and 66, 34 and 96, and 38 and 98 to form the cystine knot. The Cys residues at positions 25, 65, 80, and 101 may form intramolecular or intermolecular disulfide bonds. The Gly residue at position 36 is also highly conserved. This arrangement of conserved residues can be represented by the formula Cys-$Xaa_{25-33}$-Cys-Xaa-Gly-Xaa-Cys-$Xaa_{15-33}$-Cys-$Xaa_{20-33}$-Cys-Xaa-Cys (SEQ ID NO:3), wherein each Xaa is any amino acid and the subscripts designate the number of residues. Consensus carbohydrate addition sites are at residues 14–17 and 58— 61.

Higher order structure of zsig51 polypeptides can be predicted by computer analysis using available software (e.g., the Insight II viewer and Homology Modeling Tools; Molecular Simulations, Inc., San Diego, Calif.). Analysis of SEQ ID NO:2 predicts that the secondary structure is dominated by the cystine knot, which ties together variable beta strand-like regions and loops into a bow tie-like structure. The approximate boundaries of the beta strand-like regions are: strand 1, residues 9–17; strand 2, residues 29–34; strand 3, residues 38–43; strand 4, residues 59–64; strand 5, residues 67–71; strand 6, residues 90–95. The bow tie structure is formed as: amino terminus to cystine knot→beta strand 1→variable loop 1→beta strand 2→cystine knot→beta strand 3→variable loop 2→beta strand 4→cystine knot→beta strand 5→variable loop 3→beta strand 6→cystine knot. Variable loop 1 is disulfide bonded to variable loop 2 to form one side of the bow tie, with variable loop 3 forming the other side.

Structural analysis and homology indicate that zsig51 polypeptides complex with a second polypeptide to form multimeric proteins. These proteins include homodimers and heterodimers. In the latter case, the second polypeptide can be a truncated or other variant zsig51 polypeptide or another polypeptide, such as a glycoprotein hormone subunit, TGF-β polypeptide, a GDF polypeptide, or a bone morphogenic protein (BMP) polypeptide. Among the dimeric proteins within the present invention are dimers formed by non-covalent association (e.g., hydrophobic interactions) with a second subunit, either a second zsig51 polypeptide or other second subunit, such as a common α subunit. Within these dimers, loops 1 and 3 of monomer 1 interact with loop 2 of monomer 2, and loop 2 of monomer 1 interacts with loops 1 and 3 of monomer 2. In addition, dimerization may occur via intermolecular disulfide bond formation. Alignment with TGF-β indicates that Cys-65 may participate in an intermolecular disulfide bond.

The present invention also provides isolated polypeptides that are substantially homologous to the polypeptides of SEQ ID NO:2 and their orthologs. Such polypeptides will preferably be at least 95% or more identical to residues 1–106 of SEQ ID NO:2 or its orthologs. Percent sequence identity is determined by conventional methods. See, for example, Altschul et al., *Bull. Math. Bio.* 48:603–616, 1986, and Henikoff and Henikoff, *Proc. Natl. Acad. Sci. USA* 89:10915–10919, 1992. Briefly, two amino acid sequences are aligned to optimize the alignment scores using a gap opening penalty of 10, a gap extension penalty of 1, and the "BLOSUM62" scoring matrix of Henikoff and Henikoff (ibid.) as shown in Table 1 (amino acids are indicated by the standard one-letter codes). The percent identity is then calculated as:

$$\frac{\text{Total number of identical matches}}{[\text{length of the longer sequence plus the number of gaps introduced into the longer sequence in order to align the two sequences}]} \times 100$$

The level of identity between amino acid sequences can be determined using the "FASTA" similarity search algorithm of Pearson and Lipman (*Proc. Natl. Acad. Sci. USA* 85:2444, 1988), and by Pearson (*Meth. Enzymol.* 183:63, 1990). Briefly, FASTA first characterizes sequence similarity by identifying regions shared by the query sequence (e.g., SEQ ID NO:2) and a test sequence that have either the highest density of identities (if the ktup variable is 1) or pairs of identities (if ktup=2), without considering conservative amino acid substitutions, insertions, or deletions. The ten regions with the highest density of identities are then rescored by comparing the similarity of all paired amino acids using an amino acid substitution matrix, and the ends of the regions are "trimmed" to include only those residues that contribute to the highest score. If there are several regions with scores greater than the "cutoff" value (calculated by a predetermined formula based upon the length of the sequence and the ktup value), then the trimmed initial regions are examined to determine whether the regions can be joined to form an approximate alignment with gaps. Finally, the highest scoring regions of the two amino acid sequences are aligned using a modification of the Needleman-Wunsch-Sellers algorithm (Needleman and Wunsch, *J. Mol. Biol.* 48:444, 1970; Sellers, *SIAM J. Appl. Math.* 26:787, 1974), which allows for amino acid insertions and deletions. Illustrative parameters for FASTA analysis are: ktup=1, gap opening penalty=10, gap extension penalty=1, and substitution matrix=BLOSUM62. These parameters can be introduced into a FASTA program by modifying the scoring matrix file ("SMATRIX"), as explained in Appendix 2 of Pearson, 1990 (ibid.).

FASTA can also be used to determine the sequence identity of nucleic acid molecules using a ratio as disclosed above. For nucleotide sequence comparisons, the ktup value can range between one to six, preferably from four to six.

The present invention includes polypeptides having one or more conservative amino acid changes as compared with the amino acid sequence of SEQ ID NO:2. The BLOSUM62 matrix (Table 1) is an amino acid substitution matrix derived from about 2,000 local multiple alignments of protein sequence segments, representing highly conserved regions of more than 500 groups of related proteins (Henikoff and Henikoff, ibid.). Thus, the BLOSUM62 substitution frequencies can be used to define conservative amino acid substitutions that may be introduced into the amino acid sequences of the present invention. As used herein, the term "conservative amino acid substitution" refers to a substitution represented by a BLOSUM62 value of greater than −1. For example, an amino acid substitution is conservative if the substitution is characterized by a BLOSUM62 value of 0, 1, 2, or 3. Preferred conservative amino acid substitutions are characterized by a BLOSUM62 value of at least one 1 (e.g., 1, 2 or 3), while more preferred conservative amino acid substitutions are characterized by a BLOSUM62 value of at least 2 (e.g., 2 or 3).

Substantially homologous proteins and polypeptides are characterized as having one or more amino acid substitutions, deletions or additions. These changes are preferably of a minor nature, that is conservative amino acid substitutions and other changes that do not significantly affect the folding or activity of the protein or polypeptide, and include amino- or carboxyl-terminal extensions, such as an amino-terminal methionine residue, a small linker peptide of up to about 20–25 residues, or an extension that facilitates purification (an affinity tag) as disclosed above. Proteins having such an extension will preferably comprise a region that is at least 95% identical to residues 1 through 106 of SEQ ID NO:2, or an ortholog thereof.

The present invention further provides a variety of other polypeptide fusions and related multimeric proteins comprising one or more polypeptide fusions. For example, a zsig51 polypeptide can be prepared as a fusion to a dimer-

TABLE 1

|   | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 4 | | | | | | | | | | | | | | | | | | | |
| R | -1 | 5 | | | | | | | | | | | | | | | | | | |
| N | -2 | 0 | 6 | | | | | | | | | | | | | | | | | |
| D | -2 | -2 | 1 | 6 | | | | | | | | | | | | | | | | |
| C | 0 | -3 | -3 | -3 | 9 | | | | | | | | | | | | | | | |
| Q | -1 | 1 | 0 | 0 | -3 | 5 | | | | | | | | | | | | | | |
| E | -1 | 0 | 0 | 2 | -4 | 2 | 5 | | | | | | | | | | | | | |
| G | 0 | -2 | 0 | -1 | -3 | -2 | -2 | 6 | | | | | | | | | | | | |
| H | -2 | 0 | 1 | -1 | -3 | 0 | 0 | -2 | 8 | | | | | | | | | | | |
| I | -1 | -3 | -3 | -3 | -1 | -3 | -3 | -4 | -3 | 4 | | | | | | | | | | |
| L | -1 | -2 | -3 | -4 | -1 | -2 | -3 | -4 | -3 | 2 | 4 | | | | | | | | | |
| K | -1 | 2 | 0 | -1 | -3 | 1 | 1 | -2 | -1 | -3 | -2 | 5 | | | | | | | | |
| M | -1 | -1 | -2 | -3 | -1 | 0 | -2 | -3 | -2 | 1 | 2 | -1 | 5 | | | | | | | |
| F | -2 | -3 | -3 | -3 | -2 | -3 | -3 | -3 | -1 | 0 | 0 | -3 | 0 | 6 | | | | | | |
| P | -1 | -2 | -2 | -1 | -3 | -1 | -1 | -2 | -2 | -3 | -3 | -1 | -2 | -4 | 7 | | | | | |
| S | 1 | -1 | 1 | 0 | -1 | 0 | 0 | 0 | -1 | -2 | -2 | 0 | -1 | -2 | -1 | 4 | | | | |
| T | 0 | -1 | 0 | -1 | -1 | -1 | -1 | -2 | -2 | -1 | -1 | -1 | -1 | -2 | -1 | 1 | 5 | | | |
| W | -3 | -3 | -4 | -4 | -2 | -2 | -3 | -2 | -2 | -3 | -2 | -3 | -1 | 1 | -4 | -3 | -2 | 11 | | |
| Y | -2 | -2 | -2 | -3 | -2 | -1 | -2 | -3 | 2 | -1 | -1 | -2 | -1 | 3 | -3 | -2 | -2 | 2 | 7 | |
| V | 0 | -3 | -3 | -3 | -1 | -2 | -2 | -3 | -3 | 3 | 1 | -2 | 1 | -1 | -2 | -2 | 0 | -3 | -1 | 4 | izing protein as disclosed in U.S. Pat. Nos. 5,155,027 and 5,567,584. Preferred dimerizing proteins in this regard include immunoglobulin constant region domains. Immunoglobulin-zsig51 polypeptide fusions can be expressed in genetically engineered cells to produce a variety of multimeric zsig51 analogs. Auxiliary domains can be fused to zsig51 polypeptides to target them to specific cells, tissues, or macromolecules (e.g., collagen). For example, a zsig51 polypeptide or protein can be targeted to a predetermined cell type by fusing a zsig51 polypeptide to a ligand that specifically binds to a receptor on the surface of the target cell. In this way, polypeptides and proteins can be targeted for therapeutic or diagnostic purposes. A zsig51 polypeptide can be fused to two or more moieties, such as an affinity tag for purification and a targeting domain. Polypeptide fusions can also comprise one or more cleavage sites, particularly between domains. See, Tuan et al., *Connective Tissue Research* 34:1–9, 1996.

The polypeptides of the present invention can also comprise non-naturally occurring amino acid residues. Non-naturally occurring amino acids include, without limitation, trans-3-methylproline, 2,4-methanoproline, cis-4-hydroxyproline, trans-4-hydroxyproline, N-methylglycine, allo-threonine, methylthreonine, hydroxyethylcysteine, hydroxyethylhomocysteine, nitroglutamine, homoglutamine, pipecolic acid, tert-leucine, norvaline, 2-azaphenylalanine, 3-azaphenylalanine, 4-azaphenylalanine, and 4-fluorophenylalanine. Several methods are known in the art for incorporating non-naturally occurring amino acid residues into proteins. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations is carried out in a cell-free system comprising an *E. coli* S30 extract and commercially available enzymes and other reagents. Proteins are purified by chromatography. See, for example, Robertson et al., *J. Am. Chem. Soc.* 113:2722, 1991; Ellman et al., *Methods Enzymol.* 202:301, 1991; Chung et al., *Science* 259:806–809, 1993; and Chung et al., *Proc. Natl. Acad. Sci. USA* 90:10145–10149, 1993). In a second method, translation is carried out in Xenopus oocytes by microinjection of mutated mRNA and chemically aminoacylated suppressor tRNAs (Turcatti et al., *J. Biol. Chem.* 271:19991–19998, 1996). Within a third method, *E. coli* cells are cultured in the absence of a natural amino acid that is to be replaced (e.g., phenylalanine) and in the presence of the desired non-naturally occurring amino acid(s) (e.g., 2-azaphenylalanine, 3-azaphenylalanine, 4-azaphenylalanine, or 4-fluorophenylalanine). The non-naturally occurring amino acid is incorporated into the protein in place of its natural counterpart. See, Koide et al., *Biochem.* 33:7470–7476, 1994. Naturally occurring amino acid residues can be converted to non-naturally occurring species by in vitro chemical modification. Chemical modification can be combined with site-directed mutagenesis to further expand the range of substitutions (Wynn and Richards, *Protein Sci.* 2:395–403, 1993).

Amino acid sequence changes are made in zsig51 polypeptides so as to minimize disruption of higher order structure essential to biological activity. Changes in amino acid residues will be made so as not to disrupt the cystine knot and "bow tie" arrangement of loops that is characteristic of the protein family. The effects of amino acid sequence changes can be predicted by computer modeling as disclosed above or determined by analysis of crystal structure (see, e.g., Lapthorn et al., ibid.). A hydrophobicity profile of SEQ ID NO:2 is shown in the attached figure. Those skilled in the art will recognize that this hydrophobicity will be taken into account when designing alterations in the amino acid sequence of a zsig51 polypeptide, so as not to disrupt the overall profile. Alignment of zsig51 with other family members also provides guidance in selecting amino acid substitutions, particularly if information about the effects of amino acid substitutions in other family members is available. For example, alignment suggests that residue 95 (Ala) can be replaced with Ser. This variant sequence is shown in SEQ ID NO:29. Alignment with NDP, taking into account reported deleterious mutations, indicates that residues 8, 11, 12, 14, 29, 30, 32, 34, 43, 44, 60, 63, 64, 65, 71, 74, 75, 80, 90, 91, 93, and 94 may be relatively intolerant of substitution or deletion. Residue 75 (Lys in SEQ ID NO:2) may be conservatively replaced with Arg. The region of zsig51 from the penultimate Cys residue to the carboxyl terminus (residues 98 to 106 of SEQ ID NO:2) may be important for receptor specificity.

Essential amino acids in the polypeptides of the present invention can be identified according to procedures known in the art, such as site-directed mutagenesis or alanine-scanning mutagenesis (Cunningham and Wells, *Science* 244, 1081–1085, 1989; Bass et al., *Proc. Natl. Acad. Sci. USA* 88:4498–4502, 1991). In the latter technique, single alanine mutations are introduced at every residue in the molecule, and the resultant mutant molecules are tested for biological activity of other properties to identify amino acid residues that are critical to the activity of the molecule.

Multiple amino acid substitutions can be made and tested using known methods of mutagenesis and screening, such as those disclosed by Reidhaar-Olson and Sauer (*Science* 241:53–57, 1988) or Bowie and Sauer (*Proc. Natl. Acad. Sci. USA* 86:2152–2156, 1989). Briefly, these authors disclose methods for simultaneously randomizing two or more positions in a polypeptide, selecting for functional polypeptide, and then sequencing the mutagenized polypeptides to determine the spectrum of allowable substitutions at each position. Other methods that can be used include phage display (e.g., Lowman et al., *Biochem.* 30:10832–10837, 1991; Ladner et al., U.S. Pat. No. 5,223,409; Huse, WIPO Publication WO 92/06204) and region-directed mutagenesis (Derbyshire et al., *Gene* 46:145, 1986; Ner et al., *DNA* 7:127, 1988).

Variants of the disclosed zsig51 DNA and polypeptide sequences can be generated through DNA shuffling as disclosed by Stemmer, *Nature* 370:389–391, 1994 and Stemmer, *Proc. Natl. Acad. Sci. USA* 91:10747–10751, 1994. Briefly, variant genes are generated by in vitro homologous recombination by random fragmentation of a parent gene followed by reassembly using PCR, resulting in randomly introduced point mutations. This technique can be modified by using a family of parent genes, such as allelic variants or genes from different species, to introduce additional variability into the process. Selection or screening for the desired activity, followed by additional iterations of mutagenesis and assay provides for rapid "evolution" of sequences by selecting for desirable mutations while simultaneously selecting against detrimental changes.

Mutagenesis methods as disclosed above can be combined with high volume or high-throughput screening methods to detect biological activity of zsig51 variant polypeptides, in particular biological activity in modulating cell proliferation or cell differentiation. For example, mitogenesis assays that measure dye incorporation or $^3$H-thymidine incorporation can be carried out on large numbers of samples, as can cell-based assays that detect expression of a reporter gene (e.g., a luciferase gene). These and other assays are disclosed in more detail below. Mutagenized DNA molecules that encode active zsig51 polypeptides can be recovered from the host cells and rapidly sequenced using modern equipment. These methods allow the rapid determination of the importance of individual amino acid residues in a polypeptide of interest, and can be applied to polypeptides of unknown structure.

Using the methods discussed above, one of ordinary skill in the art can identify and/or prepare a variety of polypeptides that are substantially homologous to residues 1 through 106 of SEQ ID NO: 2 or allelic variants or orthologs thereof and retain the biological properties of the wild-type protein. Such polypeptides can also include additional polypeptide segments as generally disclosed above.

The present invention also provides polynucleotide molecules, including DNA and RNA molecules, that encode the zsig51 polypeptides disclosed above. Those skilled in the art will readily recognize that, in view of the degeneracy of the genetic code, considerable sequence variation is possible among these polynucleotide molecules. SEQ ID NO:4 is a degenerate DNA sequence that encompasses all DNAs that encode the zsig51 polypeptide of SEQ ID NO: 2. Those skilled in the art will recognize that the degenerate sequence of SEQ ID NO:4 also provides all RNA sequences encoding SEQ ID NO:2 by substituting U for T. Thus, zsig51 polypeptide-encoding polynucleotides comprising nucleotide 70 to nucleotide 387 of SEQ ID NO: 4 and their RNA equivalents are contemplated by the present invention. A degenerate sequence encoding SEQ ID NO:29 is shown in SEQ ID NO:30. Table 2 sets forth the one-letter codes used within SEQ ID NO:4 and SEQ ID NO:30 to denote degenerate nucleotide positions. "Resolutions" are the nucleotides denoted by a code letter. "Complement" indicates the code for the complementary nucleotide(s). For example, the code Y denotes either C or T, and its complement R denotes A or G, A being complementary to T, and G being complementary to C.

TABLE 2

| Nucleotide | Resolutions | Complement | Resolutions |
|---|---|---|---|
| A | A | T | T |
| C | C | G | G |
| G | G | C | C |
| T | T | A | A |
| R | A\|G | Y | C\|T |
| Y | C\|T | R | A\|G |
| M | A\|C | K | G\|T |
| K | G\|T | M | A\|C |
| S | C\|G | S | C\|G |
| W | A\|T | W | A\|T |
| H | A\|C\|T | D | A\|G\|T |
| B | C\|G\|T | V | A\|C\|G |
| V | A\|C\|G | B | C\|G\|T |
| D | A\|G\|T | H | A\|C\|T |
| N | A\|C\|G\|T | N | A\|C\|G\|T |

The degenerate codons used in SEQ ID NO:4 and SEQ ID NO:30, encompassing all possible codons for a given amino acid, are set forth in Table 3, below.

TABLE 3

| Amino Acid | One-Letter Code | Codons | Degenerate Codon |
|---|---|---|---|
| Cys | C | TGC TGT | TGY |
| Ser | S | AGC AGT TCA TCC TCG TCT | WSN |
| Thr | T | ACA ACC ACG ACT | CAN |
| Pro | P | CCA CCC CCG CCT | CCN |
| Ala | A | GCA GCC GCG GCT | GCN |
| Gly | G | GGA GGC GGG GGT | GGN |
| Asn | N | AAC AAT | AAY |
| Asp | D | GAC GAT | GAY |
| Glu | E | GAA GAG | GAR |
| Gln | Q | CAA CAG | CAR |
| His | H | CAC CAT | CAY |
| Arg | R | AGA AGG CGA CGC CGG CGT | MGN |
| Lys | K | AAA AAG | AAR |
| Met | M | ATG | ATG |
| Ile | I | ATA ATC ATT | ATH |
| Leu | L | CTA CTC CTG CTT TTA TTG | YTN |
| Val | V | GTA GTC GTG GTT | GTN |
| Phe | F | TTC TTT | TTY |
| Tyr | Y | TAC TAT | TAY |
| Trp | W | TGG | TGG |
| Ter | . | TAA TAG TGA | TRR |
| Asn\|Asp | B |  | RAY |
| Glu\|Gln | Z |  | SAR |
| Any | X |  | NNN |
| Gap | — | - - - |  |

One of ordinary skill in the art will appreciate that some ambiguity is introduced in determining a degenerate codon, representative of all possible codons encoding each amino acid. For example, the degenerate codon for serine (WSN) can, in some circumstances, encode arginine (AGR), and the degenerate codon for arginine (MGN) can, in some circumstances, encode serine (AGY). A similar relationship exists between codons encoding phenylalanine and leucine. Thus, some polynucleotides encompassed by the degenerate sequences may encode variant amino acid sequences, but one of ordinary skill in the art can easily identify such variant sequences by reference to the amino acid sequence of SEQ ID NO: 2 or SEQ ID NO:29. Variant sequences can be readily tested for functionality as described herein.

For any zsig51 polypeptide, including variants and fusion proteins, one of ordinary skill in the art can readily generate a fully degenerate polynucleotide sequence encoding that variant using the information set forth in Tables 2 and 3 above. Moreover, those of skill in the art can use standard software to devise zsig51 variants based upon the nucleotide and amino acid sequences described herein. The present invention thus provides a computer-readable medium encoded with a data structure that provides at least one of the following sequences: SEQ ID NO:1, SEQ ID NO:2, SEQ ID NO:3, SEQ ID NO:4, SEQ ID NO:29, SEQ ID NO:30, SEQ ID NO:31, SEQ ID NO:32, SEQ ID NO:38, and SEQ ID NO:39. Suitable forms of computer-readable media include magnetic media and optically-readable media. Examples of magnetic media include a hard or fixed drive, a random access memory (RAM) chip, a floppy disk, digital linear tape (DLT), a disk cache, and a ZIP disk. Optically readable media are exemplified by compact discs (e.g., CD-read only memory (ROM), CD-rewritable (RW), and CD-recordable), and digital versatile/video discs (DVD) (e.g., DVD-ROM, DVD-RAM, and DVD+RW).

Within preferred embodiments of the invention the isolated polynucleotides will hybridize to similar sized regions of SEQ ID NO:1, or a sequence complementary thereto, under stringent conditions. In general, stringent conditions are selected to be about 5° C. lower than the thermal melting point (T$_m$) for the specific sequence at a defined ionic strength and pH. The T$_m$ is the temperature (under defined ionic strength and pH) at which 50% of the target sequence hybridizes to a perfectly matched probe. Typical stringent conditions are those in which the salt concentration is up to about 0.03 M at pH 7 and the temperature is at least about 60° C.

As previously noted, the isolated polynucleotides of the present invention include DNA and RNA. Methods for preparing DNA and RNA are well known in the art. Complementary DNA (cDNA) clones are prepared from RNA that is isolated from a tissue or cell that produces large amounts of zsig51 RNA. Such tissues and cells are identified by Northern blotting (Thomas, *Proc. Natl. Acad. Sci. USA* 77:5201, 1980), and include pancreas, pituitary, testis, and eye. Total RNA can be prepared using guanidine HCl extraction followed by isolation by centrifugation in a CsCl gradient (Chirgwin et al., *Biochemistry* 18:52–94, 1979). Poly (A)$^+$ RNA is prepared from total RNA using the method of Aviv and Leder (*Proc. Natl. Acad. Sci. USA* 69:1408–1412, 1972). Complementary DNA (cDNA) is prepared from poly(A)$^+$ RNA using known methods. In the alternative, genomic DNA can be isolated. For some applications (e.g., expression in transgenic animals) it may be preferable to use a genomic clone, or to modify a cDNA clone to include at least one genomic intron. Methods for identifying and isolating cDNA and genomic clones are well known and within the level of ordinary skill in the art, and include the use of the sequence disclosed herein, or parts thereof, for probing or priming a library. Polynucleotides encoding zsig51 polypeptides are identified and isolated by, for example, hybridization or polymerase chain reaction ("PCR", Mullis, U.S. Pat. No. 4,683,202). Expression libraries can be probed with antibodies to zsig51, receptor fragments, or other specific binding partners.

Those skilled in the art will recognize that the sequences disclosed in SEQ ID NOS:1 and 2 represent a single allele of human zsig51. Allelic variants of these sequences can be cloned by probing cDNA or genomic libraries from different individuals according to standard procedures.

The present invention further provides counterpart polynucleotides and polypeptides from other species (orthologs). Of particular interest are zsig51 polynucleotides and polypeptides from other mammalian species, including murine, rat, porcine, ovine, bovine, canine, feline, equine and other primate proteins. Orthologs of the human polynucleotides can be cloned using information and compositions provided by the present invention in combination with conventional cloning techniques. For example, a cDNA can be cloned using mRNA obtained from a tissue or cell type that expresses the protein. Suitable sources of mRNA can be identified by probing Northern blots with probes designed from the sequences disclosed herein. A library is then prepared from mRNA of a positive tissue or cell line. A zsig51-encoding cDNA can then be isolated by a variety of methods, such as by probing with a complete or partial human cDNA or with one or more sets of degenerate probes based on the disclosed sequences. A cDNA can also be cloned by PCR using primers designed from the sequences disclosed herein. Within an additional method, the cDNA library can be used to transform or transfect host cells, and expression of the cDNA of interest can be detected with an antibody to zsig51 polypeptide. Similar techniques can also be applied to the isolation of genomic clones.

Conserved regions of zsig51, identified by alignment with sequences of other family members (including Norrie disease protein, human gonadotropin beta and alpha subunits, TGF-β1, myostatin, and leutropin) can be used to identify related polynucleotides and proteins. For instance, reverse transcription-polymerase chain reaction (RT-PCR) and other techniques known in the art can be used to amplify sequences encoding the conserved motifs present in zsig51 from RNA obtained from a variety of tissue sources. In particular, highly degenerate primers as shown below in Table 4 are useful for this purpose. Primers derived from sequence encoding residues 33–38 (SEQ ID NOS:5, 6, and 7) and 94–99 of SEQ ID NO:2 are preferred for wide family screening, while primers derived from sequence encoding residues 96–101, 33–38 (SEQ ID NOS:14, 15 and 16), 63–68, and 11–16 are preferred for use in identifying more closely related homologs.

TABLE 4 zsig51 residues 33–38

| | |
|---|---|
| degenerate: | CN TGY GTN GGN CAY TGY (SEQ ID NO:5) |
| consensus: | NN TGY DNN GGN BVN TGY (SEQ ID NO:6) |
| complement: | NN ACR HNN CCN VBN ACR (SEQ ID NO:7) | zsig51 residues 94–99

| | |
|---|---|
| degenerate: | MGN GCN TGY CAR TGY GA (SEQ ID NO:8) |
| consensus: | NNN NVN TGY VRN TGY DV (SEQ ID NO:9) |
| complement: | NNN NBN ACR BYN ACR HB (SEQ ID NO:10) | zsig51 residues 96–101

| | |
|---|---|
| degenerate: | TGY CAR TGY GAY ATG TG (SEQ ID NO:11) |
| consensus: | TGY CAN TGY GAN RWR TG (SEQ ID NO:12) |
| complement: | ACR GTN ACR CTN YWY AC (SEQ ID NO:13) | zsig51 residues 33–38

| | |
|---|---|
| degenerate: | CN TGY GTN GGN CAY TGY (SEQ ID NO:14) |
| consensus: | SN TGY GWN GGN CAY TGY (SEQ ID NO:15) |
| complement: | SN ACR CWN CCN GTR ACR (SEQ ID NO:16) | zsig51 residues 63–68

| | |
|---|---|
| degenerate: | WSN CAR TGY TGY ACN AT (SEQ ID NO:17) |
| consensus: | WSN CAN TGY TGY MSN MY (SEQ ID NO:18) |
| complement: | WSN GTN ACR ACR KSN KR (SEQ ID NO:19) | zsig51 residues 11–16

| | |
|---|---|
| degenerate: | CAY CCN TTY AAY GTN AC (SEQ ID NO:20) |
| consensus: | MRN CMN YWY WAY GTN RM (SEQ ID NO:21) |
| complement: | KYN GKN RWR WTR CAN YK (SEQ ID NO:22) |

Zsig51 polynucleotide sequences disclosed herein can also be used as probes or primers to clone 5' non-coding regions of a zsig51 gene. In view of the tissue-specific expression observed for zsig51 by
Northern blotting, this gene region is expected to provide for pancreas-, testis-, eye-, and pituitary-specific expression. Promoter elements from a zsig51 gene could thus be used to direct the tissue-specific expression of heterologous genes in, for example, transgenic animals or patients treated with gene therapy. Cloning of 5' flanking sequences also facilitates production of zsig51 proteins by "gene activation" as disclosed in U.S. Pat. No. 5,641,670. Briefly, expression of an endogenous zsig51 gene in a cell is altered by introducing into the zsig51 locus a DNA construct comprising at least a targeting sequence, a regulatory sequence, an exon, and an unpaired splice donor site. The targeting sequence is a zsig51 5' non-coding sequence that permits homologous recombination of the construct with the endogenous zsig51 locus, whereby the sequences within the construct become operably linked with the endogenous zsig51 coding sequence. In this way, an endogenous zsig51 promoter can be replaced or supplemented with other regulatory sequences to provide enhanced, tissue-specific, or otherwise regulated expression.

The polynucleotides of the present invention can also be prepared by automated synthesis. Synthesis of polynucleotides is within the level of ordinary skill in the art, and suitable equipment and reagents are available from commercial suppliers. See, in general, Glick and Pasternak, *Molecular Biotechnology, Principles & Applications of Recombinant DNA*, ASM Press, Washington, D.C., 1994; Itakura et al., *Ann. Rev. Biochem.* 53: 323–56, 1984; and Climie et al., *Proc. Natl. Acad. Sci. USA* 87:633–7, 1990.

The polypeptides of the present invention, including full-length polypeptides, biologically active fragments, and fusion polypeptides can be produced in genetically engineered host cells according to conventional techniques. Suitable host cells are those cell types that can be transformed or transfected with exogenous DNA and grown in culture, and include bacteria, fungal cells, and cultured higher eukaryotic cells. Eukaryotic cells, particularly cultured cells of multicellular organisms, are preferred. Techniques for manipulating cloned DNA molecules and introducing exogenous DNA into a variety of host cells are disclosed by Sambrook et al., *Molecular Cloning: A Laboratory Manual*, 2nd ed., Cold Spring Harbor Laboratory Press, Cold Spring Harbor, N.Y., 1989, and Ausubel et al., eds., *Current Protocols in Molecular Biology*, Green and Wiley and Sons, NY, 1993.

In general, a DNA sequence encoding a zsig51 polypeptide is operably linked to other genetic elements required for its expression, generally including a transcription promoter and terminator, within an expression vector. The vector will also commonly contain one or more selectable markers and one or more origins of replication, although those skilled in the art will recognize that within certain systems selectable markers may be provided on separate vectors, and replication of the exogenous DNA may be provided by integration into the host cell genome. Selection of promoters, terminators, selectable markers, vectors and other elements is a matter of routine design within the level of ordinary skill in the art. Many such elements are described in the literature and are available through commercial suppliers.

To direct a zsig51 polypeptide into the secretory pathway of a host cell, a secretory signal sequence (also known as a leader sequence, prepro sequence or pre sequence) is provided in the expression vector. The secretory signal sequence may be that of zsig51, or may be derived from another secreted protein (e.g., t-PA; see U.S. Pat. No. 5,641,655) or synthesized de novo. The secretory signal sequence is operably linked to the zsig51 DNA sequence, i.e., the two sequences are joined in the correct reading frame and positioned to direct the newly synthesized polypeptide into the secretory pathway of the host cell. Secretory signal sequences are commonly positioned 5' to the DNA sequence encoding the polypeptide of interest, although certain signal sequences may be positioned elsewhere in the DNA sequence of interest (see, e.g., Welch et al., U.S. Pat. No. 5,037,743; Holland et al., U.S. Pat. No. 5,143,830).

Expression of zsig51 polypeptides via a host cell secretory pathway is expected to result in the production of multimeric proteins. As noted above, such multimers include both homomultimers and heteromultimers, the latter including proteins comprising only zsig51 polypeptides and proteins including zsig51 and heterologous polypeptides. For example, a heteromultimer comprising a zsig51 polypeptide and a common alpha subunit can be produced by co-expression of the two polypeptides in a host cell. A cDNA sequence encoding a common alpha subunit is disclosed by Fiddes and Goodman, *Nature* 281:351–356, 1979. A cDNA encoding the beta subunit of human chorionic gonadotropin is disclosed by Fiddes and Goodman, *Nature* 286:684–687, 1980. Berger et al., *Nature Genetics* 1:199–203, 1992 disclose cDNA clones encoding Norrie disease protein. A TGF-β cDNA is disclosed by Derynck et al., *Nature* 316:701–705, 1985. If a mixture of proteins results from expression, individual species are isolated by conventional methods. Monomers, dimers, and higher order multimers are separated by, for example, size exclusion chromatography. Heteromultimers can be separated from homomultimers by immunoaffinity chromatography using antibodies specific for individual dimers or by sequential immunoaffinity steps using antibodies specific for individual component polypeptides. See, in general, U.S. Pat. No. 5,094,941. Multimers may also be assembled in vitro upon incubation of component polypeptides under suitable conditions. Recovery and assembly of proteins expressed in bacterial cells is disclosed below.

Cultured mammalian cells are suitable hosts for use within the present invention. Methods for introducing exogenous DNA into mammalian host cells include calcium phosphate-mediated transfection (Wigler et al., *Cell* 14:725, 1978; Corsaro and Pearson, *Somatic Cell Genetics* 7:603, 1981: Graham and Van der Eb, *Virology* 52:456, 1973), electroporation (Neumann et al., *EMBO J.* 1:841–845, 1982), DEAE-dextran mediated transfection (Ausubel et al., ibid.), and liposome-mediated transfection (Hawley-Nelson et al., *Focus* 15:73, 1993; Ciccarone et al., *Focus* 15:80, 1993). The production of recombinant polypeptides in cultured mammalian cells is disclosed by, for example, Levinson et al., U.S. Pat. No. 4,713,339; Hagen et al., U.S. Pat. No. 4,784,950; Palmiter et al., U.S. Pat. No. 4,579,821; and Ringold, U.S. Pat. No. 4,656,134. Suitable cultured mammalian cells include the COS-1 (ATCC No. CRL 1650), COS-7 (ATCC No. CRL 1651), BHK (ATCC No. CRL 1632), BHK 570 (ATCC No. CRL 10314), 293 (ATCC No. CRL 1573; Graham et al., *J. Gen. Virol.* 36:59–72, 1977) and Chinese hamster ovary (e.g. CHO-K1; ATCC No. CCL 61) cell lines. Additional suitable cell lines are known in the art and available from public depositories such as the American Type Culture Collection, Rockville, Md. In general, strong transcription promoters are preferred, such as promoters from SV-40 or cytomegalovirus. See, e.g., U.S. Pat. No. 4,956,288. Other suitable promoters include those from metallothionein genes (U.S. Pat. Nos. 4,579,821 and 4,601, 978) and the adenovirus major late promoter. Within an alternative embodiment, adenovirus vectors can be employed. See, for example, Garnier et al., *Cytotechnol.* 15:145–55, 1994.

Drug selection is generally used to select for cultured mammalian cells into which foreign DNA has been inserted. Such cells are commonly referred to as "transfectants". Cells that have been cultured in the presence of the selective agent and are able to pass the gene of interest to their progeny are referred to as "stable transfectants." An exemplary selectable marker is a gene encoding resistance to the antibiotic neomycin. Selection is carried out in the presence of a neomycin-type drug, such as G-418 or the like. Selection systems can also be used to increase the expression level of the gene of interest, a process referred to as "amplification." Amplification is carried out by culturing transfectants in the presence of a low level of the selective agent and then increasing the amount of selective agent to select for cells that produce high levels of the products of the introduced genes. An exemplary amplifiable selectable marker is dihydrofolate reductase, which confers resistance to methotrexate. Other drug resistance genes (e.g. hygromycin resistance, multi-drug resistance, puromycin acetyltransferase) can also be used.

Other higher eukaryotic cells can also be used as hosts, including insect cells, plant cells and avian cells. The use of *Agrobacterium rhizogenes* as a vector for expressing genes in plant cells has been reviewed by Sinkar et al., *J. Biosci. (Bangalore)* 11:47–58, 1987. Transformation of insect cells and production of foreign polypeptides therein is disclosed by Guarino et al., U.S. Pat. No. 5,162,222 and WIPO publication WO 94/06463.

Insect cells can be infected with recombinant baculovirus, commonly derived from *Autographa californica* nuclear polyhedrosis virus (AcNPV). See, King and Possee, *The Baculovirus Expression System: A Laboratory Guide*, London, Chapman & Hall; O'Reilly et al., *Baculovirus Expression Vectors: A Laboratory Manual*, New York, Oxford University Press., 1994; and Richardson, Ed., *Baculovirus Expression Protocols. Methods in Molecular Biology*, Humana Press, Totowa, N.J., 1995. Recombinant baculovirus can also be produced through the use of a transposon-based system described by Luckow et al. (*J. Virol.* 67:4566–4579, 1993). This system, which utilizes transfer vectors, is commercially available in kit form (Bac-to-Bac™ kit; Life Technologies, Rockville, Md.). The transfer vector (e.g., pFastBac1™; Life Technologies) contains a Tn7 transposon to move the DNA encoding the protein of interest into a baculovirus genome maintained in *E. coli* as a large plasmid called a "bacmid." See, Hill-Perkins and Possee, *J. Gen. Virol.* 71:971–976, 1990; Bonning et al., *J. Gen. Virol.* 75:1551–1556, 1994; and Chazenbalk and Rapoport, *J. Biol. Chem.* 270:1543–1549, 1995. In addition, transfer vectors can include an in-frame fusion with DNA encoding a polypeptide extension or affinity tag as disclosed above. Using techniques known in the art, a transfer vector containing a zsig51-encoding sequence is transformed into *E. coli* host cells, and the cells are screened for bacmids which contain an interrupted lacZ gene indicative of recombinant baculovirus. The bacmid DNA containing the recombinant baculovirus genome is isolated, using common techniques, and used to transfect *Spodoptera frugiperda* cells, such as Sf9 cells. Recombinant virus that expresses zsig51 protein is subsequently produced. Recombinant viral stocks are made by methods commonly used the art.

For protein production, the recombinant virus is used to infect host cells, typically a cell line derived from the fall armyworm, *Spodoptera frugiperda* (e.g., Sf9 or Sf21 cells) or *Trichoplusia ni* (e.g., High Five™ cells; Invitrogen, Carlsbad, Calif.). See, in general, Glick and Pasternak, *Molecular Biotechnology: Principles and Applications of Recombinant DNA*, ASM Press, Washington, D.C., 1994. See also, U.S. Pat. No. 5,300,435. Serum-free media are used to grow and maintain the cells. Suitable media formulations are known in the art and can be obtained from commercial suppliers. The cells are grown up from an inoculation density of approximately $2-5 \times 10^5$ cells to a density of $1-2 \times 10^6$ cells, at which time a recombinant viral stock is added at a multiplicity of infection (MOI) of 0.1 to 10, more typically near 3. Procedures used are generally described in available laboratory manuals (e.g., King and Possee, ibid.; O'Reilly et al., ibid.; Richardson, ibid.).

Fungal cells, including yeast cells, can also be used within the present invention. Yeast species of particular interest in this regard include *Saccharomyces cerevisiae, Pichia pastoris,* and *Pichia methanolica*. Methods for transforming *S. cerevisiae* cells with exogenous DNA and producing recombinant polypeptides therefrom are disclosed by, for example, Kawasaki, U.S. Pat. No. 4,599,311; Kawasaki et al., U.S. Pat. No. 4,931,373; Brake, U.S. Pat. No. 4,870,008; Welch et al., U.S. Pat. No. 5,037,743; and Murray et al., U.S. Pat. No. 4,845,075. Transformed cells are selected by phenotype determined by the selectable marker, commonly drug resistance or the ability to grow in the absence of a particular nutrient (e.g., leucine). A preferred vector system for use in *Saccharomyces cerevisiae* is the POT1 vector system disclosed by Kawasaki et al. (U.S. Pat. No. 4,931,373), which allows transformed cells to be selected by growth in glucose-containing media. Suitable promoters and terminators for use in yeast include those from glycolytic enzyme genes (see, e.g., Kawasaki, U.S. Pat. No. 4,599,311; Kingsman et al., U.S. Pat. No. 4,615,974; and Bitter, U.S. Pat. No. 4,977,092) and alcohol dehydrogenase genes. See also U.S. Pat. Nos. 4,990,446; 5,063,154; 5,139,936 and 4,661,454. Transformation systems for other yeasts, including *Hansenula polymorpha, Schizosaccharomyces pombe, Kluyveromyces lactis, Kluyveromyces fragilis, Ustilago maydis, Pichia pastoris, Pichia methanolica, Pichia guillermondii* and *Candida maltosa* are known in the art. See, for example, Gleeson et al., *J. Gen. Microbiol.* 132:3459–3465, 1986 and Cregg, U.S. Pat. No. 4,882,279. Aspergillus cells may be utilized according to the methods of McKnight et al., U.S. Pat. No. 4,935,349. Methods for transforming *Acremonium chrysogenum* are disclosed by Sumino et al., U.S. Pat. No. 5,162,228. Methods for transforming Neurospora are disclosed by Lambowitz, U.S. Pat. No. 4,486,533.

The use of *Pichia methanolica* as host for the production of recombinant proteins is disclosed in U.S. Pat. Nos. 5,716,808 and 5,736,383, and WIPO Publications WO 97/17450 and WO 97/17451. DNA molecules for use in transforming *P. methanolica* will commonly be prepared as double-stranded, circular plasmids, which are preferably linearized prior to transformation. For polypeptide production in *P. methanolica,* it is preferred that the promoter and terminator in the plasmid be that of a *P. methanolica* gene. A preferred promoter is that of a *P. methanolica* alcohol utilization gene (AUG1). *P. methanolica* contains a second alcohol utilization gene, AUG2, the promoter of which can also be used. Other useful promoters include those of the dihydroxyacetone synthase (DHAS), formate dehydrogenase (FMD), and catalase (CAT) genes. To facilitate integration of the DNA into the host chromosome, it is preferred to have the entire expression segment of the plasmid flanked at both ends by host DNA sequences. This is conveniently accomplished by including 3' untranslated DNA sequence at the downstream end of the expression segment and relying on the promoter sequence at the 5' end. When using linear DNA, the expression segment will be flanked by cleavage sites to allow for linearization of the molecule and separation of the expression segment from other sequences (e.g., a bacterial origin of replication and selectable marker). Preferred such cleavage sites are those that are recognized by restriction endonucleases that cut infrequently within a DNA sequence, such as those that recognize 8-base target sequences (e.g., Not I). A preferred selectable marker for use in *Pichia methanolica* is a *P. methanolica* ADE2 gene, which encodes phosphoribosyl-5-aminoimidazole carboxylase (AIRC; EC 4.1.1.21). The ADE2 gene, when transformed into an ade2 host cell, allows the cell to grow in the absence of adenine. Other nutritional markers that can be used include the *P. methanolica* ADE1, HIS3, and LEU2 genes, which allow for selection in the absence of adenine, histidine, and leucine, respectively. For large-scale, industrial processes where it is desirable to minimize the use of methanol, it is preferred to use host cells in which both methanol utilization genes (AUG1 and AUG2) are deleted. For production of secreted proteins, host cells deficient in vacuolar protease genes (PEP4 and PRB1) are preferred.

Gene-deficient mutants can be prepared by known methods, such as site-directed mutagenesis. *P. methanolica* genes can be cloned on the basis of homology with their counterpart *Saccharomyces cerevisiae* genes. A preferred method of transforming *P. methanolica* is by electroporation as disclosed in U.S. Pat. No. 5,854,039.

Prokaryotic host cells, including strains of the bacteria *Escherichia coli*, Bacillus and other genera are also useful host cells within the present invention. Techniques for transforming these hosts and expressing foreign DNA sequences cloned therein are well known in the art (see, e.g., Sambrook et al., ibid.). When expressing a zsig51 polypeptide in bacteria such as *E. coli*, the polypeptide may be retained in the cytoplasm, typically as insoluble granules, or may be directed to the periplasmic space by a bacterial secretion sequence. In the former case, the cells are lysed, and the granules are recovered and denatured using, for example, guanidine isothiocyanate or urea. The denatured polypeptide can then be refolded and dimerized by diluting the denaturant, such as by dialysis against a solution of urea and a combination of reduced and oxidized glutathione, followed by dialysis against a buffered saline solution. In the latter case, the polypeptide can be recovered from the periplasmic space in a soluble and functional form by disrupting the cells (by, for example, sonication or osmotic shock) to release the contents of the periplasmic space and recovering the protein, thereby obviating the need for denaturation and refolding.

Transformed or transfected host cells are cultured according to conventional procedures in a culture medium containing nutrients and other components required for the growth of the chosen host cells. A variety of suitable media, including defined media and complex media, are known in the art and generally include a carbon source, a nitrogen source, essential amino acids, vitamins and minerals. Media may also contain such components as growth factors or serum, as required. The growth medium will generally select for cells containing the exogenously added DNA by, for example, drug selection or deficiency in an essential nutrient which is complemented by the selectable marker carried on the expression vector or co-transfected into the host cell.

Non-covalent complexes comprising a zsig51 polypeptide can be prepared by incubating a zsig51 polypeptide and a second polypeptide (e.g., a common alpha subunit) at near-physiological pH. In a typical reaction, polypeptides at a concentration of about 0.1–0.5 μg/μl are incubated at pH≈7.4 in a weak buffer (e.g., 0.01 M phosphate or acetate buffer); sodium chloride may be included at a concentration of about 0.1 M. At 37° C the reaction is essentially complete with 4–24 hours. See, for example, Weintraub et al., *Endocrinology* 101:225–235, 1997.

It is preferred to purify the polypeptides and proteins of the present invention to ≧80% purity, more preferably to ≧90% purity, even more preferably ≧95% purity, and particularly preferred is a pharmaceutically pure state, that is greater than 99.9% pure with respect to contaminating macromolecules, particularly other proteins and nucleic acids, and free of infectious and pyrogenic agents. Preferably, a purified polypeptide or protein is substantially free of other polypeptides or proteins, particularly those of animal origin.

Expressed recombinant zsig51 polypeptides (including chimeric polypeptides and polypeptide dimers) are purified by conventional protein purification methods, typically by a combination of chromatographic techniques. See, in general, *Affinity Chromatography: Principles & Methods,* Pharmacia LKB Biotechnology, Uppsala, Sweden, 1988; and Scopes, *Protein Purification: Principles and Practice,* Springer-Verlag, New York, 1994. Proteins comprising a polyhistidine affinity tag (typically about 6 histidine residues) are purified by affinity chromatography on a nickel chelate resin. See, for example, Houchuli et al., *Bio/Technol.* 6: 1321–1325, 1988. Proteins comprising a glu-glu tag can be purified by immunoaffinity chromatography essentially as disclosed by Grussenmeyer et al., ibid.

Zsig51 polypeptides or fragments thereof can also be prepared through chemical synthesis according to methods known in the art, including exclusive solid phase synthesis, partial solid phase methods, fragment condensation or classical solution synthesis. See, for example, Merrifield, *J. Am. Chem. Soc.* 85:2149, 1963; Stewart et al., *Solid Phase Peptide Synthesis* (2nd edition), Pierce Chemical Co., Rockford, Ill., 1984; Bayer and Rapp, *Chem. Pept. Prot.* 3:3, 1986; and Atherton et al., *Solid Phase Peptide Synthesis: A Practical Approach,* IRL Press, Oxford, 1989.

Using methods known in the art, zsig51 proteins can be prepared as monomers or multimers; glycosylated or non-glycosylated; pegylated or non-pegylated; and may or may not include an initial methionine amino acid residue.

Activity of zsig51 polypeptides and proteins can be measured in vitro using cultured cells or in vivo by administering molecules of the claimed invention to the appropriate animal model. For example, mitogenic activity can be measured using known assays, including $^3$H-thymidine incorporation assays (as disclosed by, e.g., Raines and Ross, *Methods Enzymol.* 109:749–773, 1985), dye incorporation assays (as disclosed by, for example, Mosman, *J. Immunol. Meth.* 65:55–63, 1983 and Raz et al., *Acta Trop.* 68:139–147, 1997) or cell counts. A preferred mitogenesis assay measures the incorporation of the dye Alamar blue (Raz et al., ibid.) into pancreatic or hypothalamic cells. See also, Gospodarowicz et al., *J. Cell. Biol.* 70:395–405, 1976; Ewton and Florini, *Endocrinol.* 106:577–583, 1980; and Gospodarowicz et al., *Proc. Natl. Acad. Sci. USA* 86:7311–7315, 1989. Differentiation can be assayed using suitable precursor cells that contain a differentiation-specific reporter element. For example, pancreatic precursor cells can be used to measure the ability of a zsig51 protein to stimulate differentiation into a specific pancreatic cell type (e.g., β-islet cells). An islet cell-specific promoter, such as an insulin gene promoter, can be linked to a reporter gene, such as a luciferase gene, whereby luciferase is expressed in the differentiated islet cells but not in the precursors. Precursor cells containing the reporter element can be obtained, for example, from mice made transgenic for the reporter element. A similar strategy can be applied to assay the effect of zsig51 protein on hypothalamic precursor cells and other cell types.

Zsig51 polypeptides and proteins can be assayed in vivo through the use of viral delivery systems. Exemplary viruses for this purpose include adenovirus, herpesvirus, vaccinia virus and adeno-associated virus (AAV). Adenovirus, a double-stranded DNA virus, is currently the best studied gene transfer vector for delivery of heterologous nucleic acid (reviewed by Becker et al., *Meth. Cell Biol.* 43:161–89, 1994; and Douglas and Curiel, *Science & Medicine* 4:44–53, 1997). The adenovirus system offers several advantages: adenovirus can (i) accommodate relatively large DNA inserts; (ii) be grown to high-titer; (iii) infect a broad range of mammalian cell types; and (iv) be used with a large number of available vectors containing different promoters. Also, because adenoviruses are stable in the bloodstream, they can be administered by intravenous injection.

By deleting portions of the adenovirus genome, larger inserts (up to 7 kb) of heterologous DNA can be accommodated. These inserts can be incorporated into the viral DNA by direct ligation or by homologous recombination with a co-transfected plasmid. In an exemplary system, the essential E1 gene is deleted from the viral vector, and the virus does not replicate unless the E1 gene is provided by the host cell (e.g., the human 293 cell line). When intravenously administered to intact animals, adenovirus primarily targets the liver. If the adenoviral delivery system has an E1 gene deletion, the virus cannot replicate in the host cells. However, the host's tissue (e.g., liver) will express and process (and, if a signal sequence is present, secrete) the heterologous protein. Secreted proteins will enter the circulation in the highly vascularized liver, and effects on the infected animal can be determined.

Mice engineered to express the zsig51 gene, referred to as "transgenic mice", and mice that exhibit a complete absence of zsig51 gene function, referred to as "knockout mice", can also be generated (Snouwaert et al., *Science* 257:1083, 1992; Lowell et al., *Nature* 366:740–742, 1993; Capecchi, *Science* 244:1288–1292, 1989; Palmiter et al. *Annu. Rev. Genet.* 20:465–499, 1986). For example, transgenic mice that over-express zsig51, either ubiquitously or under a tissue-specific or tissue-restricted promoter, can be used to determine if over-expression causes a phenotype. For example, over-expression of a wild-type zsig51 polypeptide, polypeptide fragment, or a mutant thereof may alter normal cellular processes, resulting in a phenotype that identifies a tissue in which zsig51 expression is functionally relevant and may indicate a therapeutic target for the zsig51, its agonists or antagonists. Moreover, such over-expression may result in a phenotype that shows similarity with human diseases. Similarly, knockout zsig51 mice can be used to determine where zsig51 is absolutely required in vivo. The phenotype of knockout mice may be predictive of the in vivo effects of a zsig51 antagonist such as those described herein. The murine zsig51 cDNA can be used to isolate murine genomic DNA, which is subsequently used to generate knockout mice. These mice can be employed to study the zsig51 gene and the protein encoded thereby in an in vivo system, and can be used as in vivo models for corresponding human diseases. Transgenic expression of zsig51 antisense polynucleotides or ribozymes directed against zsig51 can also be used to determine the effects of lack of zsig51 expression.

Proteins of the present invention are useful for modulating the proliferation, differentiation, or metabolism of responsive cell types, both in vitro and in vivo. Responsive cell types include both primary cells and cultured cell lines. Of particular interest in this regard are pancreatic cells, testis cells, eye cells, and pituitary cells. For example, proteins of the present invention are added to cell culture media at a concentration of about 10 pg/ml to about 100 ng/ml. Those skilled in the art will recognize that zsig51 proteins can be advantageously combined with other growth factors in culture media.

Polypeptides and proteins of the present invention can be used to identify and isolate receptors involved in growth regulation in pancreas and pituitary. For example, zsig51 proteins and polypeptides can be immobilized on a column, and membrane preparations run over the column (as generally disclosed in *Immobilized Affinity Ligand Techniques*, Hermanson et al., eds., Academic Press, San Diego, Calif., 1992, pp.195–202). Proteins and polypeptides can also be radiolabeled (*Methods Enzymol.*, vol. 182, "Guide to Protein Purification", M. Deutscher, ed., Academic Press, San Diego, 1990, 721–737) or photoaffinity labeled (Brunner et al., *Ann. Rev. Biochem.* 62:483–514, 1993 and Fedan et al., *Biochem. Pharmacol.* 33:1167–1180, 1984) and used to tag specific cell-surface proteins. In a similar manner, radiolabeled zsig51 proteins and polypeptides can be used to clone the cognate receptor in binding assays using cells transfected with an expression cDNA library.

The polypeptides, nucleic acid and/or antibodies of the present invention may be used in diagnosis or treatment of disorders associated with the pancreas or pituitary, particularly disorders characterized by cell loss or abnormal cell proliferation (including cancer). In particular, cancers of the pancreas and pituitary and diabetes may be amenable to such diagnosis, treatment or prevention.

Monomeric zsig51 polypeptides may be useful in the treatment of diseases characterized by the overexpression of a glycoprotein hormone. Zsig51 polypeptides could be used to titrate the common alpha subunit and thereby act as an antagonist of hormone activity.

If a mammal has an insufficiency of zsig51 polypeptide (due to, for example, a mutated or absent zsig51 gene), the zsig51 gene can be introduced into the cells of the mammal. In one embodiment, a gene encoding a zsig51 polypeptide is introduced in vivo in a viral vector. Such vectors include an attenuated or defective DNA virus, such as, but not limited to, herpes simplex virus (HSV), papillomavirus, Epstein Barr virus (EBV), adenovirus, adeno-associated virus (AAV), and the like. Defective viruses, which entirely or almost entirely lack viral genes, are preferred. A defective virus is not infective after introduction into a cell. Use of defective viral vectors allows for administration to cells in a specific, localized area, without concern that the vector can infect other cells. Examples of particular vectors include, but are not limited to, a defective herpes simplex virus 1 (HSV1) vector (Kaplitt et al., *Molec. Cell. Neurosci.* 2:320–30, 1991); an attenuated adenovirus vector, such as the vector described by Stratford-Perricaudet et al. (*J. Clin. Invest.* 90:626–30, 1992); and a defective adeno-associated virus vector (Samulski et al., *J. Virol.* 61:3096–101, 1987; Samulski et al., *J. Virol.* 63:3822–28, 1989).

Within another embodiment, the zsig51 gene can be introduced in a retroviral vector, e.g., as described in Anderson et al., U.S. Pat. No. 5,399,346; Mann et al., *Cell* 33:153, 1983; Temin et al., U.S. Pat. No. 4,650,764; Temin et al., U.S. Pat. No. 4,980,289; Markowitz et al., *J. Virol.* 62:1120, 1988; Temin et al., U.S. Pat. No. 5,124,263; International Patent Publication No. WO 95/07358, published Mar. 16, 1995 by Dougherty et al.; and Kuo et al., *Blood* 82:845–852, 1993. In the alternative, the vector can be introduced by lipofection in vivo using liposomes. Synthetic cationic lipids can be used to prepare liposomes for in vivo transfection of a gene encoding a marker (Felgner et al., *Proc. Natl. Acad. Sci. USA* 84:7413–17, 1987; Mackey et al., *Proc. Natl. Acad. Sci. USA* 85:8027–31, 1988). The use of lipofection to introduce exogenous genes into specific organs in vivo has certain practical advantages, including the ability to direct transfection to particular cells. Directing transfection to particular ell types is particularly advantageous in a tissue with cellular heterogeneity, such as the pancreas, liver, kidney, or brain. Lipids can be chemically coupled to other molecules for the purpose of targeting. Targeted peptides (e.g., hormones or neurotransmitters), proteins such as antibodies, or non-peptide molecules can be coupled to liposomes chemically.

Within another embodiment, target cells are removed from the body, heterologous DNA is introduced as a naked DNA plasmid, and the cells are re-implanted in the body. Naked DNA vectors for gene therapy can be introduced into the desired host cells by methods known in the art, e.g., transfection, electroporation, microinjection, transduction, cell fusion, DEAE dextran, calcium phosphate precipitation, use of a gene gun or use of a DNA vector transporter. See, e.g., Wu et al., *J. Biol. Chem.* 267:963–67, 1992; Wu et al., *J. Biol. Chem.* 263:14621–24, 1988.

The present invention further provides antisense polynucleotides that are complementary to a segment of the polynucleotides set forth in SEQ ID NO: 1. Such synthetic antisense oligonucleotides are designed to bind to mRNA encoding zsig51 polypeptides and to inhibit translation of such mRNA. Such antisense oligonucleotides are used to inhibit expression of zsig51 polypeptide-encoding genes in cell culture or in a subject. Antisense approaches may be applied in the treatment of conditions such as cancers or hyperplasias of the pancreas or pituitary, pituitary hormone hypersecretion, prolactin hypersecretion, growth hormone hypersecretion (acromegaly), and ACTH hypersecretion (Cushing's disease).

The present invention also provides reagents for use in diagnostic applications. For example, the zsig51 gene, a probe comprising zsig51 DNA or RNA, or a subsequence thereof can be used to determine if the zsig51 gene is present on chromosome 11 or if a mutation has occurred. Detectable chromosomal aberrations at the zsig51 gene locus include, but are not limited to, aneuploidy, gene copy number changes, insertions, deletions, restriction site changes and rearrangements. These aberrations can occur within the coding sequence, within introns, or within flanking sequences, including upstream promoter and regulatory regions, and may be manifested as physical alterations within a coding sequence or changes in gene expression level. Analytical probes will generally be at least 20 nucleotides in length, although somewhat shorter probes (14–17 nucleotides) can be used. PCR primers are at least 5 nucleotides in length, preferably 15 or more nt, more preferably 20–30 nt. Short polynucleotides can be used when a small region of the gene is targetted for analysis. For gross analysis of genes, a polynucleotide probe may comprise an entire exon or more. Probes will generally comprise a polynucleotide linked to a signal-generating moiety such as a radionucleotide. In general, these diagnostic methods comprise the steps of (a) obtaining a genetic sample from a patient; (b) incubating the genetic sample with a polynucleotide probe or primer as disclosed above, under conditions wherein the polynucleotide will hybridize to complementary polynucleotide sequence, to produce a first reaction product; and (c) comparing the first reaction product to a control reaction product. A difference between the first reaction product and the control reaction product is indicative of a genetic abnormality in the patient. Genetic samples for use within the present invention include genomic DNA, cDNA, and RNA. The polynucleotide probe or primer can be RNA or DNA, and will comprise a portion of SEQ ID NO:1, the complement of SEQ ID NO:1, or an RNA equivalent thereof. Suitable assay methods in this regard include molecular genetic techniques known to those in the art, such as restriction fragment length polymorphism (RFLP) analysis, short tandem repeat (STR) analysis employing PCR techniques, ligation chain reaction (Barany, *PCR Methods and Applications* 1:5–16, 1991), ribonuclease protection assays, and other genetic linkage analysis techniques known in the art (Sambrook et al., ibid.; Ausubel et. al., ibid.; A. J. Marian, *Chest* 108:255–65, 1995). Ribonuclease protection assays (see, e.g., Ausubel et al., ibid., ch. 4) comprise the hybridization of an RNA probe to a patient RNA sample, after which the reaction product (RNA-RNA hybrid) is exposed to RNase. Hybridized regions of the RNA are protected from digestion. Within PCR assays, a patient genetic sample is incubated with a pair of oligonucleotide primers, and the region between the primers is amplified and recovered. Changes in size, amount, or sequence of recovered product are indicative of mutations in the patient. Another PCR-based technique that can be employed is single strand conformational polymorphism (SSCP) analysis (Hayashi, *PCR Methods and Applications* 1:34–38, 1991).

Assays for zsig51 protein in serum may be used to detect metabolic abnormalities such as diabetes, pituitary abnormalities, and reproductive system abnormalities, the latter including infertility. Those skilled in the art will recognize that conditions related to zsig51 underexpression or overexpression may be amenable to treatment by therapeutic manipulation of zsig51 protein levels.

Receptor-binding zsig51 polypeptides can also be used within other assay systems known in the art. Such systems include Scatchard analysis for determination of binding affinity (see Scatchard, *Ann. NY Acad. Sci.* 51: 660–72, 1949) and calorimetric assays (Cunningham et al., *Science* 253:545–48, 1991; Cunningham et al., *Science* 245:821–25, 1991).

Zsig51 can also be used to identify inhibitors of its activity. Test compounds are added to the assays disclosed above to identify compounds that inhibit the activity of zsig51. In addition to those assays disclosed above, samples can be tested for inhibition of zsig51 activity within a variety of assays designed to measure receptor binding or the stimulation/inhibition of zsig51-dependent cellular responses. For example, zsig51-responsive cell lines can be transfected with a reporter gene construct that is responsive to a zsig51-stimulated cellular pathway. Reporter gene constructs of this type are known in the art, and will generally comprise a zsig51-activated serum response element (SRE) operably linked to a gene encoding an assayable protein, such as luciferase. Candidate compounds, solutions, mixtures or extracts are tested for the ability to inhibit the activity of zsig51 on the target cells as evidenced by a decrease in zsig51 stimulation of reporter gene expression. Assays of this type will detect compounds that directly block zsig51 binding to cell-surface receptors, as well as compounds that block processes in the cellular pathway subsequent to receptor-ligand binding. In the alternative, compounds or other samples can be tested for direct blocking of zsig51 binding to receptor using zsig51 tagged with a detectable label (e.g., $^{125}$I, biotin, horseradish peroxidase, FITC, and the like). Within assays of this type, the ability of a test sample to inhibit the binding of labeled zsig51 to the receptor is indicative of inhibitory activity, which can be confirmed through secondary assays. Receptors used within binding assays may be cellular receptors or isolated, immobilized receptors.

The invention further provides polypeptides that comprise an epitope-bearing portion of a protein as shown in SEQ ID NO:2, SEQ ID NO:32, or SEQ ID NO:39. An "epitope" is a region of a protein to which an antibody can bind. See, for example, Geysen et al., *Proc. Natl. Acad. Sci. USA* 81:3998–4002, 1984. Epitopes can be linear or conformational, the latter being composed of discontinuous regions of the protein that form an epitope upon folding of the protein. Linear epitopes are generally at least 6 amino acid residues in length. Relatively short synthetic peptides that mimic part of a protein sequence are routinely capable of eliciting an antiserum that reacts with the partially mimicked protein. See, Sutcliffe et al., *Science* 219:660–666, 1983. Antibodies that recognize short, linear epitopes are particularly useful in analytic and diagnostic applications that employ denatured protein, such as Western blotting (Tobin, *Proc. Natl. Acad. Sci. USA* 76:4350–4356, 1979). Antibodies to short peptides may also recognize proteins in native conformation and will thus be useful for monitoring protein expression and protein isolation, and in detecting zsig51 proteins in solution, such as by ELISA or in immunoprecipitation studies.

Antigenic, epitope-bearing polypeptides of the present invention are useful for raising antibodies, including monoclonal antibodies, that specifically bind to a zsig51 protein. Antigenic, epitope-bearing polypeptides contain a sequence of at least six, preferably at least nine, more preferably from 15 to about 30 contiguous amino acid residues of a zsig51 protein (e.g., SEQ ID NO:2). Polypeptides comprising a larger portion of a zsig51 protein, i.e. from 30 to 50 residues up to the entire sequence are included. It is preferred that the amino acid sequence of the epitope-bearing polypeptide is selected to provide substantial solubility in aqueous solvents, that is the sequence includes relatively hydrophilic residues, and hydrophobic residues are substantially avoided.

As used herein, the term "antibodies" includes polyclonal antibodies, monoclonal antibodies, antigen-binding fragments thereof such as F(ab')$_2$ and Fab fragments, single chain antibodies, and the like, including genetically engineered antibodies. Non-human antibodies can be humanized by grafting only non-human CDRs onto human framework and constant regions, or by incorporating the entire non-human variable domains (optionally "cloaking" them with a human-like surface by replacement of exposed residues, wherein the result is a "veneered" antibody). In some instances, humanized antibodies may retain non-human residues within the human variable region framework domains to enhance proper binding characteristics. Through humanizing antibodies, biological half-life may be increased, and the potential for adverse immune reactions upon administration to humans is reduced. One skilled in the art can generate humanized antibodies with specific and different constant domains (i.e., different Ig subclasses) to facilitate or inhibit various immune functions associated with particular antibody constant domains.

Alternative techniques for generating or selecting antibodies useful herein include in vitro exposure of lymphocytes to zsig51 polypeptide, and selection of antibody display libraries in phage or similar vectors (for instance, through use of immobilized or labeled zsig51 polypeptide). Human antibodies can be produced in transgenic, non-human animals that have been engineered to contain human immunoglobulin genes as disclosed in WIPO Publication WO 98/24893. It is preferred that the endogenous immunoglobulin genes in these animals be inactivated or eliminated, such as by homologous recombination.

Antibodies are defined to be specifically binding if they bind to a zsig51 polypeptide with an affinity at least 10-fold greater than the binding affinity to control (non-zsig51) polypeptide. It is preferred that the antibodies exhibit a binding affinity ($K_a$) of $10^6$ M$^{-1}$ or greater, preferably $10^7$ M$^{-1}$ or greater, more preferably $10^8$ M$^{-1}$ or greater, and most preferably $10^9$ M$^{-1}$ or greater. The affinity of a monoclonal antibody can be readily determined by one of ordinary skill in the art (see, for example, Scatchard, *Ann. NY Acad. Sci.* 51: 660–672, 1949).

Methods for preparing polyclonal and monoclonal antibodies are well known in the art (see for example, Hurrell, J. G. R., Ed., *Monoclonal Hybridoma Antibodies: Techniques and Applications*, CRC Press, Inc., Boca Raton, Fla., 1982). As would be evident to one of ordinary skill in the art, polyclonal antibodies can be generated from a variety of warm-blooded animals such as horses, cows, goats, sheep, dogs, chickens, rabbits, mice, and rats. The immunogenicity of a zsig51 polypeptide may be increased through the use of an adjuvant such as alum (aluminum hydroxide) or Freund's complete or incomplete adjuvant. Polypeptides useful for immunization also include fusion polypeptides, such as fusions of a zsig51 polypeptide or a portion thereof with an immunoglobulin polypeptide or with maltose binding protein. The polypeptide immunogen may be a full-length molecule or a portion thereof. If the polypeptide portion is "hapten-like", such portion may be advantageously joined or linked to a macromolecular carrier (such as keyhole limpet hemocyanin (KLH), bovine serum albumin (BSA) or tetanus toxoid) for immunization.

A variety of assays known to those skilled in the art can be utilized to detect antibodies that specifically bind to zsig51 polypeptides. Exemplary assays are described in detail in *Antibodies: A Laboratory Manual,* Harlow and Lane (Eds.), Cold Spring Harbor Laboratory Press, 1988. Representative examples of such assays include concurrent immunoelectrophoresis, radio-immunoassays, radio-immunoprecipitations, enzyme-linked immunosorbent assays (ELISA), dot blot assays, Western blot assays, inhibition or competition assays, and sandwich assays.

Antibodies to zsig51 can be used, for example, to isolate zsig51 polypeptides by affinity purification; for diagnostic assays for determining circulating or localized levels of zsig51 polypeptides; for screening expression libraries; for generating anti-idiotypic antibodies; and as neutralizing antibodies or as antagonists to block zsig51 activity in vitro and in vivo.

Antibodies and polypeptides disclosed herein can also be directly or indirectly conjugated to drugs, toxins, radionuclides, and the like, and these conjugates used for in vivo diagnostic or therapeutic applications. For instance, polypeptides or antibodies of the present invention may used to identify or treat tissues or organs that express a corresponding anti-complementary molecule (receptor or antigen, respectively, for instance). More specifically, zsig51 polypeptides or anti-zsig51 antibodies, or bioactive fragments or portions thereof, can be coupled to detectable or cytotoxic molecules and delivered to a mammal having cells, tissues or organs that express the anti-complementary molecule. Suitable detectable molecules may be directly or indirectly attached to the polypeptide or antibody, and include radionuclides, enzymes, substrates, cofactors, inhibitors, fluorescent markers, chemiluminescent markers, magnetic particles, and the like. Cytotoxic molecules can be directly or indirectly attached to the polypeptide or antibody, and include bacterial or plant toxins (for instance, diphtheria toxin, Pseudomonas exotoxin, ricin, saporin, abrin, and the like), as well as therapeutic radionuclides, such as iodine-131, rhenium-188 or yttrium-90 (either directly attached to the polypeptide or antibody, or indirectly attached through means of a chelating moiety, for instance). Polypeptides or antibodies can also be conjugated to cytotoxic drugs, such as adriamycin. For indirect attachment of a detectable or cytotoxic molecule, the detectable or cytotoxic molecule may be conjugated with a member of a complementary/anticomplementary pair, where the other member is bound to the polypeptide or antibody portion. For these purposes, biotin/streptavidin is an exemplary complementary/anticomplementary pair.

In another embodiment, polypeptide-toxin fusion proteins or antibody-toxin or fragment-toxin fusion proteins may be used for targeted cell or tissue inhibition or ablation (for instance, to treat cancer cells or tissues). Target cells (i.e., those displaying the zsig51 receptor) bind the zsig51-toxin conjugate, which is then internalized, killing the cell. The effects of receptor-specific cell killing (target ablation) are revealed by changes in whole animal physiology or through histological examination. Thus, ligand-dependent, receptor-directed cyotoxicity can be used to enhance understanding of the physiological significance of a protein ligand. A preferred such toxin is saporin. Mammalian cells have no receptor for saporin, which is non-toxic when it remains extracellular. Alternatively, if the polypeptide has multiple functional domains (i.e., an activation domain or a ligand binding domain, plus a targeting domain), a fusion protein including only the targeting domain may be suitable for directing a detectable molecule, a cytotoxic molecule or a complementary molecule to a cell or tissue type of interest. In instances where the domain-only fusion protein includes a complementary molecule, the anti-complementary molecule can be conjugated to a detectable or cytotoxic molecule. Such domain-complementary molecule fusion proteins thus represent a generic targeting vehicle for cell- or tissue-specific delivery of generic anti-complementary-detectable/cytotoxic molecule conjugates.

In another embodiment, polypeptide-cytokine fusion proteins or antibody-cytokine fusion proteins may be used for enhancing in vitro cytotoxicity (for instance, that mediated by monoclonal antibodies against tumor targets) and for enhancing in vivo killing of target tissues (for example, blood and bone marrow cancers). See, generally, Hornick et al., *Blood* 89:4437–447, 1997). In general, cytokines are toxic if administered systemically. The described fusion proteins enable targeting of a cytokine to a desired site of action, thereby providing an elevated local concentration of cytokine. Suitable zsig51 polypeptides or anti-zsig51 antibodies target an undesirable cell or tissue (e.g., a tumor), and the fused cytokine mediates improved target cell lysis by effector cells. Suitable cytokines for this purpose include, for example, interleukin-2 and granulocyte-macrophage colony-stimulating factor (GM-CSF).

The bioactive polypeptide and antibody conjugates described herein can be delivered intravenously, intraarterially or intraductally, or may be introduced locally at the intended site of action.

Inhibitors of zsig51 activity (zsig51 antagonists) include anti-zsig51 antibodies and soluble zsig51 receptors, as well as other peptidic and non-peptidic agents (including ribozymes). Such antagonists can be used to block the effects of zsig51 in vitro and in vivo. Of particular interest is the use of antagonists of zsig51 activity in cancer therapy. As early detection methods improve it becomes possible to intervene at earlier times in tumor development, making it feasible to use inhibitors of angiogenesis to block the angiogenic switch that precedes the progression to invasive cancer. Inhibitors of zsig51 activity can be used in combination with other cancer therapeutic agents.

Radiation hybrid mapping is a somatic cell genetic technique developed for constructing high-resolution, contiguous maps of mammalian chromosomes (Cox et al., *Science* 250:245–50, 1990). Partial or full knowledge of a gene's sequence allows one to design PCR primers suitable for use with chromosomal radiation hybrid mapping panels. Commercially available radiation hybrid mapping panels which cover the entire human genome, such as the Stanford G3 RH Panel and the GeneBridge 4 RH Panel (Research Genetics, Inc., Huntsville, Ala.), are available. These panels enable rapid, PCR-based chromosomal localizations and ordering of genes, sequence-tagged sites (STSs), and other nonpolymorphic and polymorphic markers within a region of interest, allowing the establishment of directly proportional physical distances between newly discovered genes of interest and previously mapped markers. The precise knowledge of a gene's position can be useful for a number of purposes, including: 1) determining if a sequence is part of an existing contig and obtaining additional surrounding genetic sequences in various forms, such as YACs, BACs or cDNA clones; 2) providing a possible candidate gene for an inheritable disease which shows linkage to the same chromosomal region; and 3) cross-referencing model organisms, such as mouse, which may aid in determining what function a particular gene might have. The human zsig51 gene has been localized to chromosome band 11q13. Several other genes of interest have been localized to this region of chromosome 11, including tumor suppressor gene MEN1 (multiple endocrine neoplasia type 1, an autosomal dominant familial cancer syndrome characterized by tumors in enteropancreatic endocrine tissues, anterior pituitary, and parathyroid, and by peptic ulcers), which has been positionally cloned (Chandrasekharappa et al., *Science* 276:404–407, 1997), and a second, as yet uncloned, gene also associated with MEN1-like symptoms (Chakrabarti et al., *Genes Chromosomes Cancer* 22:130–137, 1998). Zsig51 is a candidate for this as yet unidentified disease gene, as well as for IDDM4, an insulin-dependent diabetes mellitus susceptibility locus on 11q13, and for Bardet-Biedl syndrome type 1.

For pharmaceutical use, the proteins of the present invention are formulated for parenteral, particularly intravenous or subcutaneous, delivery according to conventional methods. Intravenous administration will be by bolus injection or infusion over a typical period of one to several hours. In general, pharmaceutical formulations will include a zsig51 protein in combination with a pharmaceutically acceptable vehicle, such as saline, buffered saline, 5% dextrose in water or the like. Formulations may further include one or more excipients, preservatives, solubilizers, buffering agents, albumin to prevent protein loss on vial surfaces, etc. Methods of formulation are well known in the art and are disclosed, for example, in *Remington: The Science and Practice of Pharmacy*, Gennaro, ed., Mack Publishing Co., Easton, Pa., 19th ed., 1995. Therapeutic doses will generally be in the range of 0.1 to 100 μg/kg of patient weight per day, preferably 0.5–20 μg/kg per day, with the exact dose determined by the clinician according to accepted standards, taking into account the nature and severity of the condition to be treated, patient traits, etc. Doses of zsig51 protein will generally be administered on a daily to weekly schedule, with individual doses typically within the range of 0.1–10 mg/patient. Determination of dose is within the level of ordinary skill in the art. The proteins may be administered for acute treatment, over one week or less, often over a period of one to three days or may be used in chronic treatment, over several months or years. In general, a therapeutically effective amount of zsig51 is an amount sufficient to produce a clinically significant change in the targetted condition.

The invention is further illustrated by the following non-limiting examples.

EXAMPLES

Example 1

Production a Pancreatic Islet Cell cDNA Library

RNA extracted from pancreatic islet cells was reverse transcribed in the following manner. The first strand cDNA reaction contained 10 μl of human pancreatic islet cell poly d(T)-selected poly (A)⁺ mRNA (Clontech Laboratories, Inc., Palo Alto, Calif.) at a concentration of 1.0 mg/ml, and 2 μl of 20 pmole/μl first strand primer ZC6171 (SEQ ID NO:23) containing an Xho I restriction site. The mixture was heated at 70° C. for 2.5 minutes and cooled by chilling on ice. First strand cDNA synthesis was initiated by the addition of 8 μl of first strand buffer (5× SUPERSCRIPT™ buffer; Life Technologies, Gaithersburg, Md.), 4 μl of 100 mM dithiothreitol, and 3 μl of a deoxynucleotide triphosphate (dNTP) solution containing 10 mM each of dTTP, dATP, dGTP and 5-methyl-dCTP (Pharmacia LKB Biotechnology, Piscataway, N.J.) to the RNA-primer mixture. The reaction mixture was incubated at 40° C. for 2 minutes, followed by the addition of 10 μl of 200 U/μl RNase H⁻ reverse transcriptase (SUPERSCRIPT II®; Life Technologies). The efficiency of the first strand synthesis was analyzed in a parallel reaction by the addition of 10 μCi of $^{32}$P-αdCTP to a 5 μl aliquot from one of the reaction mixtures to label the reaction for analysis. The reactions were incubated at 40° C. for 5 minutes, 45° C. for 50 minutes, then incubated at 50° C. for 10 minutes. Unincorporated $^{32}$P-αdCTP in the labeled reaction was removed by chromatography on a 400 pore size gel filtration column (Clontech Laboratories, Inc.). The unincorporated nucleotides and primers in the unlabeled first strand reactions were removed by chromatography on 400 pore size gel filtration column. The length of labeled first strand cDNA was determined by agarose gel electrophoresis.

The second strand reaction contained 102 μl of the unlabeled first strand cDNA, 30 μl of 5× polymerase I buffer (125 mM Tris-HCl, pH 7.5, 500 mM KCl, 25 mM MgCl₂, 50 mM (NH₄)₂SO₄)), 2.0 μl of 100 mM dithiothreitol, 3.0 μl of a solution containing 10 mM of each deoxynucleotide triphosphate, 7 μl of 5 mM β-NAD, 2.0 μl of 10 U/μl E. coli DNA ligase (New England Biolabs), 5 μl of 10 U/μl E. coli DNA polymerase I (New England Biolabs, Beverly, Mass.), and 1.5 μl of 2 U/μl RNase H (Life Technologies). A 10 μl aliquot from one of the second strand synthesis reactions was labeled by the addition of 10 μCi $^{32}$P-αdCTP to monitor the efficiency of second strand synthesis. The reactions were incubated at 16° C. for two hours, followed by the addition of 1 μl of a 10 mM dNTP solution and 6.0 μl T4 DNA polymerase (10 U/μl, Boehringer Mannheim, Indianapolis, Ind.) and incubated for an additional 10 minutes at 16° C. Unincorporated $^{32}$P-αdCTP in the reaction mixture was removed by chromatography through a 400 pore size gel filtration column before analysis by agarose gel electrophoresis. The reaction was terminated by the addition of 10.0 μl 0.5 M EDTA and extraction with phenol/chloroform and chloroform followed by ethanol precipitation in the presence of 3.0 M Na acetate and 2 μl of Pellet Paint carrier (Novagen, Madison, Wis.). The yield of cDNA was estimated to be approximately 2 μg from starting mRNA template of 10 μg.

Eco RI adapters were ligated onto the 5' ends of the cDNA described above to enable cloning into an expression vector. A 12.5 μl aliquot of cDNA (˜2.0 μg) and 3 μl of 69 pmole/μl of Eco RI adapter (Pharmacia LKB Biotechnology Inc., Piscataway, N.J.) were mixed with 2.5 μl 10× ligase buffer (660 mM Tris-HCl pH 7.5, 100 mM MgCl₂), 2.5 μl of 10 mM ATP, 3.5 μl 0.1 M DTT and 1 μl of 15 U/μl T4 DNA ligase (Promega Corp., Madison, Wis.). The reaction was incubated 1 hour at 5° C., 2 hours at 7.5° C., 2 hours at 10° C., 2 hours at 12.5° C. and 16 hours at 10° C. The reaction was terminated by the addition of 65 μl H₂O and 10 μl 10×H buffer (Boehringer Mannheim, Indianapolis, Ind.) and incubation at 70° C. for 20 minutes.

To facilitate the directional cloning of the cDNA into an expression vector, the cDNA was digested with Xho I, resulting in a cDNA having a 5' Eco RI cohesive end and a 3' Xho I cohesive end. The Xho I restriction site at the 3' end of the cDNA had been previously introduced. Restriction enzyme digestion was carried out in a reaction mixture by the addition of 1.0 μl of 40 U/μl Xho I (Boehringer Mannheim). Digestion was carried out at 37° C. for 45 minutes. The reaction was terminated by incubation at 70° C. for 20 minutes and chromatography through a 400 pore size gel filtration column.

The cDNA was ethanol precipitated, washed with 70% ethanol, air dried and resuspended in 10.0 μl water, 2 μl of 10× kinase buffer (660 mM Tris-HCl, pH 7.5, 100 mM MgCl₂), 0.5 μl 0.1 M DTT, 2 μl 10 mM ATP, 2 μl T4 polynucleotide kinase (10 U/μl, Life Technologies). Following incubation at 37° C. for 30 minutes, the cDNA was ethanol precipitated in the presence of 2.5 M ammonium acetate, and electrophoresed on a 0.8% low melt agarose gel. The contaminating adapters and cDNA below 0.6 kb in length were excised from the gel. The electrodes were reversed, and the cDNA was electrophoresed until concentrated near the lane origin. The area of the gel containing the concentrated cDNA was excised and placed in a microfuge tube, and the approximate volume of the gel slice was determined. An aliquot of water approximately three times the volume of the gel slice (300 μl) and 35 μl 10× β-agarose I buffer (New England Biolabs) were added to the tube, and the agarose was melted by heating to 65° C. for 15 minutes. Following equilibration of the sample to 45° C., 3 μl of 1 U/μl β-agarase I (New England Biolabs, Beverly, Mass.) was added, and the mixture was incubated for 60 minutes at 45° C. to digest the agarose. After incubation, 40 μl of 3 M Na acetate was added to the sample, and the mixture was incubated on ice for 15 minutes. The sample was centrifuged at 14,000×g for 15 minutes at room temperature to remove undigested agarose. The cDNA was ethanol precipitated, washed in 70% ethanol, air-dried and resuspended in 40 μl water.

Following recovery from low-melt agarose gel, the cDNA was cloned into the Eco RI and Xho I sites of a phagemid vector (pBluescript II SK⁺; Stratagene, La Jolla, Calif.) and electroporated into DH10B cells. Bacterial colonies containing ESTs of known genes were identified and eliminated from sequence analysis by reiterative cycles of probe hybridization to hi-density colony filter arrays (Genome Systems, St. Louis, Mich.). cDNAs of known genes were pooled in groups of 50–100 inserts and were labeled with $^{32}$P-αdCTP using a MEGAPRIME labeling kit (Amersham, Arlington Heights, Ill.). Colonies which did not hybridize to the probe mixture were selected for sequencing. Sequencing was done using automated equipment. The resulting data were analyzed, resulting in the identification of a novel EST designated SISF1000391. The sequence of this EST is shown in SEQ ID NO:24. The plasmid containing this insert was designated pSLSIG51-1. The insert was sequenced and found to comprise the sequence shown in SEQ ID NO:1.

Subsequent to the cloning of pSLSIG51-1, a zsig51 clone was identified in a pituitary cDNA library.

Example 2

Tissue Distribution of Zsig51

Blots of human RNA (Human Multiple Tissue Northern Blots I, II, and III; and Human RNA Master Blot; Clontech Laboratories, Inc., Palo Alto, Calif.) were probed to determine the tissue distribution of zsig51. A cDNA probe was generated using 20 pmoles each of oligonucleotide primers ZC16,013 (SEQ ID NO:25) and ZC16,014 (SEQ ID NO:26) and 5 μl of a pancreas cDNA library (prepared from pancreas RNA using a commercially available kit (Marathon™ cDNA Amplification Kit from Clontech Laboratories, Inc.) and diluted 1:100). The probe was generated by PCR, incubating the reaction mixture at 94° C. for 1 minute followed by 30 cycles of 94° C., 20 seconds; 64° C., 30 seconds; 72° C., 30 seconds; then a final extension for 7 minutes at 72° C. Reaction products were electrophoresed on a 1.25% Tris-borate/EDTA gel, and the 180 bp product was excised from the gel. DNA was extracted from the gel slab using a commercially available kit (QIAquick™ Gel Extraction Kit; Qiagen, Inc., Santa Clarita, Calif.). This PCR product was sequenced and found to be a portion of the zsig51 sequence. 98.7 ng of the extracted fragment was labeled with $^{32}$P (Multiprime™ DNA Labeling System; Amersham Corporation, Arlington Heights, Ill.). Unincorporated radioactivity was removed by column chromatography using a commercially available push column (NucTrap® column; Stratagene Cloning Systems, La Jolla, Calif.; see U.S. Pat. No. 5,336,412). The blots were prehybridized for 3 hours at 65° C. in a hybridization solution (ExpressHyb™ Hybridization Solution; Clontech Laboratories, Inc.) containing 1 mg of boiled salmon sperm DNA. $10.2 \times 10^6$ cpm of probe and 1 mg of salmon sperm DNA were boiled for 5 minutes, iced, mixed with 10 ml of ExpressHyb™ solution, and added to the blots. The blots were incubated in the solution overnight at 65° C. Initial washes were done for 40 minutes in 2×SSC, 0.1% SDS at room temperature, followed by a 40-minute wash at 50° C. in 0.1×SSC, 0.1% SDS with one change of wash solution. The washed blots were exposed to film at −80° C. overnight, then washed again with 0.1×SSC, 0.1% SDS at 65° C. for 40 minutes to remove background and exposed overnight at −80° C. High expression was seen in pancreas, with lower expression in pituitary gland. The transcript size was approximately 1 kb.

Additional Northern blotting experiments were carried out essentially as disclosed above using a longer human zsig51 probe. Similar expression in pancreas and pituitary was seen, and a low-abundance transcript of approximately 4 kb was seen in human testis.

Example 3

Chromosomal Mapping

Human zsig51 was mapped to chromosome 11 using the commercially available GeneBridge 4 Radiation Hybrid Panel (Research Genetics, Inc., Huntsville, Ala.). The GeneBridge 4 Radiation Hybrid Panel contains PCRable DNAs from each of 93 radiation hybrid clones, plus two control DNAs (the HFL donor and the A23 recipient). A publicly available WWW server (http://www-genome.wi.mit.edu/cgi-bin/contig/rhmapper.pl) allows mapping relative to the Whitehead Institute/MIT Center for Genome Research's radiation hybrid map of the human genome (the "WICGR" radiation hybrid map), which was constructed with the GeneBridge 4 Radiation Hybrid Panel.

For mapping zsig51, 20-μl reaction mixtures were set up in a PCRable 96-well microtiter plate (Stratagene, La Jolla, Calif.) and used in a thermal cycler (RoboCycler® Gradient 96; Stratagene). Each of the 95 PCR reaction mixtures contained 2 μl buffer (10× KlenTaq PCR reaction buffer; Clontech Laboratories, Inc., Palo Alto, Calif.), 1.6 μl dNTPs mix (2.5 mM each, Perkin-Elmer, Foster City, Calif.), 1 μl sense primer ZC16,761 (SEQ ID NO:27), 1 μl antisense primer ZC16,760 (SEQ ID NO:28), 2 μl of a density increasing agent and tracking dye (RediLoad, Research Genetics, Inc., Huntsville, Ala.), 0.4 μl of a commercially available DNA polymerase/antibody mix (50× Advantage™ KlenTaq Polymerase Mix; Clontech Laboratories, Inc.), 25 ng of DNA from an individual hybrid clone or control and ddH2O to a total volume of 20 μl. The mixtures were overlaid with an equal amount of mineral oil and sealed. The PCR cycler conditions were as follows: an initial 5-minute denaturation at 95° C.; 35 cycles of a 1-minute denaturation at 95° C., 1 minute annealing at 66° C., and 1.5 minute extension at 72° C.; followed by a final extension for 7 minutes at 72° C. The reaction products were separated by electrophoresis on a 2% agarose gel (Life Technologies, Gaithersburg, Md.).

The results showed that zsig51 maps 6.40 cR_3000 from the framework marker WI-1409 on the chromosome 11 WICGR radiation hybrid map. Proximal and distal framework markers were WI-1409 and D11S913, respectively. The use of surrounding markers positions zsig51 in the 11q13.1 region on the integrated LDB chromosome 11 map (The Genetic Location Database, University of Southhampton, www server: http://cedar.genetics.soton.ac.uk/public_html/).

Example 4

Mouse Zsig51

A mouse zsig51 DNA sequence was identified in a database of expressed sequence tags (Marra et al., The WashU-HHMI Mouse EST Project, 1996). A clone corresponding to the EST was obtained as an *E. coli* transformant. The transformant was streaked on an LB plate containing 175 μg/ml ampicillin and 25 μg/ml methicillin and incubated overnight at 37° C. The cDNA insert was sequenced and found to contain an open reading frame encoding 128 amino acids, including a putative 20 amino acid secretory peptide. The DNA and amino acid sequences are shown in SEQ ID NO:31 and NO:32, respectively.

Example 5

Chromosomal Mapping of Mouse Zsig51 Gene

The zsig51 gene was mapped in mouse using the commercially available mouse T31 whole genome radiation hybrid (WGRH) panel (Research Genetics, Inc., Huntsville, Ala.) and Map Manager QT linkage analysis program. The T31 WGRH panel contains PCRable DNAs from each of 100 radiation hybrid clones, plus two control DNAs (the 129aa donor and the A23 recipient). For mapping, 20-μl reactions were run essentially as disclosed in Example 3 using sense primer ZC18,588 (SEQ ID NO:40), 5' CCG TTT CTC CCG CTA CTA 3', and antisense primer ZC18,589 (SEQ ID NO:41), 5' GGG CCA ACC TCA TCT TCA 3'. The PCR cycler conditions were as follows: an initial 5-minute denaturation at 94° C.; 35 cycles of 1 minute denaturation at 94° C., 1 minute annealing at 66° C., and 90 seconds extension at 72° C.; followed by a final extension of 7 minutes at 72° C. The reaction products were separated by electrophoresis on a 2% agarose gel (Life Technologies, Gaithersburg, Md.).

At P=0.0001, mouse zsig51 linked to the marker D19Mit68 with a LOD score of 8.2. D19Mit68 has been mapped at 6.0 cM on mouse chromosome 19. This is a known region of synteny or linkage conservation with the region of human chromosome 11 where the human form of zsig51 has been mapped.

Example 6

Rat Zsig51 cDNA

RNA extracted from rat pancreatic islet cells was reverse transcribed. The first strand cDNA reaction contained 16 µl of rat pancreatic islet cell poly d(T)-selected poly (A)+ mRNA at a concentration of 0.4 µg/ml, and 2 µl of 20 pmole/µl first strand primer (ZC6172; SEQ ID NO:33) containing an Xho I restriction site. The mixture was heated at 70° C. for 3 minutes and cooled by chilling on ice. First strand cDNA synthesis was initiated by the addition of 8 µl of first strand buffer (5× SUPERSCRIPT™ buffer; Life Technologies, Gaithersburg, Md.), 4 µl of 100 mM dithiothreitol, and 2 µl of a deoxynucleotide triphosphate (dNTP) solution containing 10 mM each of dTTP, dATP, dGTP and 5-methyl-dCTP (Pharmacia LKB Biotechnology, Piscataway, N.J.) to the RNA-primer mixture. The reaction mixture was incubated at 45° C. for 2 minutes, followed by the addition of 10 µl of 200 U/µl RNase H⁻ reverse transcriptase (SUPERSCRIPT II®; Life Technologies). The efficiency of the first strand synthesis was analyzed in a parallel reaction by the addition of 10 µCi of $^{32}$P-αdCTP to a 5 µl aliquot from one of the reaction mixtures to label the reaction for analysis. The reaction mixtures were incubated at 45° C. for 50 minutes, then at 50° C. for 10 minutes. Unincorporated $^{32}$P-αdCTP in the labeled reaction was removed by chromatography on a 400 pore size gel filtration column (Clontech Laboratories, Inc.). The unincorporated nucleotides and primers in the unlabeled first strand reactions were removed by chromatography on a 400 pore size gel filtration column. The length of labeled first strand cDNA was determined by agarose gel electrophoresis.

The second strand reaction contained 100 µl of the unlabeled first strand cDNA, 30 µl of 5× polymerase I buffer (125 mM Tris-HCl, pH 7.5, 500 mM KCl, 25 mM MgCl₂, 50 mM (NH₄)₂SO₄)), 2.0 µl of 100 mM dithiothreitol, 3.0 µl of a solution containing 10 mM of each deoxynucleotide triphosphate, 7 µl of 5 mM β-NAD, 2.0 µl of 10 U/µl E. coli DNA ligase (New England Biolabs), 6 µl of 10 U/µl E. coli DNA polymerase I (New England Biolabs, Beverly, Mass.), and 1.5 µl of 2 U/µl RNase H (Life Technologies). A 10-µl aliquot from one of the second strand synthesis reactions was labeled by the addition of 10 µCi $^{32}$P-αdCTP to monitor the efficiency of second strand synthesis. The reactions were incubated at 16° C. for two hours, followed by the addition of 1 µl of a 10 mM dNTP solution and 6.0 µl T4 DNA polymerase (10 U/µl, Boehringer Mannheim, Indianapolis, Ind.) and incubated for an additional 10 minutes at 16° C. Unincorporated $^{32}$P-αdCTP in the reaction mixture was removed by chromatography through a 400 pore size gel filtration column before analysis by agarose gel electrophoresis. The reaction was terminated by the addition of 5 µl 0.5 M EDTA and extraction with phenol/chloroform and chloroform followed by ethanol precipitation in the presence of 3.0 M Na acetate and 2 µl of a dye-labeled carrier (Pellet Paint™ Co-Precipitant; Novagen, Madison, Wis.). The yield of cDNA was estimated to be approximately 2 µg from starting mRNA template of 10 µg.

Eco RI adapters were ligated onto the 5' ends of the cDNA described above to enable cloning into an expression vector. A 10 µl aliquot of cDNA (~1.0 µg) and 4 µl of 69 pmole/µl of Eco RI adapter (Pharmacia LKB Biotechnology Inc., Piscataway, N.J.) were mixed with 2.5 µl 10× ligase buffer (660 mM Tris-HCl pH 7.5, 100 mM MgCl₂), 2.5 µl of 10 mM ATP, 3.5 µl 0.1 M DTT and 1 µl of 15 U/µl T4 DNA ligase (Promega Corp., Madison, Wis.). The reaction was incubated 1 hour at 5° C., 2 hours at 7.5° C., 2 hours at 10° C., 2 hours at 12.5° C. and 16 hours at 10° C. The reaction was terminated by the addition of 65 µl H₂O and 10 µl 10×H buffer (Boehringer Mannheim, Indianapolis, Ind.) and incubation at 70° C. for 20 minutes.

To facilitate the directional cloning of the cDNA into an expression vector, the cDNA was digested with Xho I, resulting in a cDNA having a 5' Eco RI cohesive end and a 3' Xho I cohesive end. The Xho I restriction site at the 3' end of the cDNA had been previously introduced. Restriction enzyme digestion was carried out in a reaction mixture by the addition of 1.0 µl of 40 U/µl Xho I (Boehringer Mannheim). Digestion was carried out at 37° C. for 45 minutes. The reaction was terminated by incubation at 70° C. for 20 minutes and chromatography through a 400 pore size gel filtration column.

The cDNA was ethanol precipitated, washed with 70% ethanol, air dried and resuspended in 13 µl water, 2 µl of 10× kinase buffer (660 mM Tris-HCl, pH 7.5, 100 mM MgCl₂), 0.5 µl 0.1 M DTT, 2.5 µl 10 mM ATP, 2 µl T4 polynucleotide kinase (10 U/µl, Life Technologies). Following incubation at 37° C. for 30 minutes, the cDNA was ethanol precipitated in the presence of 2.5 M ammonium acetate, and electrophoresed on a 0.8% low melt agarose gel. The contaminating adapters and cDNA below 0.6 kb in length were excised from the gel. The electrodes were reversed, and the cDNA was electrophoresed until concentrated near the lane origin. The area of the gel containing the concentrated cDNA was excised and placed in a microfuge tube, and the approximate volume of the gel slice was determined. An aliquot of water approximately three times the volume of the gel slice (300 µl) and 35 µl 10× β-agarase I buffer (New England Biolabs) were added to the tube, and the agarose was melted by heating to 65° C. for 15 minutes. Following equilibration of the sample to 45° C., 3 µl of 1 U/µl β-agarase I (New England Biolabs, Beverly, Mass.) was added, and the mixture was incubated for 60 minutes at 45° C. to digest the agarose. After incubation, 40 µl of 3 M Na acetate was added to the sample, and the mixture was incubated on ice for 15 minutes. The sample was centrifuged at 14,000×g for 15 minutes at room temperature to remove undigested agarose. The cDNA was ethanol precipitated, washed in 70% ethanol, air-dried and resuspended in 40 µl water.

Following recovery from the low-melt agarose gel, the cDNA was cloned into the Eco RI and Xho I sites of a phagemid vector (pBluescript® II SK(+); Stratagene, La Jolla, Calif.) and electroporated into DH10B cells.

1.5 million pfu from the rat pancreas cDNA library were plated onto 150 mm NZY plates at a density of 40,000 pfu/plate on electroporation-competent E. coli cells (XL1-Blue MRF' strain; Stratagene). Following incubation at 37° C. overnight, filter lifts were made using nylon membranes (Hybond-N™; Amersham Corporation, Arlington Heights, Ill.), according to the procedures provided by the manufacturer. The filters were processed by denaturation in a solution containing 1.5 M NaCl and 0.5 M NaOH for 7 minutes at room temperature. The filters were neutralized in 0.5 M Tris:HCl, pH 7.2 for 7 minutes. Phage DNA was fixed onto the filters with 1,200 µjoules of UV energy in a UV cross-linker (Stratagene). The filters were then washed with 0.25×SSC at 70° C. to remove excess cellular debris.

A probe was generated by PCR using oligonucleotide primers ZC16763 (SEQ ID NO:34) and ZC16753 (SEQ ID NO:35) and plasmid pSLSIG51-1 as a template. One µl of a 1:100 dilution of the plasmid prep used to sequence pSLSIG51-1 was combined with 1 µl of 20 pmole/µl ZC16763, 1 µl of 20 pmole/µl ZC16753, and 45 µl of a mixture of Taq DNA polymerase, salts, magnesium, and deoxynucleotide triphosphates (PCR Supermix; Life Technologies, Gaithersburg, Md.). The amplification was carried out at 94° C. for 30 seconds followed by 35 cycles of 20 seconds at 94° C., 20 seconds at 55° C., and 1 minute at 68° C.; followed by a final incubation at 68° C. for 5 minutes. The probe was purified by gel electrophoresis.

The filters were pre-washed six times for 30 minutes in hot 0.25×SSC, 0.25% SDS, prehybridized overnight at 60° C. in the same solution containing a 1/200 dilution of denatured herring sperm DNA, then hybridized to the probe over the weekend at 60° C. in hybridization solution (containing, per liter: 250 ml 20×SSC (0.45μfiltered), 50 ml 100× Denhardt's (5 Prime-3 Prime, Boulder, Colo.), 2 ml 0.5 M EDTA, 20 ml 10% SDS (Research Genetics, Huntsville, Ala.), and water (Baxter, McGaw Park, Ill.) containing 20 μl/ml sheared DNA (Research Genetics) denatured at 98° C. for 10 minute and ~7.5 μl probe denatured at 98° C. for 4 minutes. Positives were re-plated, and filters were prepared. These secondary filters were prewashed 5 times for 30 minutes with hot 0.25×SSC, 0.25% SDS, and prehybridized overnight at 60° C. in 0.25×SSC, 0.25% SDS containing a 1/50 dilution of denatured herring sperm DNA. Filters were then hybridized with the probe in hybridization solution containing 20 μl/ml denatured, sheared DNA (as above) and about 6 μl/ml denatured probe overnight at 60° C. Positives from the secondary screening were plated, and tertiary filters were prepared. The tertiary filters were probed with the same probe used for the secondary filters using 4.4 μl/ml denatured probe+20 μl/ml denatured, sheared DNA. Most of the tertiary filters showed dark spots on the film. Eight plugs were excised from the tertiary plates. For each of the eight plug samples, 150 μl electroporation-competent $E.\ coli$ cells (XL1-Blue MRF' strain; Stratagene, La Jolla, Calif.) were infected with 75 μl phage plus 1 μl interference-resistant helper phage (ExAssist™; Stratagene). The cells were incubated at 37° C. for 15 minutes, then 3 ml LB was added, followed by an additional 3 hour incubation with shaking. A 1-ml aliquot was taken and heated to 70° C. for 15 minutes, then centrifuged for 15 minutes at 4000 rpm. The supernatant was transferred to a new tube and stored overnight at 4° C. The next day, $E.\ coli$ cells (XLOLR strain; Stratagene, La Jolla, Calif.) were grown to an O.D. of 1.0, then 200 μl XLOLR cells and 15 μl phage serum were combined and incubated for 15 minutes at 37° C. 300 μl LB was added, and the mixture was incubated for 45 minutes at 37° C. Dilutions (1:10, 1:100, and 1:1000) of each sample were made with LB. 50 μl of each dilution was plated.

Cultures were prepared from seven of the plugs, and the insert sizes were determined by PCR using the phage as templates and 1 μl each of primers ZC5995 (SEQ ID NO:36) and ZC5996 (SEQ ID NO:37). PCR Supermix (Life Technologies, Inc., Gaithersburg, Md.) (45 μl/reaction) was used. The reaction was run in a thermal cycler (Progene Techne) at 94° C., 1 minute; 30 cycles of 95° C., 20 seconds; 64° C., 20 seconds; 68° C., 3 minutes; followed by an incubation at 68° C., 10 minutes and a 10° C. soak.

Four of the samples had inserts that appeared to be about 1300 bp. One clone was sequenced and found to be the rat ortholog of human zsig51. The sequence is shown in SEQ ID NO:38 and NO:39.

Example 7

Zsig51 Adenovirus Vector Construction

The protein coding regions of human and mouse zsig51 were amplified by PCR using primers that added FseI and AscI restriction sties at the 5' and 3' termini, respectively. PCR primers ZC17438 (SEQ ID NO:42) and ZC17439 (SEQ ID NO:43) were used with template plasmid containing the full-length human zsig51 cDNA. PCR primers ZC17950 (SEQ ID NO:44) and ZC17951 (SEQ ID NO:45) were used with template plasmid containing the full-length mouse zsig51 cDNA in a PCR reaction as follows: 95° C. for 5 minutes; 15 cycles at 95° C. for 1 min., 58° C. for 1 min., and 72° C. for 1.5 min.; 72° C. for 7 min.; followed by a 4° C. soak. The PCR reaction products were loaded onto a 1.2% (low melt) agarose (SeaPlaque GTG; FMC, Rockland, Me.) gel in TAE buffer. The zsig51 PCR products were excised from the gel and purified using a spin column containing a silica gel membrane (QIAquick™ Gel Extraction Kit; Qiagen, Inc., Valencia, Calif.). The PCR products were then digested with FseI and AscI, phenol/chloroform extracted, EtOH precipitated, and rehydrated in 20μl TE (Tris/EDTA pH 8). The 390 bp (human) and 387 bp (mouse) zsig51 fragments were then ligated into the FseI-AscI sites of the vector pMT12-8 (Example 10, below) and transformed into DH10B competent cells by electroporation. Clones containing zsig51 inserts were identified by plasmid DNA miniprep followed by digestion with FseI and AscI. A positive clone was sequenced to insure that there were no deletions or other anomalies in the construct. DNA was prepared using a commercially available kit (obtained from Qiagen, Inc.)

The zsig51 cDNA was released from the pTG12-8 vector using FseI and AscI enzymes. The cDNA was isolated on a 1% low melt agarose gel and excised from the gel, and the gel slice was melted at 70° C., extracted twice with an equal volume of Tris-buffered phenol, and EtOH precipitated. The DNA was resuspended in 10μl $H_2O$. The cDNA was ligated into pACCMV shuttle vector (Microbix Biosystems, Inc. Ontario, Canada) in which the polylinker had been modified to include FseI and AscI sites and transformed into $E.\ coli$ host cells (Electromax DH10B™ cells; obtained from Life Technologies, Inc., Gaithersburg, Md.) by electroporation. Clones containing zsig51 inserts were identified by plasmid DNA miniprep followed by digestion with FseI and AscI. A large-scale preparation of DNA was made for transfection.

The zsig51-containing shuttle vectors were co-transfected with E1-deleted, adenovirus vector pJM17 (Microbix Biosystems, Inc.) into 293A cells (Quantum Biotechnologies, Inc. Montreal, QC. Canada) that express the adenovirus E1 gene. The DNA was diluted up to a total volume of 50 μl with sterile HBS (150 mM NaCl, 20 mM HEPES). In a separate tube, 20 μl DOTAP (Boehringer Mannheim, 1 mg/ml) was diluted to a total volume of 100 μl with HBS. The DNA was added to the DOTAP, mixed gently by pipeting up and down, and left at room temperature for 15 minutes. The media was removed from the 293A cells and washed with 5 ml serum-free MEMalpha containing 1 mM sodium pyruvate, 0.1 mM MEM non-essential amino acids and 25 mM HEPES buffer (all from Life Technologies, Inc.). 5 ml of serum-free MEM was added to the 293A cells and held at 37° C. The DNA/lipid mixture was added drop-wise to the T25 flask of 293A cells, mixed gently, and incubated at 37° C. for 4 hours. After 4 hours the media containing the DNA/lipid mixture was aspirated off and replaced with 5 ml complete MEM containing 5% fetal bovine serum. Virus propagation is conditional and is achieved only by growing the E1-deleted virus in a cell line expressing the E1 gene.

Cells were maintained for 2–4 weeks until the recombination event occurred. (Recombinant virus is generated by homologous recombination of overlapping fragments of the viral genome in the pJM17 vector and the shuttle vector.) At that time, the host 293 cells were lysed by the virus, forming plaques of dead cells. Within 3–5 days the entire monolayer was completely lysed. The medium containing the viral lysate was collected and any remaining intact cells were lysed by repeated freeze/thaw cycles and the cell debris pelleted by centrifugation.

The viral lysate was then plaque-purified according to the method of Becker et al., *Meth. Cell Biol.* 43:161–189, 1994. Briefly, serial dilutions were prepared in DMEM containing 10% fetal bovine serum and 100 U/ml penicillin/streptomycin, plated on to monolayers of 293 cells, and incubated at 37° C. for one hour. A melted 1.3% agarose/water solution was mixed with 2× DMEM (containing 4% FBS, 200 U/ml penicillin/streptomycin, 0.5 μg/ml fungizone and 30 mg/ml phenol red), and 6 ml of the mixture was added to the virus-infected 293 cells followed by incubation at 37° C. until plaques formed, 7–10 days. Single plaques were isolated, and the presence of the zsig51 insert was verified by PCR. The primers were ZC12700 (SEQ ID NO:48) and ZC12742 (SEQ ID NO:49). Amplification was carried out over 30 cycles of 94° C., 0.5 minute, 55° C., 0.5 minute, and 72° C., 0.5 minute; followed by a 10-minute extension at 72° C. One plaque each for human and mouse zsig51 that had the expected size PCR product was used to do a primary amplification.

Ten 10-cm plates of nearly confluent (80–90%) 293A cells were set up 20 hours previously. Roughly 5% of the virus lysate from a plaque was added to each 10-cm plate and monitored for 48 to 72 hours looking for CPE (Cytopathic Effect) under the white light microscope. When all of the 293A cells showed CPE, this 1° stock lysate was collected and 3 freeze/thaw cycles performed.

For secondary (2°) amplification of zsig51 rAdV, 20 15-cm tissue culture dishes of 293A cells were prepared so that the cells were 80–90% confluent. All but 20 ml of 5% MEM media was removed, and each dish was inoculated with 300–500 ml of the 1° amplified rAdv lysate. After 48 hours the 293A cells were lysed from virus production, and the lysate was collected into 250-ml polypropylene centrifuge bottles.

To purify the recombinant virus, NP-40 detergent was added to a final concentration of 0.5% to the bottles of crude lysate to lyse all cells. Bottles were placed on a rotating platform for 10 min. agitating as fast as possible without the bottles falling over. The debris was pelleted by centrifugation at 20,000×G for 15 minutes. The supernatant was transferred to 250-ml polycarbonate centrifuge bottles, and 0.5 volumes of 20% PEG8000/2.5M NaCl solution was added. The bottles were shaken overnight on ice. The bottles were centrifuged at 20,000×G for 15 minutes, and supernatant was discarded into a bleach solution. Using a sterile cell scraper, the precipitate from 2 bottles was resuspended in 2.5 ml PBS. The resulting virus solution was placed in 2-ml microcentrifuge tubes and centrifuged at 14,000×G for 10 minutes to remove any additional cell debris. The supernatant from the 2-ml microcentrifuge tubes was transferred into a 15-ml polypropylene snapcap tube and adjusted to a density of 1.34 g/ml with cesium chloride (CsCl). The volume of the virus solution was estimated, and 0.55 g/ml of CsCl was added. The CsCl was dissolved, and 1 ml of this solution weighed 1.34 g. The solution was transferred to polycarbonate thick-walled centrifuge tubes 3.2 ml (Beckman) and spun at (348,000×G) for 3–4 hours at 25° C. The virus formed a white band. Using wide-bore pipette tips, the virus band was collected.

The virus from the gradient had a large amount of CsCl which was removed before it could be used on cells.

Pharmacia PD-10 columns prepacked with Sephadex G-25M (Pharmacia) were used to desalt the virus preparation. The column was equilibrated with 20 ml of PBS. The virus was loaded and allowed to run into the column. 5 ml of PBS was added to the column, and fractions of 8–10 drops were collected. The optical densities of 1:50 dilutions of each fraction were determined at 260 nm on a spectrophotometer. A clear absorbance peak was present between fractions 7–12. These fractions were pooled, and the optical density (OD) of a 1:50 dilution was determined. OD was converted to virus concentration using the formula (OD at 260 nm) (50) ($1.1 \times 10^{12}$)=virions/ml. The human zsig51 rAdV concentration was $6.1 \times 10^{12}$ virions/ml. The mouse zsig51 virus concentration was $9.2 \times 10^{12}$.

To store the virus, glycerol was added to the purified virus to a final concentration of 15%, mixed gently but effectively, and stored in aliquots at −80° C.

A protocol developed by Quantum Biotechnologies, Inc. (Montreal, Canada) was followed to measure recombinant virus infectivity. Briefly, two 96-well tissue culture plates were seeded with $1 \times 10^4$ 293A cells per well in MEM containing 2% fetal bovine serum for each recombinant virus to be assayed. After 24 hours, 10-fold dilutions of each virus from $1 \times 10^{-2}$ to $1 \times 10^{-14}$ were made in MEM containing 2% fetal bovine serum. 100 μl of each dilution was placed in each of 20 wells. After 5 days at 37° C., wells were read either positive or negative for CPE, and a value for "Plaque Forming Units/ml" (PFU) ws calculated.

$TCID_{50}$ formulation used was as per Quantum Biotechnologies, Inc., above. The titer (T) was determined from a plate where virus used was diluted from $10^{-2}$ to $10^{-14}$, and read 5 days after the infection. At each dilution a ratio (R) of positive wells for CPE per the total number of wells was determined.

Example 8

Adenovirus Administration of Zsig51 to Normal Mice

Human and mouse zsig51s were administered to mice using adenovirus vectors, prepared as disclosed above, containing the coding region of the human gene (zsig51h; SEQ ID NO:1) or its mouse orthologue (zsig51m; SEQ ID NO:31).

The adenovirus vectors were injected intravenously into C57Bl/6 mice according to the experimental design shown in Table 5. Blood was drawn and analyzed on day 12 and then again on day 21 of each experiment. All mice received bromodeoxyuridine (BrdU) in their drinking water three days before sacrifice. Animals were sacrificed on day 21. Parameters measured included weight change, complete blood counts, serum chemistries, histology, organ weights, and cell proliferation measured by BrdU incorporation.

TABLE 5

| Group 1 | zsig51 rAdV |
| | $1 \times 10^{11}$ particles/dose |
| | 10 females, 10 males |
| Group 2 | null AdV control virus |
| | $1 \times 10^{11}$ particles/dose |
| | 10 females, 10 males |
| Group 3 | no treatment |
| | 5 females, 5 males |

Female glucose levels were higher in zsig51h experimental groups than in null virus control groups. Both male and female glucose levels were lower in zsig51m experimental groups than in null virus control groups. This lowered glucose was seen in zsig51m mice both in a fasting state and in a well-fed state.

The liver weights of both males and females in zsig51m experimental groups were higher than in null virus control groups.

Example 9

In Situ Hybridization

Fresh tissue was fixed in 4% paraformaldehyde at 4° C. overnight. Tissue was embedded in paraffin using a standard protocol with the exception that Histoclear (National Diagnostics, Atlanta, Ga.) was substituted for xylene. 5–10 micron sections were mounted onto slides (Superfrost™ Plus; VWR Scientific, West Chester, Pa.), and the slides were baked at 37° C. for 4 hours, then stored at 4° C. Alternatively, fixed and sectioned tissues were obtained from commercial sources. The slides were de-waxed in Histoclear and rehydrated through an ethanol series. They were then air-dried and stored at −20° C.

For in situ hybridization, slides were allowed to come to room temperature, washed 3 times for 5 minutes each in phosphate-buffered saline containing 0.1% polyoxyethylenesorbitan monolaurate (Tween 20) (PBT), then incubated at 37° C. in PBT with proteinase K at a concentration of 2–100 μg/ml. Slides were rinsed twice for 5 minutes in PBT, fixed again in 4% paraformaldehyde for 20 minutes at room temperature, and rinsed twice for 5 minutes in PBT. Sections were acetylated by dipping the slides into a mixture of 197 ml deionized water, 2.6 ml triethanolamine, and 350 μl hydrochloric acid. 500 μl of acetic anhydride was added drop by drop while stirring, and the incubation of the slides was continued in this mixture at room temperature for 10 minutes. Slides were rinsed twice for 5 minutes in PBT, then dehydrated through a methanol series and air-dried.

The sections were hybridized with an in vitro-transcribed digoxigenin-labeled RNA antisense zsig51 probe representing the complete protein coding region of the gene. Human tissues were probed with an antisense to the human gene (SEQ ID NO:2 human coding region only) and mouse tissues were probed with an antisense to the mouse orthologue (SEQ ID NO:32 mouse coding region only). The probes were used at a concentration of 200 ng to 1 μg/ml in 50% formamide, 10% dextran sulphate, 5×SSC, 5× Denhardt's solution, 250 μg/ml yeast tRNA, 500 μg/ml salmon sperm DNA, and 50 μg/ml heparin. Hybridization was done overnight at 60–72° C. The slides were washed, using solutions preheated at 60–72° C., in 50% formamide, 2×SSC, once for 15 minutes; then in a fresh wash for 30 minutes; and finally in 25% formamide, 1×SSC, 0.5×PBS for 30 minutes. Slides were then rinsed twice in PBT at room temperature for 5 minutes.

The sections were blocked in 5% nonfat dried milk, 4×SSC, and 0.1% Tween 20 (blocking solution) with 5% normal rabbit or goat serum added for 1 hour at room temperature. Slides were then rinsed in PBT at room temperature three times for 5 minutes. Sheep anti-digoxigenin antibody (Boehringer Mannheim, Indianapolis, Ind.) was diluted 1:1000 in blocking solution, added to slides, and incubated for 30 minutes at room temperature. Slides were washed four times for 15 minutes each in blocking solution. Biotinylated rabbit-anti-sheep antibody (Vector Laboratories, Burlingame, Calif.) was diluted 1:200 in blocking solution with 7.5% normal mouse serum added, and allowed to incubate at room temperature at least 30 minutes before being added to slides and incubated for an additional 30 minutes at room temperature. Slides were then washed two times for 5 minutes each in blocking solution. Avidin and biotinylated peroxidase (Vectastain® ABC-AP Kit; Vector Laboratories) were prepared according to the manufacturer's instructions before being added to slides, which were then incubated for 30 minutes at room temperature. Slides were washed two times for 5 minutes each in blocking solution, and then equilibrated in 0.1 M Tris pH 9.5, 0.1 M sodium chloride, 50 mM magnesium chloride (AP buffer). Slides were developed in AP buffer with 4.5 μl/ml 4-nitro blue tetrazolium chloride and 3.5 μl/ml 5-bromo-4-chloro-3-indolyl-phosphate until staining was apparent through a light microscope.

In the alternative, in situ hybridization was carried out essentially as above, but using a biotin-labeled antisense RNA probe and a commercially available detection kit (Renaissance® TSA™ Indirect Signal Amplification System; NEN Life Science Products, Boston, Mass.) following the manufacturer's instructions.

In human testis tissue, strong positive staining. was seen in immature sperm precursors. The testis samples were from a 46-year-old male who died of intercranial bleeding, and a 58-year-old male with chronic obstructive pulmonary disease who died of acute respiratory failure.

In testis tissue from mouse, strong positive staining was seen in spermatogonia.

Example 10

Generation of Zsig51 Transgenic Mice

Oligonucleotides were designed to generate a PCR fragment containing a consensus Kozak sequence and the exact zsig51 coding region. These oligonucleotides were designed with an FseI site at the 5' end and an AscI site at the 3' end to facilitate cloning into pMT12-8, a transgenic expression vector comprising the mouse MT-1 promoter and a 5' rat insulin II intron upstream of the FseI site.

PCR reactions were carried out using oligonucleotide primers designed to generate a PCR fragment containing a consensus Kozak sequence and the exact zsig51 coding region with an FseI site at the 5' end and an AscI site at the 3' end. The reaction mixtures contained 200 ng human zsig51 template and olionucleotides zc17438 (SEQ ID NO:42) and zc 17439 (SEQ ID NO:43), or mouse zsig51 template and oligonucleotides zc17950 (SEQ ID NO:44) and zc17951 (SEQ ID NO:45). PCR conditions were as follows: 95° C. for 5 minutes; 15 cycles of 95° C. for 60 seconds, 62° C. for 60 seconds, and 72° C. for 90 seconds; and 72° C. for 7 minutes. PCR products were separated by agarose gel electrophoresis and purified using a spin column containing a silica gel membrane (QIAquick™ Gel Extraction Kit; Qiagen, Inc., Valencia, Calif.). The isolated DNA fragments were digested with FseI and AscI (Boerhinger Mannheim), ethanol precipitated, and ligated into pMT12-8 that was previously digested with FseI and AscI. The pMT12-8 plasmid, designed for expression of a gene of interest in transgenic mice, contains an expression cassette flanked by 10 kb of MT-1 5' DNA and 7 kb of MT-1 3' DNA. The expression cassette comprises the mouse MT-1 promoter, a rat insulin II intron, a polylinker for the insertion of the desired clone, and the human growth hormone poly A sequence.

About one microliter of each of the ligation mixtures was electroporated into *E. coli* host cells (Electromax DH10B™ cells; obtained from Life Technologies, Inc., Gaithersburg, Md.) according to supplier's directions and plated onto LB plates containing 100 µg/ml ampicillin, and incubated overnight. Colonies were picked and grown in LB medium containing 100 µg/ml ampicillin. Miniprep DNA was prepared from the picked clones and screened for the zsig51 human or mouse insert by restriction digestion with EcoRI, and subsequent agarose gel electrophoresis. Maxipreps of the correct pMT-zsig51 constructs were prepared. A SalI fragment containing with 5' and 3' flanking sequences, the MT-1 promoter, the rat insulin II intron, zsig51 human or mouse cDNA, and the human growth hormone poly A sequence was prepared and used for microinjection into fertilized mouse oocytes to generate transgenic founder animals. The original oocytes and the sperm used to fertilize them were from F1 hybrids of C3H and C57Bl/6 mice. In subsequent generations, the mice were mated at every generation to C57Bl/6 mice. The human transgene was designated MTzsig51h, while the mouse transgene was designated MTzsig51m.

Five male and five female transgenic mice carrying MTzsig51h were identified. The expression level of the transgene in the liver of each mouse was quantified by real-time RT-PCR on an ABI Prism 7700 Sequence Detector (Perkin-Elmer). This analysis indicated that none of the males had a measurable level of expression. The expression profile of the females was: 2 very high expressors (greater than 10,000 mRNA molecules/liver cell); 1 high expressor (greater than 2,000 mRNA molecules/liver cell); 1 medium expressor (approximately 600 mRNA molecules/liver cell); and 1 low expressor (approximately 300 mRNA molecules/liver cell).

Two male and ten female transgenic mice carrying MTzsig51m were identified. The expression level of the transgene in the liver of each mouse was quantified as above. Neither of the males had a measurable level of expression. The expression profile of the females was: 5 very high expressors (greater than 10,000 mRNA molecules/liver cell); 1 high expresser (greater than 2,000 mRNA molecules/liver cell); 1 medium expresser (approximately 1,100 mRNA molecules/liver cell); 1 low expresser (approximately 300 mRNA molecules/liver cell); and 1 below the measurable level of expression.

Parameters measured included weight change, fertility, complete blood counts, serum chemistries, histology, organ weights and cell proliferation measured by incorporation of bromodeoxyuridine (BrdU). All mice received BrdU in their drinking water three days before sacrifice.

For the MTzsig51h transgenics, male animals were sacrificed at approximately two months of age, while females were sacrificed at approximately 5 months, and tissues were collected for histological analysis. Tissue samples were fixed in 10% buffered formalin, embedded in paraffin, sectioned at 3 microns, and stained with hematoxylin and eosin. The slides were examined and scored by a board-certified veterinary pathologist. Female mice were found to have scattered small areas of mineralization in the heart, lung, skeletal muscle, and the growth plate of the femur.

In the second generation of offspring that arose from matings to C57Bl/6 mice, the highest-expressing line of MTzsig51h mice gave rise to transgenic females that displayed severe hair loss at weaning.

MTzsig51M animals were sacrificed at approximately six months of age. Tissues were collected for histological analysis, fixed, examined, and scored as above. The highest expressing female MTzsig51m mouse was infertile.

Example 11

Baculovirus Expression

C-terminal Glu-Glu tagged human zsig51 is expressed in Sf9 cells using a baculovirus vector. The tagged protein comprises the peptide tag shown in (SEQ ID NO:46). The zsig51cee sequence (as a EcoRI-BamHI fragment) is inserted into a modified pFastBac™ expression vector (Life Technologies) containing the late activating Basic Protein promoter. About 90 nanograms of the zsig51 cee insert and about 150 ng of the digested vector are ligated overnight. The ligation mix is diluted 3-fold in TE (10 mM Tris-HCl, pH 7.5 and 1 mM EDTA), and 4 fmol of the diluted ligation mix is transformed into competent *E. coli* cells (Library Efficiency DH5α™ competent cells; Life Technologies, Gaithersburg, Md.) according to the manufacturer's directions by heat shock for 45 seconds in a 42° C. waterbath. The ligated DNA is diluted in 450 µl of SOC media (2% Bacto Tryptone, 0.5% Bacto Yeast Extract, 10 ml 1M NaCl, 1.5 mM KCl, 10 mM $MgCl_2$, 10 mM $MgSO_4$ and 20 mM glucose) and plated onto LB plates containing 100 µg/ml ampicillin. Clones are analyzed by restriction digests, and 1 µl of a positive clone is transformed into 20 µl *E. coli* cells (Max Efficiency DH10Bac™ competent cells; Life Technologies) according to the manufacturer's instructions, by heat shock for 45 seconds in a 42° C. waterbath. The ligated DNA is diluted in 980 µl SOC media and plated onto Luria Agar plates containing 50 µg/ml kanamycin, 7 µg/ml gentamycin, 10 µg/ml tetracycline, IPTG and Bluo Gal. The cells are incubated for 48 hours at 37° C. A color selection is used to identify those cells having virus that has incorporated into the plasmid (referred to as a "bacmid"). Those colonies, which are white in color, are picked for analysis. Bacmid DNA is isolated from positive colonies using commercially available reagents and equipment (QIAprep® 8 Miniprep Kit and QIAvac vacuum manifold; Qiagen, Inc., Valencia, Calif.) according the manufacturer's directions. Clones are screened for the correct insert by amplifying DNA using primers to the Basic Protein promoter and to the SV40 terminus via PCR. Those having the correct insert are used to transfect *Spodoptera frugiperda* (Sf9) cells.

Sf9 cells are seeded at $5 \times 10^6$ cells per 35 mm plate and allowed to attach for 1 hour at 27° C. Five microliters of bacmid DNA is diluted with 100 µl serum-free media (Sf-900 II SFM; Life Technologies). Six µl of a 1:1.5 (M/M) liposome formulation of the cationic lipid N,N',N'',N'''-tetrmethyl-N,N',N'',N'''-tetrapalmitylspermine and dioleoyl phosphatidylethanolamine in membrane-filtered water (CellFECTIN™ reagent; Life Technologies) is diluted with 100 µl Sf-900 II SFM. The bacmid DNA and lipid solutions are gently mixed and incubated 30–45 minutes at room temperature. The media from one plate of cells are aspirated, the cells are washed 1× with 2 ml fresh media. Eight hundred microliters of Sf-900 II SFM is added to the lipid-DNA mixture. The wash media is aspirated and the DNA-lipid mix added to the cells. The cells are incubated at 27° C. for 4–5 hours. The DNA-lipid mix is aspirated and 2 ml of Sf-900 II media containing penicillin/streptomycin is added to each plate. The plates are incubated at 27° C., 90% humidity, for 96 after which the virus is harvested.

Sf9 cells are grown in 50 ml Sf-900 II SFM in a 200 ml shake flask to an approximate density of $0.41–0.52 \times 10^6$ cells/ml. They are then transfected with 100µl of the virus stock from above and incubated at 27° C. for 2–3 days after which time the virus is harvested. The titer for AcCSCF1 is $1.7 \times 10^7$ pfu/ml and for AcCSNF1 it is $2.6 \times 10^7$. To scale up, $1.5 \times 10^6$ SF9 cells/ml are added to five liters of SF 900 II SFM and grown for 91 hours. The cells are then transfected with the harvested virus (MOI 0.2) and incubated as above for 71 hours.

Example 12

Protein Purification and Analysis

Glu-Glu tagged zsig51 protein (zsig51cee) was produced in baculovirus infected cells essentially as disclosed above, and the protein was purified from cell-conditioned media by affinity chromatography. A 100 ml bed volume of immobilized protein G (protein G-Sepharose®; Pharmacia Biotech) was washed 3 times with 100 ml of PBS containing 0.02% sodium azide using a 500 ml Nalgene 0.45 micron filter unit. The gel was washed with 6.0 volumes of 200 mM triethanolamine, pH 8.2 (TEA; Sigma Chemical Co., St. Louis, Mo.), and an equal volume of anti-glu-glu antibody solution containing 900 mg of antibody was added. After an overnight incubation at 4° C., unbound antibody was removed by washing the resin with 5 volumes of 200 mM TEA as described above. The resin was resuspended in 2 volumes of TEA, transferred to a suitable container, and dimethylpimilimidate-2HCl (Pierce, Rockford, Ill.), dissolved in TEA, was added to a final concentration of 36 mg/ml of gel. The gel was rocked at room temperature for 45 minutes, and the liquid was removed using the filter unit as described above. Nonspecific sites on the gel were then blocked by incubating for 10 minutes at room temperature with 5 volumes of 20 mM ethanolamine in 200 mM TEA. The gel was washed with 5 volumes of PBS containing 0.02% sodium azide and stored in this solution at 4° C.

Unless otherwise noted, all purification steps were carried out at 4° C. A mixture of protease inhibitors was added to a 2 liter sample of conditioned media from baculovirus-infected Sf9 cells to final concentrations of 2.5 mM ethylenediaminetetraacetic acid (EDTA, Sigma Chemical Co., St. Louis, Mo.), 0.001 mM leupeptin (Boehringer-Mannheim, Indianapolis, Ind.), 0.001 mM pepstatin (Boehringer-Mannheim) and 0.4 mM 4-(2-Aminoethyl)-benzenesulfonyl fluoride hydrochloride (Pefabloc®; Boehringer-Mannheim). The sample was centrifuged at 10,000 rpm for 30 min at 4° C. in a Beckman JLA-10.5 rotor (Beckman Instruments) in a Beckman Avanti J25I centrifuge (Beckman Instruments) to remove cell debris. To the supernatant fraction was added a 50.0 ml sample of anti-EE Sepharose, prepared as described above, and the mixture was gently agitated on a Wheaton (Millville, N.J.) roller culture apparatus for 18.0 h at 4° C.

The mixture was poured into a 5.0×20.0 cm column (Econo-Column®; Bio-Rad Laboratories, Hercules, Calif.), and the gel was washed with 30 column volumes of phosphate buffered saline (PBS). The unretained flow-through fraction was discarded. Once the absorbance of the effluent at 280 nM was less than 0.05, flow through the column was reduced to zero and the anti-EE Sepharose gel was washed with 2.0 column volumes of PBS containing 0.2 mg/ml of EE peptide having the sequence Glu-Tyr-Met-Pro-Val-Asp (SEQ ID NO:47) (AnaSpec, San Jose, Calif.). After 1.0 hour at 4° C., flow was resumed and the eluted protein was collected. This fraction was referred to as the peptide elution. The anti-EE Sepharose gel was washed with 2.0 column volumes of 0.1 M glycine, pH 2.5, and the glycine wash was collected separately. The pH of the glycine-eluted fraction was adjusted to 7.0 by the addition of a small volume of 10×PBS and stored at 4° C.

The peptide elution was concentrated to 5.0 ml using a 5,000 molecular weight cutoff membrane concentrator (Millipore, Bedford, Mass.) according to the manufacturer's instructions. The concentrated peptide elution was separated from free peptide by chromatography on a 1.5×50 cm Sephadex® G-50 (Pharmacia Biotech) column equilibrated in PBS at a flow rate of 1.0 ml/min using a commercially available HPLC system (BioCad™/Sprint™ HPLC system; PerSeptive BioSystems, Framingham, Mass.). Two-ml fractions were collected and the absorbance at 280 nM was monitored. The first peak of material absorbing at 280 nM and eluting near the void volume of the column was collected. This material represented purified zsig51cee. The material was aliquoted and stored at −80° C.

The N-terminal peptide of the recombinant zsig51cee was identified by mass spectrometry. Two forms were found. The first had a mass of 2000.8, which indicated an N-terminal peptide with a pyro-glutamic acid instead of glutamine (residue 1 of SEQ ID NO:2). The second form had a mass of 3038, corresponding to the first peptide with glycosylation consisting of 2HexNAc, 3Hex, and 1 deoxyhex.

Example 13

Expression of Zsiq51 in Mammalian Cells

A mammalian expression vector was constructed with the dihyrofolate reductase gene under control of the SV40 early promoter and SV40 polyadenylation site, and a cloning site to insert the gene of interest under control of the mouse MT-1 promoter and the hGH polyadenylation site. The expression vector was designated pZP-9 and was deposited at the American Type Culture Collection, 12301 Parklawn Drive, Rockville, Md. on Feb. 20, 1998 under Accession Number 98668. To facilitate purification of the protein of interest, the pZP-9 vector was modified by addition of the tPA leader sequence (U.S. Pat. No. 5,641,655, incorporated herein by reference) and a GluGlu tag (SEQ ID NO:46) between the MT-1 promoter and hGH terminator. Expression results in an N-terminally tagged fusion protein comprising the tPA leader. The N-terminally tagged vector was designated pZP9NEE. The zsig51 sequence was ligated into the vector as a BamHI-XbaI fragment, and resulting construct was designated pZP9/zsig51NEE.

BHK570 cells (ATCC CRL 10314) were plated on 10-cm tissue culture dishes and allowed to grow to approximately 50 to 70% confluency overnight. Unless otherwise specified the cells were handled using standard aseptic technique, grown at 37° C., 5% $CO_2$, in water-jacketed incubators (Model 3110; Forma Scientific, Marietta, Ohio), and with the following media: DMEM (High Glucose, #11965-092; Life Technologies, Gaithersburg, Md.), 5% Fetal Bovine Serum (Hyclone, Logan, Utah), 1% L-Glutamine (JRH Biosciences, Lexena, Kans.), 1% sodium pyruvate (Life Technologies). The cells were transfected with plasmid pZP9/zsig51NEE, using a 3:1 (w/w) liposome formulation of the polycationic lipid 2,3-dioleyloxy-N-[2 (sperminecarboxamido)ethyl]-N,N-dimethyl-1-propaniminium-trifluoroacetate and the neutral lipid dioleoyl phosphatidylethanolamine in membrane-filtered water (Lipofectamine™ Reagent; Life Technologies), in a serum-free (SF) media formulation (DMEM, 10 mg/ml transferrin, 5 mg/ml insulin, 1 mg/ml fetuin, 1% L-Glutamine (JRH #59202-77P), 1% sodium pyruvate. 16 µg of plasmid was diluted in a 15-ml tube with 640 µl SF media, and in a separate tube, 35 µl of Lipofectamine™ was mixed with 605 µl of SF media. The Lipofectamine™ mix was added to the DNA mix and allowed to incubate approximately 30 minutes at room temperature. Five ml of SF medium was added to the DNA:Lipofectamine™ mixture. The cells were rinsed once with 5 ml of SF medium, aspirated, and the DNA:Lipofectamine™ mixture was added. The cells were incubated at 37° C. for five hours, then 6.4 ml of 10% FBS/DMEM medium was added to the plate. The plate was incubated at 37° C. overnight, and the DNA:Lipofectamine™ mixture was replaced with fresh medium the next day. On day 2 after transfection, the cells were split into transfection media (standard media plus 1 μM methotrexate) in 150-mm plates at 1:50, 1:100, and 1:200. The plates were re-fed at day 5 following transfection with fresh selection medium. Once resistant colonies reached 3–4 mm in diameter, a plate containing 70 to 150 colonies was selected for immunoassay.

The plate of cells was rinsed with 10 ml SF media, then 5 ml SF media is added, followed by a nylon mesh, then a notched nitrocellulose filter, both pre-soaked in SF media. Matching alignment marks were made on the plate, and it was incubated for approximately 5 hours at 37° C. The filter and mesh were removed, and the cells were re-fed standard media plus penicillin-streptomycin-neomycin antibiotic mix (Life Technologies) and incubated at 37° C. The filter was incubated with anti-GluGlu antibody conjugated to horseradish peroxidase, at 1:5000 dilution, in 2.5% non-fat dry milk Western A buffer for 1 hour at room temperature on a rotating shaker. The filter was washed three times at room temperature in PBS plus 0.01% Tween 20, 15 minutes per wash. The filter was developed with commercially available reagents (ECL™ Western blotting detection reagents; Amersham Life Science Inc., Arlington Heights, Ill.) according to the manufacturer's directions and exposed to film (Hyperfilm™ ECL, Amersham) for approximately 5 minutes. The alignment marks on the filter were transferred to the film.

The film was aligned with the marks on the plate of cells for selection of colonies with optimal signals. The colonies were circled and the media was removed from the plate. Sterile 3-mm cloning discs (PGM Scientific Corporation) soaked in trypsin were placed on the colonies, then transferred to 200 μl of selection media in a 96-well dish. A series of seven, two-fold serial dilutions was carried out with the cells recovered from the disc. The cells were grown for one week at 37° C., then expanded by selecting the well with the lowest dilution of cells at confluency for each clone for trypsinization and transferring ir to a 12 well dish containing selection media.

The clones were expanded directly from the 12-well dish to two T75 flasks for each clone. One flask was maintained in selection media at 37° C. The other flask was used for Western blot analysis of the clones. The flask was first grown to confluency, then the medium was changed to SF, allowed to incubate for two days at 37° C., harvested, and filtered at 0.22 μm. This flask is discarded after harvest.

The conditioned medium was concentrated 10-fold by ultrafiltration, and analyzed by Western blot. Three clones producing the highest levels of protein were selected and samples were frozen. The clones are pooled and transferred for large scale culture.

Example 14

Expression Analysis by Quantitative RT-PCR

The expression level of zsig51 mRNA in a variety of human and mouse tissues was quantified by real-time PCR (RT-PCR) on an ABI Prism 7700 Sequence Detector (Perkin-Elmer, Norwalk, Conn.) following the manufacturer's protocols. Total RNA was prepared from fresh mouse tissues using a commercially available kit (RNeasy® kit; Qiagen). Human total RNA samples were purchased from a variety of commercial sources (Invitrogen, Clontech).

Expression of zsig51 mRNA in the pancreas of diabetic NOD mice was found to be significantly higher than in the pancreas of non-diabetic NOD mice. Expression of zsig51 in the pancreas of fasted mice was found to be lower than in the pancreas of well-fed mice. Expression of zsig51 in the mouse eye was found to be approximately 50-fold higher than expression in normal pancreas.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

We claim:
1. An isolated polypeptide comprised of the amino acid sequence of residues 1 through 106 of SEQ ID NO: 2.

* * * * *

SEQUENCE LISTING

```
<160> NUMBER OF SEQ ID NOS:  49

<210> SEQ ID NO 1
<211> LENGTH: 746
<212> TYPE: DNA
<213> ORGANISM: Homo sapiens
<220> FEATURE:
<221> NAME/KEY: CDS
<222> LOCATION: (56)...(445)
<221> NAME/KEY: sig_peptide
<222> LOCATION: (56)...(124)

<400> SEQUENCE: 1
ccagcaggag gcacaggaaa actgcaagcc gctctgttcc tgggcctcgg aagtg atg        58
                                                                  Met cct atg gcg tcc cct caa acc ctg gtc ctc tat ctg ctg gtc ctg gca       106
Pro Met Ala Ser Pro Gln Thr Leu Val Leu Tyr Leu Leu Val Leu Ala
        -20                 -15                 -10 gtc act gaa gcc tgg ggc cag gag gca gtc atc cca ggc tgc cac ttg       154
Val Thr Glu Ala Trp Gly Gln Glu Ala Val Ile Pro Gly Cys His Leu
```

-continued

```
        -5                  1                  5                        10
cac ccc ttc aat gtg aca gtg cga agt gac cgc caa ggc acc tgc cag         202
His Pro Phe Asn Val Thr Val Arg Ser Asp Arg Gln Gly Thr Cys Gln
                    15                  20                  25 ggc tcc cac gtg gca cag gcc tgt gtg ggc cac tgt gag tcc agc gcc         250
Gly Ser His Val Ala Gln Ala Cys Val Gly His Cys Glu Ser Ser Ala
            30                  35                  40 ttc cct tct cgg tac tct gtg ctg gtg gcc agt ggt tac cga cac aac         298
Phe Pro Ser Arg Tyr Ser Val Leu Val Ala Ser Gly Tyr Arg His Asn
        45                  50                  55 atc acc tcc gtc tct cag tgc tgc acc atc agt ggc ctg aag aag gtc         346
Ile Thr Ser Val Ser Gln Cys Cys Thr Ile Ser Gly Leu Lys Lys Val
    60                  65                  70 aaa gta cag ctg cag tgt gtg ggg agc cgg agg gag gag ctc gag atc         394
Lys Val Gln Leu Gln Cys Val Gly Ser Arg Arg Glu Glu Leu Glu Ile
75                  80                  85                  90 ttc acg gcc agg gcc tgc cag tgt gac atg tgt cgc ctc tct cgc tac         442
Phe Thr Ala Arg Ala Cys Gln Cys Asp Met Cys Arg Leu Ser Arg Tyr
                95                  100                 105 tag cccatcctct ccctccttc ctccctggg tcacagggct tgacattctg                495
gtgggggaaa cctgtgttca agattcaaaa actggaagga gctccagccc tgatggttac       555
ttgctatgga atttttttaa ataaggggag ggttgttcca gctttgatcc tttgtaagat       615
tttgtgactg tcacctgaga agagggagt ttctgcttct tccctgcctc tgcctggccc        675
ttctaaacca atctttcatc attttacttc cctctttgcc cttaccccta aataaagcaa       735
gcagttcttg a                                                            746
```

<210> SEQ ID NO 2
<211> LENGTH: 129
<212> TYPE: PRT
<213> ORGANISM: Homo sapiens
<220> FEATURE:
<221> NAME/KEY: SIGNAL
<222> LOCATION: (1)...(23)

<400> SEQUENCE: 2

```
Met Pro Met Ala Ser Pro Gln Thr Leu Val Leu Tyr Leu Leu Val Leu
            -20                 -15                 -10

Ala Val Thr Glu Ala Trp Gly Gln Glu Ala Val Ile Pro Gly Cys His
    -5                  1                   5

Leu His Pro Phe Asn Val Thr Val Arg Ser Asp Arg Gln Gly Thr Cys
10                  15                  20                  25

Gln Gly Ser His Val Ala Gln Ala Cys Val Gly His Cys Glu Ser Ser
                30                  35                  40

Ala Phe Pro Ser Arg Tyr Ser Val Leu Val Ala Ser Gly Tyr Arg His
            45                  50                  55

Asn Ile Thr Ser Val Ser Gln Cys Cys Thr Ile Ser Gly Leu Lys Lys
        60                  65                  70

Val Lys Val Gln Leu Gln Cys Val Gly Ser Arg Arg Glu Glu Leu Glu
    75                  80                  85

Ile Phe Thr Ala Arg Ala Cys Gln Cys Asp Met Cys Arg Leu Ser Arg
90                  95                  100                 105

Tyr
```

<210> SEQ ID NO 3
<211> LENGTH: 109
<212> TYPE: PRT

-continued

<213> ORGANISM: Artificial Sequence
<220> FEATURE:
<221> NAME/KEY: VARIANT
<222> LOCATION: (2)...(26)
<223> OTHER INFORMATION: Xaa is any amino acid
<221> NAME/KEY: VARIANT
<222> LOCATION: (27)...(34)
<223> OTHER INFORMATION: Xaa is any amino acid or not present
<221> NAME/KEY: VARIANT
<222> LOCATION: (36)...(36)
<223> OTHER INFORMATION: Xaa = any amino acid
<221> NAME/KEY: VARIANT
<222> LOCATION: (38)...(38)
<223> OTHER INFORMATION: Xaa = any amino acid
<221> NAME/KEY: VARIANT
<222> LOCATION: (40)...(54)
<223> OTHER INFORMATION: Xaa is any amino acid
<221> NAME/KEY: VARIANT
<222> LOCATION: (55)...(72)
<223> OTHER INFORMATION: Xaa is any amino acid or not present
<221> NAME/KEY: VARIANT
<222> LOCATION: (74)...(93)
<223> OTHER INFORMATION: Xaa is any amino acid
<221> NAME/KEY: VARIANT
<222> LOCATION: (94)...(106)
<223> OTHER INFORMATION: Xaa is any amino acid or not present
<221> NAME/KEY: VARIANT
<222> LOCATION: (108)...(108)
<223> OTHER INFORMATION: Xaa = any amino acid
<223> OTHER INFORMATION: polypeptide motif

<400> SEQUENCE: 3

```
Cys Xaa Xaa Xaa Xaa Xaa Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa Xaa Xaa Xaa Xaa
            20                  25                  30

Xaa Xaa Cys Xaa Gly Xaa Cys Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Cys Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Cys Xaa Cys
            100                 105
```

<210> SEQ ID NO 4
<211> LENGTH: 387
<212> TYPE: DNA
<213> ORGANISM: Artificial Sequence
<220> FEATURE:
<221> NAME/KEY: sig_peptide
<222> LOCATION: (1)...(69)
<223> OTHER INFORMATION: degenerate sequence
<221> NAME/KEY: variation
<222> LOCATION: (1)...(387)
<223> OTHER INFORMATION: n is any nucleotide

<400> SEQUENCE: 4

```
atgccnatgg cnwsnccnca racnytngtn ytntayytny tngtnytngc ngtnacngar     60
gcntggggnc argargcngt nathccnggn tgycayytnc ayccnttyaa ygtnacngtn    120
mgnwsngaym gncarggnac ntgycarggn wsncaygtng cncargcntg ygtnggncay    180
tgygarwsnw sngcnttycc nwsnmgntay wsngtnytng tngcnwsngg ntaymgncay    240
aayathacnw sngtnwsnca rtgytgyacn athwsnggny tnaaraargt naargtncar    300
```

```
ytncartgyg tnggnwsnmg nmgngargar ytngaratht tyacngcnmg ngcntgycar      360
tgygayatgt gymgnytnws nmgntay                                         387
```

<210> SEQ ID NO 5
<211> LENGTH: 17
<212> TYPE: DNA
<213> ORGANISM: Artificial Sequence
<220> FEATURE:
<223> OTHER INFORMATION: oligonucleotide primer
<221> NAME/KEY: variation
<222> LOCATION: (1)...(17)
<223> OTHER INFORMATION: n is any nucleotide

<400> SEQUENCE: 5

```
cntgygtngg ncaytgy                                                    17
```

<210> SEQ ID NO 6
<211> LENGTH: 17
<212> TYPE: DNA
<213> ORGANISM: Artificial Sequence
<220> FEATURE:
<223> OTHER INFORMATION: oligonucleotide primer
<221> NAME/KEY: variation
<222> LOCATION: (1)...(17)
<223> OTHER INFORMATION: n is any nucleotide

<400> SEQUENCE: 6

```
nntgydnngg nbvntgy                                                    17
```

<210> SEQ ID NO 7
<211> LENGTH: 17
<212> TYPE: DNA
<213> ORGANISM: Artificial Sequence
<220> FEATURE:
<223> OTHER INFORMATION: oligonucleotide primer
<221> NAME/KEY: variation
<222> LOCATION: (1)...(17)
<223> OTHER INFORMATION: n is any nucleotide

<400> SEQUENCE: 7

```
nnacrhnncc nvbnacr                                                    17
```

<210> SEQ ID NO 8
<211> LENGTH: 17
<212> TYPE: DNA
<213> ORGANISM: Artificial Sequence
<220> FEATURE:
<223> OTHER INFORMATION: oligonucleotide primer
<221> NAME/KEY: variation
<222> LOCATION: (1)...(17)
<223> OTHER INFORMATION: n is any nucleotide

<400> SEQUENCE: 8

```
mgngcntgyc artgyga                                                    17
```

<210> SEQ ID NO 9
<211> LENGTH: 17
<212> TYPE: DNA
<213> ORGANISM: Artificial Sequence
<220> FEATURE:
<223> OTHER INFORMATION: oligonucleotide primer
<221> NAME/KEY: variation
<222> LOCATION: (1)...(17)
<223> OTHER INFORMATION: n is any nucleotide

<400> SEQUENCE: 9

```
nnnnvntgyv rntgydv                                                    17
```

```
<210> SEQ ID NO 10
<211> LENGTH: 17
<212> TYPE: DNA
<213> ORGANISM: Artificial Sequence
<220> FEATURE:
<223> OTHER INFORMATION: oligonucleotide primer
<221> NAME/KEY: variation
<222> LOCATION: (1)...(17)
<223> OTHER INFORMATION: n is any nucleotide

<400> SEQUENCE: 10
nnnnbnacrb ynacrhb                                                17

<210> SEQ ID NO 11
<211> LENGTH: 17
<212> TYPE: DNA
<213> ORGANISM: Artificial Sequence
<220> FEATURE:
<223> OTHER INFORMATION: oligonucleotide primer

<400> SEQUENCE: 11
tgycartgyg ayatgtg                                                17

<210> SEQ ID NO 12
<211> LENGTH: 17
<212> TYPE: DNA
<213> ORGANISM: Artificial Sequence
<220> FEATURE:
<223> OTHER INFORMATION: oligonucleotide primer
<221> NAME/KEY: variation
<222> LOCATION: (1)...(17)
<223> OTHER INFORMATION: n is any nucleotide

<400> SEQUENCE: 12
tgycantgyg anrwrtg                                                17

<210> SEQ ID NO 13
<211> LENGTH: 17
<212> TYPE: DNA
<213> ORGANISM: Artificial Sequence
<220> FEATURE:
<223> OTHER INFORMATION: oligonucleotide primer
<221> NAME/KEY: variation
<222> LOCATION: (1)...(17)
<223> OTHER INFORMATION: n is any nucleotide

<400> SEQUENCE: 13
acrgtnacrc tnywyac                                                17

<210> SEQ ID NO 14
<211> LENGTH: 17
<212> TYPE: DNA
<213> ORGANISM: Artificial Sequence
<220> FEATURE:
<223> OTHER INFORMATION: oligonucleotide primer
<221> NAME/KEY: variation
<222> LOCATION: (1)...(17)
<223> OTHER INFORMATION: n is any nucleotide

<400> SEQUENCE: 14
cntgygtngg ncaytgy                                                17

<210> SEQ ID NO 15
<211> LENGTH: 17
<212> TYPE: DNA
<213> ORGANISM: Artificial Sequence
<220> FEATURE:
<223> OTHER INFORMATION: oligonucleotide primer
```

```
<221> NAME/KEY: variation
<222> LOCATION: (1)...(17)
<223> OTHER INFORMATION: n is any nucleotide

<400> SEQUENCE: 15
sntgygwngg ncaytgy                                              17

<210> SEQ ID NO 16
<211> LENGTH: 17
<212> TYPE: DNA
<213> ORGANISM: Artificial Sequence
<220> FEATURE:
<223> OTHER INFORMATION: oligonucleotide primer
<221> NAME/KEY: variation
<222> LOCATION: (1)...(17)
<223> OTHER INFORMATION: n is any nucleotide

<400> SEQUENCE: 16
snacrcwncc ngtracr                                              17

<210> SEQ ID NO 17
<211> LENGTH: 17
<212> TYPE: DNA
<213> ORGANISM: Artificial Sequence
<220> FEATURE:
<223> OTHER INFORMATION: oligonucleotide primer
<221> NAME/KEY: variation
<222> LOCATION: (1)...(17)
<223> OTHER INFORMATION: n is any nucleotide

<400> SEQUENCE: 17
wsncartgyt gyacnat                                              17

<210> SEQ ID NO 18
<211> LENGTH: 17
<212> TYPE: DNA
<213> ORGANISM: Artificial Sequence
<220> FEATURE:
<223> OTHER INFORMATION: oligonucleotide primer
<221> NAME/KEY: variation
<222> LOCATION: (1)...(17)
<223> OTHER INFORMATION: n is any nucleotide

<400> SEQUENCE: 18
wsncantgyt gymsnmy                                              17

<210> SEQ ID NO 19
<211> LENGTH: 17
<212> TYPE: DNA
<213> ORGANISM: Artificial Sequence
<220> FEATURE:
<223> OTHER INFORMATION: oligonucleotide primer
<221> NAME/KEY: variation
<222> LOCATION: (1)...(17)
<223> OTHER INFORMATION: n is any nucleotide

<400> SEQUENCE: 19
wsngtnacra crksnkr                                              17

<210> SEQ ID NO 20
<211> LENGTH: 17
<212> TYPE: DNA
<213> ORGANISM: Artificial Sequence
<220> FEATURE:
<223> OTHER INFORMATION: oligonucleotide primer
<221> NAME/KEY: variation
<222> LOCATION: (1)...(17)
<223> OTHER INFORMATION: n is any nucleotide
```

```
<400> SEQUENCE: 20 caycnttya aygtnac                                                    17

<210> SEQ ID NO 21
<211> LENGTH: 17
<212> TYPE: DNA
<213> ORGANISM: Artificial Sequence
<220> FEATURE:
<223> OTHER INFORMATION: oligonucleotide primer
<221> NAME/KEY: variation
<222> LOCATION: (1)...(17)
<223> OTHER INFORMATION: n is any nucleotide

<400> SEQUENCE: 21
mrncmnywyw aygtnrm                                                   17

<210> SEQ ID NO 22
<211> LENGTH: 17
<212> TYPE: DNA
<213> ORGANISM: Artificial Sequence
<220> FEATURE:
<223> OTHER INFORMATION: oligonucleotide primer
<221> NAME/KEY: variation
<222> LOCATION: (1)...(17)
<223> OTHER INFORMATION: n is any nucleotide

<400> SEQUENCE: 22
kyngknrwrw trcanyk                                                   17

<210> SEQ ID NO 23
<211> LENGTH: 48
<212> TYPE: DNA
<213> ORGANISM: Artificial Sequence
<220> FEATURE:
<223> OTHER INFORMATION: oligonucleotide primer

<400> SEQUENCE: 23
gtctgggttc gctactcgag gcggccgcta tttttttttt tttttttt                 48

<210> SEQ ID NO 24
<211> LENGTH: 472
<212> TYPE: DNA
<213> ORGANISM: Artificial Sequence
<220> FEATURE:
<223> OTHER INFORMATION: expressed sequence tag

<400> SEQUENCE: 24
ccagcaggag gcacaggaaa actgcaagcc gctctgttcc tgggcctcgg aagtgatgcc    60
tatggcgtcc cctcaaaccc tggtcctcta tctgctggtc ctgcagtcac ctgaagcctg   120
gggccaggag gcagtcatcc caggctgcca cttgcacccc ttcaatgtga cagtgcgaag   180
tgaccgccaa ggncacctgc cagggctccc acgtggcaca ggcctgtgtg ggccactgtg   240
agtccagcgc cttcccttct cggtactctg tgctggtggc cagtggttac cgacacaaca   300
tcacctccgt ctctcagtgc tgcaccatca gtggcctgaa gaagtcaaag tacagctgca   360
gtgtgtgggg agccggaggg aggagtcgag atcttcaggc cagggctgcc atgtgacatg   420
tgtcgcctct ctcgctacta gcccatcctc tccctccttt cctcccctgg gg          472

<210> SEQ ID NO 25
<211> LENGTH: 22
<212> TYPE: DNA
<213> ORGANISM: Artificial Sequence
<220> FEATURE:
<223> OTHER INFORMATION: oligonucleotide primer
```

```
<400> SEQUENCE: 25
ccagcacaga gtaccgagaa gg                                              22

<210> SEQ ID NO 26
<211> LENGTH: 22
<212> TYPE: DNA
<213> ORGANISM: Artificial Sequence
<220> FEATURE:
<223> OTHER INFORMATION: oligonucleotide primer

<400> SEQUENCE: 26
tggtcctggc agtcactgaa gc                                              22

<210> SEQ ID NO 27
<211> LENGTH: 18
<212> TYPE: DNA
<213> ORGANISM: Artificial Sequence
<220> FEATURE:
<223> OTHER INFORMATION: oligonucleotide primer

<400> SEQUENCE: 27
ggcctgccag tgtgacat                                                   18

<210> SEQ ID NO 28
<211> LENGTH: 18
<212> TYPE: DNA
<213> ORGANISM: Artificial Sequence
<220> FEATURE:
<223> OTHER INFORMATION: oligonucleotide primer

<400> SEQUENCE: 28
cccccaccag aatgtcaa                                                   18

<210> SEQ ID NO 29
<211> LENGTH: 129
<212> TYPE: PRT
<213> ORGANISM: Artificial Sequence
<220> FEATURE:
<221> NAME/KEY: SIGNAL
<222> LOCATION: (1)...(23)
<223> OTHER INFORMATION: engineered variant

<400> SEQUENCE: 29

Met Pro Met Ala Ser Pro Gln Thr Leu Val Leu Tyr Leu Leu Val Leu
            -20                 -15                 -10

Ala Val Thr Glu Ala Trp Gly Gln Glu Ala Val Ile Pro Gly Cys His
         -5                   1               5

Leu His Pro Phe Asn Val Thr Val Arg Ser Asp Arg Gln Gly Thr Cys
 10                  15                  20                  25

Gln Gly Ser His Val Ala Gln Ala Cys Val Gly His Cys Glu Ser Ser
                 30                  35                  40

Ala Phe Pro Ser Arg Tyr Ser Val Leu Val Ala Ser Gly Tyr Arg His
             45                  50                  55

Asn Ile Thr Ser Val Ser Gln Cys Cys Thr Ile Ser Gly Leu Lys Lys
         60                  65                  70

Val Lys Val Gln Leu Gln Cys Val Gly Ser Arg Arg Glu Glu Leu Glu
     75                  80                  85

Ile Phe Thr Ala Arg Ser Cys Gln Cys Asp Met Cys Arg Leu Ser Arg
 90                  95                 100                 105

Tyr
```

-continued

```
<210> SEQ ID NO 30
<211> LENGTH: 387
<212> TYPE: DNA
<213> ORGANISM: Artificial Sequence
<220> FEATURE:
<223> OTHER INFORMATION: degenerate sequence
<221> NAME/KEY: variation
<222> LOCATION: (1)...(387)
<223> OTHER INFORMATION: n is any nucleotide

<400> SEQUENCE: 30
atgccnatgg cnwsnccnca racnytngtn ytntayytny tngtnytngc ngtnacngar     60
gcntggggnc argargcngt nathccnggn tgycayytnc ayccnttyaa ygtnacngtn    120
mgnwsngaym gncarggnac ntgycarggn wsncaygtng cncargcntg ygtnggncay    180
tgygarwsnw sngcnttycc nwsnmgntay wsngtnytng tngcnwsngg ntaymgncay    240
aayathacnw sngtnwsnca rtgytgyacn athwsnggny tnaaraargt naargtncar    300
ytncartgyg tnggnwsnmg nmgngargar ytngaratht tyacngcnmg nwsntgycar    360
tgygayatgt gymgnytnws nmgntay                                        387

<210> SEQ ID NO 31
<211> LENGTH: 589
<212> TYPE: DNA
<213> ORGANISM: Mus musculus
<220> FEATURE:
<221> NAME/KEY: CDS
<222> LOCATION: (36)...(422)

<400> SEQUENCE: 31
ggagtcttca gttgctgttg gactgtcctt tgcag atg ccc atg gca cca cga       53
                                       Met Pro Met Ala Pro Arg
                                        1               5 gtc ttg ctc ctt tgc ctg ctg ggc ctg gca gtc act gaa ggg cat agc     101
Val Leu Leu Leu Cys Leu Leu Gly Leu Ala Val Thr Glu Gly His Ser
             10                  15                  20 cca gag aca gcc atc cca ggc tgc cac ttg cac ccc ttc aat gtg acg     149
Pro Glu Thr Ala Ile Pro Gly Cys His Leu His Pro Phe Asn Val Thr
         25                  30                  35 gtg cgc agt gat cgc ctc ggc act tgc cag ggc tcc cac gtg gca cag     197
Val Arg Ser Asp Arg Leu Gly Thr Cys Gln Gly Ser His Val Ala Gln
     40                  45                  50 gcc tgt gta gga cac tgt gag tct agt gct ttc cct tcc cgg tac tct     245
Ala Cys Val Gly His Cys Glu Ser Ser Ala Phe Pro Ser Arg Tyr Ser
 55                  60                  65                  70 gtg ctg gtg gcc agt ggc tat cgg cac aac atc acc tct tcc tcc cag     293
Val Leu Val Ala Ser Gly Tyr Arg His Asn Ile Thr Ser Ser Ser Gln
                 75                  80                  85 tgc tgc acc atc agc agc ctc aga aag gtg agg gtg tgg ctg cag tgc     341
Cys Cys Thr Ile Ser Ser Leu Arg Lys Val Arg Val Trp Leu Gln Cys
             90                  95                 100 gtg ggg aac cag cgt ggg gag ctt gag atc ttt act gca agg gcc tgc     389
Val Gly Asn Gln Arg Gly Glu Leu Glu Ile Phe Thr Ala Arg Ala Cys
        105                 110                 115 cag tgt gat atg tgc cgt ttc tcc cgc tac tag tccccgaagg gctcaggctc    442
Gln Cys Asp Met Cys Arg Phe Ser Arg Tyr  *
    120                 125 cggtcctgcc actgacatgt catgggtatc tcaaactcgg ggctctgacc ctctttatcg    502
tctgtgaaga tgaggttggc cctctcagca gtctccttgc tacattcttc cttcgctcct    562
gtcctcaata aagcaagcaa tgcttga                                        589
```

<210> SEQ ID NO 32
<211> LENGTH: 128
<212> TYPE: PRT
<213> ORGANISM: Mus musculus

<400> SEQUENCE: 32

```
Met Pro Met Ala Pro Arg Val Leu Leu Cys Leu Leu Gly Leu Ala
 1               5                  10                  15

Val Thr Glu Gly His Ser Pro Glu Thr Ala Ile Pro Gly Cys His Leu
                20                  25                  30

His Pro Phe Asn Val Thr Val Arg Ser Asp Arg Leu Gly Thr Cys Gln
            35                  40                  45

Gly Ser His Val Ala Gln Ala Cys Val Gly His Cys Glu Ser Ser Ala
 50                  55                  60

Phe Pro Ser Arg Tyr Ser Val Leu Val Ala Ser Gly Tyr Arg His Asn
65                  70                  75                  80

Ile Thr Ser Ser Gln Cys Cys Thr Ile Ser Ser Leu Arg Lys Val
                85                  90                  95

Arg Val Trp Leu Gln Cys Val Gly Asn Gln Arg Gly Glu Leu Glu Ile
                100                 105                 110

Phe Thr Ala Arg Ala Cys Gln Cys Asp Met Cys Arg Phe Ser Arg Tyr
                115                 120                 125
```

<210> SEQ ID NO 33
<211> LENGTH: 47
<212> TYPE: DNA
<213> ORGANISM: Artificial Sequence
<220> FEATURE:
<223> OTHER INFORMATION: oligonucleotide primer

<400> SEQUENCE: 33
gtcggtgctc agcattcact actcgagggt ttttttttt tttttt         47

<210> SEQ ID NO 34
<211> LENGTH: 18
<212> TYPE: DNA
<213> ORGANISM: Artificial Sequence
<220> FEATURE:
<223> OTHER INFORMATION: oligonucleotide primer

<400> SEQUENCE: 34
cctgggcctc ggaagtga         18

<210> SEQ ID NO 35
<211> LENGTH: 18
<212> TYPE: DNA
<213> ORGANISM: Artificial Sequence
<220> FEATURE:
<223> OTHER INFORMATION: oligonucleotide primer

<400> SEQUENCE: 35
aaactcccct cttctcag         18

<210> SEQ ID NO 36
<211> LENGTH: 30
<212> TYPE: DNA
<213> ORGANISM: Artificial Sequence
<220> FEATURE:
<223> OTHER INFORMATION: oligonucleotide primer

<400> SEQUENCE: 36

-continued

```
cgtaatacga ctcactatag ggcgaattgg                                         30

<210> SEQ ID NO 37
<211> LENGTH: 27
<212> TYPE: DNA
<213> ORGANISM: Artificial Sequence
<220> FEATURE:
<223> OTHER INFORMATION: oligonucleotide primer

<400> SEQUENCE: 37
gaaacagcta tgaccatgat tacgcca                                            27

<210> SEQ ID NO 38
<211> LENGTH: 767
<212> TYPE: DNA
<213> ORGANISM: Rattus norvegicus
<220> FEATURE:
<221> NAME/KEY: CDS
<222> LOCATION: (203)...(595)

<400> SEQUENCE: 38
gcaggaggca cctggagtct acagttcctg ccggactgag tagctgaggc aaggaagcaa        60
gcaccccaca cattcccacc caaggcagag aggatcaaca gtgccaccca ggcacacctc       120
acagtcggaa gacccagaag cctggcttgc tggggagaga cacaactgc  aaagacttcc       180 cttcccaccc actccttttc ag atg ccc atg gca cct cga gtc ttg ctc ttc        232
                         Met Pro Met Ala Pro Arg Val Leu Leu Phe
                           1               5                  10 tgc ctg ctg ggt ctg gca gtc act gaa ggg cat ggc ctg gag gca gcc         280
Cys Leu Leu Gly Leu Ala Val Thr Glu Gly His Gly Leu Glu Ala Ala
             15                  20                  25 gtc cca atc cca ggc tgc cac ttg cac ccc ttt aac gtg aca gtg cga         328
Val Pro Ile Pro Gly Cys His Leu His Pro Phe Asn Val Thr Val Arg
         30                  35                  40 agt gat cgc cat ggc acc tgc cag ggc tcc cat gtg gca cag gcg tgt         376
Ser Asp Arg His Gly Thr Cys Gln Gly Ser His Val Ala Gln Ala Cys
     45                  50                  55 gta gga cac tgt gag tct agt gct ttc cct tct cgg tac tct gtg ctg         424
Val Gly His Cys Glu Ser Ser Ala Phe Pro Ser Arg Tyr Ser Val Leu
 60                  65                  70 gtt gcc agt ggc tat cga cac aac atc acc tct gtc tct cag tgc tgt         472
Val Ala Ser Gly Tyr Arg His Asn Ile Thr Ser Val Ser Gln Cys Cys
 75                  80                  85                  90 acc atc agc agc ctt aaa aag gtg agg gtg tgg ctg cac tgc gtg ggg         520
Thr Ile Ser Ser Leu Lys Lys Val Arg Val Trp Leu His Cys Val Gly
                 95                 100                 105 aac cag cgt ggg gag ctc gag atc ttc acg gct agg gcc tgc cag tgt         568
Asn Gln Arg Gly Glu Leu Glu Ile Phe Thr Ala Arg Ala Cys Gln Cys
            110                 115                 120 gat atg tgc cgt ctc tcc cgc tac tag gccccgaagg gctcaggcct               615
Asp Met Cys Arg Leu Ser Arg Tyr *
        125                 130 ccagtcctgc cactgatagg tcgtgcttct ctcagaccag ccctctttgg agtctgaaga       675
tggggcttcg cctctgttta cctggcctcc tcagcagtct cactgctgct ttctccttca       735
cccctgtcct caataaagca ggcagtgctt ga                                    767

<210> SEQ ID NO 39
<211> LENGTH: 130
<212> TYPE: PRT
<213> ORGANISM: Rattus norvegicus
```

```
<400> SEQUENCE: 39

Met Pro Met Ala Pro Arg Val Leu Leu Phe Cys Leu Leu Gly Leu Ala
 1               5                  10                  15
Val Thr Glu Gly His Gly Leu Glu Ala Ala Val Pro Ile Pro Gly Cys
            20                  25                  30
His Leu His Pro Phe Asn Val Thr Val Arg Ser Asp Arg His Gly Thr
        35                  40                  45
Cys Gln Gly Ser His Val Ala Gln Ala Cys Val Gly His Cys Glu Ser
    50                  55                  60
Ser Ala Phe Pro Ser Arg Tyr Ser Val Leu Val Ala Ser Gly Tyr Arg
65                  70                  75                  80
His Asn Ile Thr Ser Val Ser Gln Cys Cys Thr Ile Ser Ser Leu Lys
                85                  90                  95
Lys Val Arg Val Trp Leu His Cys Val Gly Asn Gln Arg Gly Glu Leu
            100                 105                 110
Glu Ile Phe Thr Ala Arg Ala Cys Gln Cys Asp Met Cys Arg Leu Ser
        115                 120                 125
Arg Tyr
    130

<210> SEQ ID NO 40
<211> LENGTH: 18
<212> TYPE: DNA
<213> ORGANISM: Artificial Sequence
<220> FEATURE:
<223> OTHER INFORMATION: Oligonucleotide primer

<400> SEQUENCE: 40
ccgtttctcc cgctacta                                                  18

<210> SEQ ID NO 41
<211> LENGTH: 18
<212> TYPE: DNA
<213> ORGANISM: Artificial Sequence
<220> FEATURE:
<223> OTHER INFORMATION: Oligonucleotide primer

<400> SEQUENCE: 41
gggccaacct catcttca                                                  18

<210> SEQ ID NO 42
<211> LENGTH: 32
<212> TYPE: DNA
<213> ORGANISM: Artificial Sequence
<220> FEATURE:
<223> OTHER INFORMATION: Oligonucleotide primer (ZC17438)

<400> SEQUENCE: 42
gatcagggcc ggccaccatg cctatggcgt cc                                  32

<210> SEQ ID NO 43
<211> LENGTH: 32
<212> TYPE: DNA
<213> ORGANISM: Artificial Sequence
<220> FEATURE:
<223> OTHER INFORMATION: Oligonucleotide primer (ZC17439)

<400> SEQUENCE: 43 gatcaggggcg cgccctagta gcgagagagg cg                                 32

<210> SEQ ID NO 44
```

```
<211> LENGTH: 32
<212> TYPE: DNA
<213> ORGANISM: Artificial Sequence
<220> FEATURE:
<223> OTHER INFORMATION: Oligonucleotide primer (ZC17950)

<400> SEQUENCE: 44
cgtatcggcc ggccaccatg cccatggcac ca                              32

<210> SEQ ID NO 45
<211> LENGTH: 32
<212> TYPE: DNA
<213> ORGANISM: Artificial Sequence
<220> FEATURE:
<223> OTHER INFORMATION: Oligonucleotide primer (ZC17951)

<400> SEQUENCE: 45
cgtacgggcg cgccctagta gcgggagaaa cg                              32

<210> SEQ ID NO 46
<211> LENGTH: 6
<212> TYPE: PRT
<213> ORGANISM: Artificial Sequence
<220> FEATURE:
<223> OTHER INFORMATION: Peptide tag

<400> SEQUENCE: 46

Glu Tyr Met Pro Met Glu
 1               5

<210> SEQ ID NO 47
<211> LENGTH: 6
<212> TYPE: PRT
<213> ORGANISM: Artificial Sequence
<220> FEATURE:
<223> OTHER INFORMATION: Peptide

<400> SEQUENCE: 47

Glu Tyr Met Pro Val Asp
 1               5

<210> SEQ ID NO 48
<211> LENGTH: 21
<212> TYPE: DNA
<213> ORGANISM: Artificial Sequence
<220> FEATURE:
<223> OTHER INFORMATION: Oligonucleotide primer (ZC12700)

<400> SEQUENCE: 48
ggaggtctat ataagcagag c                                         21

<210> SEQ ID NO 49
<211> LENGTH: 20
<212> TYPE: DNA
<213> ORGANISM: Artificial Sequence
<220> FEATURE:
<223> OTHER INFORMATION: Oligonucleotide primer (ZC12742)

<400> SEQUENCE: 49
ttatgtttca ggttcagggg                                           20
```